United States Patent
Xie

(10) Patent No.: US 12,411,126 B2
(45) Date of Patent: *Sep. 9, 2025

(54) NANOPORE SENSOR HAVING A FLUIDIC PASSAGE AND TRANSISTOR SENSING OF LOCAL ELECTRICAL POTENTIAL AT THE FLUIDIC PASSAGE

(71) Applicant: President and Fellows of Harvard College, Cambridge, MA (US)

(72) Inventor: Ping Xie, Needham, MA (US)

(73) Assignee: President and Fellow of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/672,910

(22) Filed: May 23, 2024

(65) Prior Publication Data

US 2024/0310356 A1    Sep. 19, 2024

Related U.S. Application Data

(60) Continuation of application No. 17/007,290, filed on Aug. 31, 2020, now Pat. No. 11,994,507, which is a
(Continued)

(51) Int. Cl.
*G01N 27/327* (2006.01)
*B01L 3/00* (2006.01)
(Continued)

(52) U.S. Cl.
CPC .. *G01N 33/48721* (2013.01); *B01L 3/502715* (2013.01); *B01L 3/50273* (2013.01);
(Continued)

(58) Field of Classification Search
CPC ......... G01N 33/48721; G01N 27/4146; G01N 27/4473; G01N 27/44791;
(Continued)

(56) References Cited

U.S. PATENT DOCUMENTS 6,870,361 B2    3/2005  Chopra et al.
6,919,002 B2    7/2005  Chopra et al.
(Continued)

FOREIGN PATENT DOCUMENTS

CN    102901763 A    1/2013
JP    2014190891 A    10/2014
(Continued)

OTHER PUBLICATIONS

PCT/US2016/016664, Form PCT/ISA/210 first sheet, continuation of first sheet (3), continuation of first sheet (2), second sheet, continuation of second sheet, patent family annex, and further information continued from PCT/ISA/210, Aug. 2016.
(Continued)

*Primary Examiner* — Alexander S Noguerola
(74) *Attorney, Agent, or Firm* — Theresa A. Lober

(57) ABSTRACT

A nanopore sensor includes a nanopore disposed in a support structure with a nanopore diameter and having a nanopore fluidic resistance, $R_{Pore}$. A fluidic passage, is disposed in fluidic connection between a first fluidic reservoir of ionic concentration solution and the nanopore, and includes a passage length having a fluidic passage width, along at least a portion of a fluidic passage length, that is greater than the diameter of the nanopore and less than the fluidic passage length. The fluidic passage has a fluidic passage fluidic resistance, $R_{FP}$, of at least about 10% of the nanopore fluidic resistance, $R_{Pore}$, and no more than about 10 times the nanopore fluidic resistance, $R_{Pore}$. The nanopore is disposed in fluidic connection between the fluidic passage and a second fluidic reservoir of ionic concentration solution. At least one transistor is operatively connected electrically to sense electrical potential local to the fluidic passage.

23 Claims, 31 Drawing Sheets

Related U.S. Application Data division of application No. 15/015,277, filed on Feb. 4, 2016, now Pat. No. 10,794,895.

(60) Provisional application No. 62/112,630, filed on Feb. 5, 2015.

(51) Int. Cl.

| | |
|---|---|
| *C12Q 1/6869* | (2018.01) |
| *G01N 27/414* | (2006.01) |
| *G01N 27/416* | (2006.01) |
| *G01N 27/447* | (2006.01) |
| *G01N 27/453* | (2006.01) |
| *G01N 33/487* | (2006.01) |

(52) U.S. Cl.
CPC ....... *C12Q 1/6869* (2013.01); *G01N 27/4145* (2013.01); *G01N 27/4146* (2013.01); *G01N 27/4163* (2013.01); *G01N 27/44726* (2013.01); *G01N 27/4473* (2013.01); *G01N 27/44791* (2013.01); *B01L 2300/0645* (2013.01); *B01L 2300/0867* (2013.01); *B01L 2300/0896* (2013.01); *B01L 2300/12* (2013.01); *B01L 2400/0421* (2013.01)

(58) Field of Classification Search
CPC ........... B01L 3/502715; B01L 3/50273; B01L 2400/0421; C12Q 1/6869
See application file for complete search history.

(56) References Cited

U.S. PATENT DOCUMENTS

| | | | |
|---|---|---|---|
| 7,846,738 | B2 | 12/2010 | Golovchenko et al. |
| 7,910,064 | B2 | 3/2011 | Hamilton et al. |
| 8,748,091 | B2 | 6/2014 | Timp et al. |
| 8,901,914 | B2 | 12/2014 | Fraikin et al. |
| 8,986,928 | B2 | 3/2015 | Turner et al. |
| 8,993,234 | B2 | 3/2015 | Turner et al. |
| 9,017,937 | B1 | 4/2015 | Turner et al. |
| 9,535,033 | B2 | 1/2017 | Kawai et al. |
| 10,436,747 | B2 | 10/2019 | Lieber et al. |
| 11,946,925 | B2 * | 4/2024 | Xie ................ G01N 27/4163 |
| 2002/0142344 | A1 | 10/2002 | Akeson et al. |
| 2003/0044816 | A1 | 3/2003 | Denison et al. |
| 2006/0063171 | A1 | 3/2006 | Akeson et al. |
| 2006/0068401 | A1 | 3/2006 | Flory et al. |
| 2006/0210995 | A1 | 9/2006 | Joyce |
| 2006/0275778 | A1 * | 12/2006 | Wu ................ G01N 33/48721 977/924 |
| 2006/0275779 | A1 | 12/2006 | Li et al. |
| 2007/0178507 | A1 | 8/2007 | Wu et al. |
| 2008/0171316 | A1 | 7/2008 | Golovchenko |
| 2010/0066348 | A1 * | 3/2010 | Merz ................ C12Q 1/6869 257/253 |
| 2010/0243449 | A1 | 9/2010 | Oliver |
| 2010/0327847 | A1 | 12/2010 | Leiber |
| 2010/0331194 | A1 * | 12/2010 | Turner ............ G01N 27/447 438/49 |
| 2011/0236984 | A1 | 9/2011 | Sun et al. |
| 2011/0308949 | A1 | 12/2011 | Afzali-Azdakani et al. |
| 2012/0094278 | A1 | 4/2012 | Akeson et al. |
| 2012/0193237 | A1 | 8/2012 | Afzali-Ardakani et al. |
| 2012/0267729 | A1 | 10/2012 | Dang et al. |
| 2013/0161194 | A1 | 6/2013 | Jeon et al. |
| 2013/0265031 | A1 | 10/2013 | Shim et al. |
| 2014/0055150 | A1 | 2/2014 | Kawai et al. |
| 2014/0056763 | A1 | 2/2014 | Peng |
| 2014/0174927 | A1 | 6/2014 | Bashir et al. |
| 2014/0183040 | A1 | 7/2014 | Kawai et al. |
| 2014/0190833 | A1 | 7/2014 | Lieber et al. |
| 2014/0326954 | A1 | 11/2014 | Han et al. |
| 2015/0068902 | A1 | 3/2015 | Afzali-Ardakani et al. |
| 2015/0275288 | A1 | 10/2015 | Luan et al. |
| 2016/0032236 | A1 | 2/2016 | Nivala |
| 2020/0179880 | A1 | 6/2020 | Xie et al. |
| 2020/0400649 | A1 | 12/2020 | Xie |
| 2021/0310987 | A1 | 10/2021 | Xie et al. |
| 2022/0236251 | A1 | 7/2022 | Xie et al. |
| 2022/0260522 | A1 | 8/2022 | Xie et al. |

FOREIGN PATENT DOCUMENTS

| | | | | |
|---|---|---|---|---|
| WO | | 2010117470 A3 | 3/2011 | |
| WO | WO 2012138357 A1 * | | 10/2012 | ............... C12Q 1/68 |
| WO | | 2013041878 A1 | 3/2013 | |
| WO | | 2013088098 A2 | 6/2013 | |
| WO | | 2013123379 A2 | 8/2013 | |
| WO | | 2014165168 A1 | 10/2014 | |
| WO | | 2014181203 A2 | 11/2014 | |
| WO | | 2019160925 A1 | 8/2019 | |
| WO | | 2020183172 A9 | 9/2020 | |
| WO | | 2021255414 A1 | 12/2021 | |
| WO | | 2022013551 A | 1/2022 | |

OTHER PUBLICATIONS

PCT/US2016/016664, WIPO Written Opinion Form PCT/ISA/237-cover sheet, Form PCT/ISA/237-4 sheets, Form PCT/ISA/237 Separate sheet Sheets 2-4, Aug. 2016.

European Patent Application 16706099.5-1559, EPO Communication pursuant to Rules 161(1) and 162 EPC, pp. 1-2, Sep. 2017.

European Patent Application 16706099.5-1559, Applicant response to EPO Communication, pp. 1-6, marked-up claims, pp. 1-6, claims, pp. 1-3, Mar. 2018.

Ivankin et al., "Label-Free Optical Detection for Biomolecular Translocation through Nanopore Arrays," ACS NANO, vol. 8, No. 10, pp. 10774-10781, Sep. 2014.

Kunitake, "Synthetic Bilayer Membranes: Molecular Design, Self-Organization, and Application," Angew. Chem. Int. Ed. Engl. V. 31, pp. 709-726, 1992.

Archer et al., "Fabrication and Characterization of Silicon Micro-Funnels and Tapered Micro-Channels for Stochastic Sensing Applications," Sensors, vol. 8, pp. 3848-3872, Jun. 2008.

Choi, "Polymer-based fluidic devices integrated with perforated micro- and nanopore membrane for study of ionic and DNA transport," Dissertation for PhD, Dept. Mech. Eng., Louisiana State University, Aug. 2013.

Huisman et al., "A new way to integrate solid state nanopores for translocation experiments," Microelectronic Engineering, vol. 85, pp. 1311-1313, Feb. 2008.

Yanagi et al., "A Novel Side-gated Ultrathin-channel Nanopore FET (SGNAFET) Sensor for Direct DNA Sequencing," IEEE Electron Devices Meeting 2013, pp. IEDM13-377-IEDM13-380, Dec. 2013.

Yanagi et al., "Fabricating nanopores with diameters of sub-1 nm to 3 nm using multilevel pulse-voltage injection," Scientific Reports, 4:5000, pp. 1-7, May 2014.

Uddin et al., "Integration of solid-state nanopores in a 0.5 micron CMOS foundry process," Nanotechnology, vol. 24, pp. 155501-1-155501-13, Mar. 2013.

Japanese patent application No. 2017-540674, Written Amendment of Claims, pp. 1-6, Feb. 2019.

Chinese patent application No. 201680019980.7, Filing with claim amendments, pp. 1-2, claim amendments, pp. 1-8, Apr. 2018.

Chinese patent application No. 201680019980.7, Office Action from National Intellectual Property Administration, P.R. China, pp. 1-5, Feb. 19, 2019.

Chinese patent application No. 201680019980.7, Response to Office Action, pp. 1-2, amended claims, pp. 1-8., Sep. 2, 2019.

Chinese patent application No. 201680019980.7, Office Action from National Intellectual Property Administration, P.R. China, pp. 1-5, Mar. 9, 2020.

Chinese patent application No. 201680019980.7, Response to Office Action, pp. 1-2, amended claims, pp. 3-10, Apr. 27, 2020.

Traversi et al., "Detecting the translocation of DNA through a nanopore using graphene nanoribbons," nature nanotechnology, Advance online publication, www.nature.com/naturenanotechnology, pp. 1-7, Nov. 2013.

(56) References Cited

OTHER PUBLICATIONS

Rudenko et al., "Controlled gating and electrical detection of single 50S ribosomal subunits through a solid-state nanopore in a microfluidic chip," Biosensors and Bioelectronics, vol. 29, pp. 34-39, Aug. 2011.
Zhang, "Combined Nanochannel-Nanopore Device for Single-Molecule DNA Analysis and Manipulation," McGill University, Thesis for the Master of Science, pp. 1-84, 2012.
Patel, "Rapid Translocation of DNA Molecules Through Graphene Nanogaps," California State University, Northridge, Thesis for the Master of Science, pp. 1-36, May 2012.
Pandey, "Towards a biochip for ion channel research," Lehigh University, Thesis, pp. 1-84, Jun. 2001.
Mao, "Ultra-High-Aspect-Ratio Nanofluidic Channels for High-Throughput Biological Applications," Massachusetts Institute of Technology, Thesis for the Doctor of Philosophy, pp. 1-133, accessioned May 2010.
Chinese patent application No. 201680019980.7, Office Action and Search Report from National Intellectual Property Administration, P.R. China, pp. 1-7, Oct. 2019.
Japanese patent application No. 2020-195190, JPO Notice of Reasons for Rejection, pp. 1-4, Jan. 2022.
Japanese patent application No. 2020-195190, Response to JPO Notice of Reasons for Rejection, Written Argument pp. 1-7, Amendments to the claims pp. 1-3, Jun. 2022.
European Patent Application 16706099.5-1559, Response to EPO Communication Letter pp. 1-2, Clean copy of claims including amendments pp. 1-3, Marked-up copy of claims including amendments pp. 1-3, receipt p. 1, Jun. 2021.
European Patent Application 16706099.5-1559, EPO Communication EPO Form 2001 Sheets 1-2, EPO Form 2906 Sheets 1-3, Jun. 2021.
European Patent Application 16706099.5-1559, Response to EPO Communication Letter pp. 1-4, Clean copy of claims including amendments pp. 1-3, Marked-up copy of claims including amendments pp. 1-4, receipt p. 1, Oct. 2021.
Japanese patent application No. 2017-540674, JPO Notice of Reasons for Rejection, pp. 1-2, Dec. 2019.
Japanese patent application No. 2017-540674, Response to JPO Notice of Reasons for Rejection Written Argument pp. 1-6, Marked-up copy of claims including amendments pp. 1-5, May 2020.
Japanese patent application No. 2020-195192, JPO Notice of Decision to Grant a Patent pp. 1-3, and Claims filed and allowed pp. 1-3, Jan. 2022.
Japanese patent application No. 2020-195190, JPO Notice of Reasons for rejection, pp. 1-2, Oct. 2022.
European Patent Application 16706099.5-1559, Amendment to claim 1 for patent grant, p. 1, Nov. 2022.
Japanese patent application No. 2020-195190, Response to JPO Notice of Reasons for rejection, pp. 1-2, and claim amendments pp. 1-3, Nov. 2022.
Fluigent, "Microfluidic Resistance," downloaded Aug. 17, 2023, from https://www.fluigent.com/resources-support/expertise/expertise-reviews/concepts-and-physics-of-microfluidics/microfluidic-resistance/, 2023.
CN 202010965386.5, Applicant Response to CNIPA Office Communication, pp. 1-10, Claim Amendments filed with Response, pp. 1-5, Jan. 29, 2024.
European Patent Application No. 23191347.6-1001/4293349 EPO Form 1507N Communication, p. 1 of 1; European Search Report, pp. 1-2; Annex to the European Search Report, pp. 1-2; EPO Form P04A42 Information on Search Strategy, p. 1 of 1; EPO Form 170301.91TRI Examination, Sheets 1-5; Listing of claims examined, pp. 1-3, Jan. 18, 2024.
European Patent Application No. 23191347.6-1001/4293349, Response to examination pp. 1-13, marked-up listing of claims with amendments, pp. 1-3, Aug. 21, 2024.
European Patent Application No. 23191347.6-1001, Communication pursuant to Article 94(3)EPC: EPO Form 2001 sheets 1-2, and EPO Form 2906 Sheets 1-5, Apr. 4, 2025.

* cited by examiner

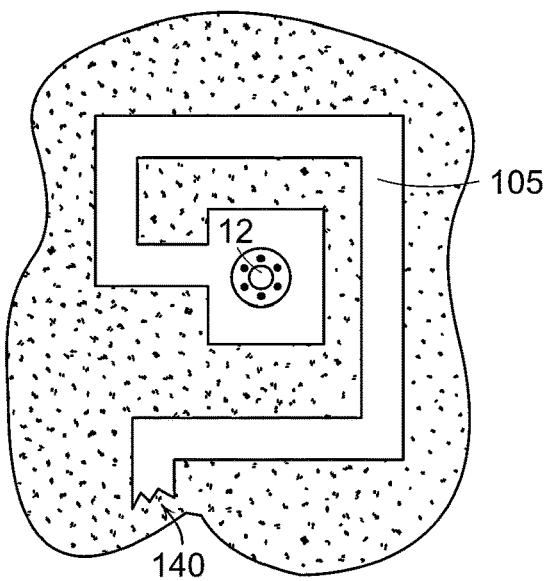
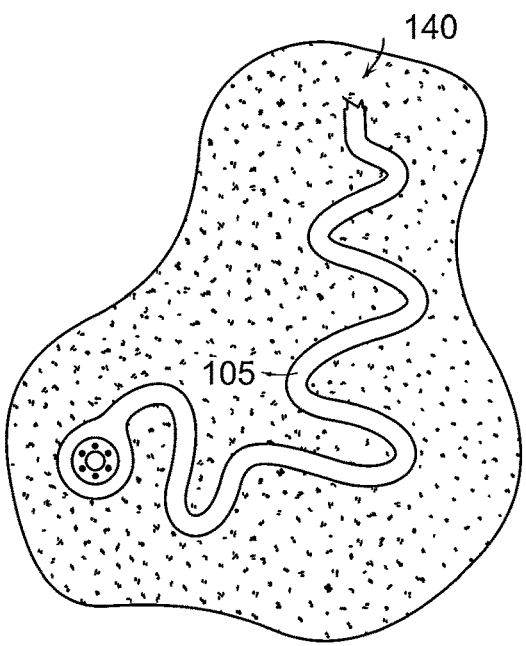
FIG. 15A  FIG. 15B
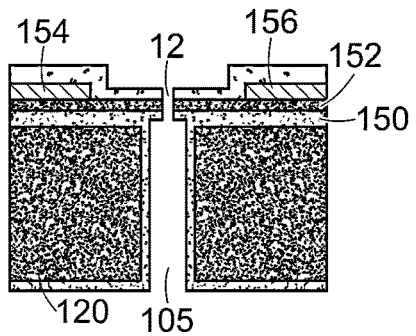
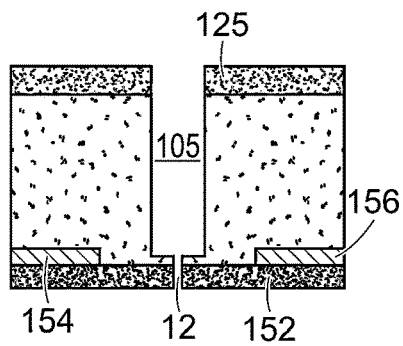
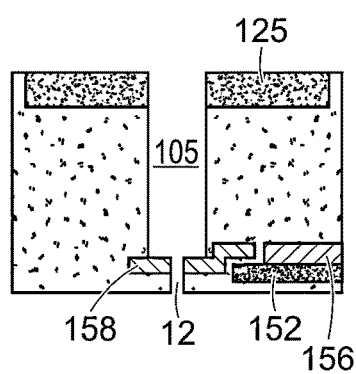
FIG. 16A  FIG. 16B  FIG. 16C
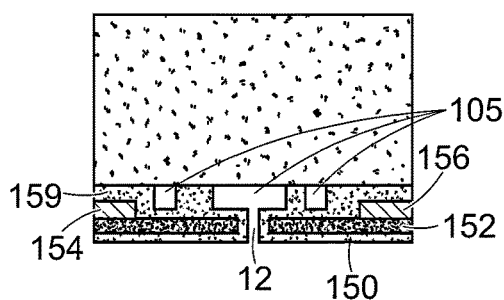
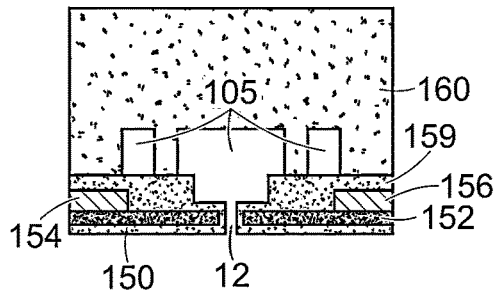
FIG. 16D  FIG. 16E

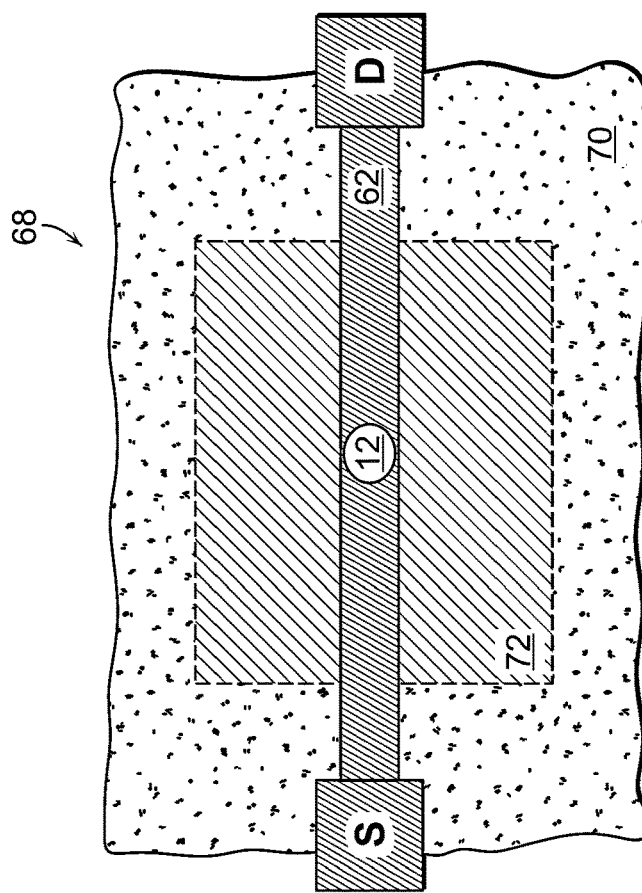
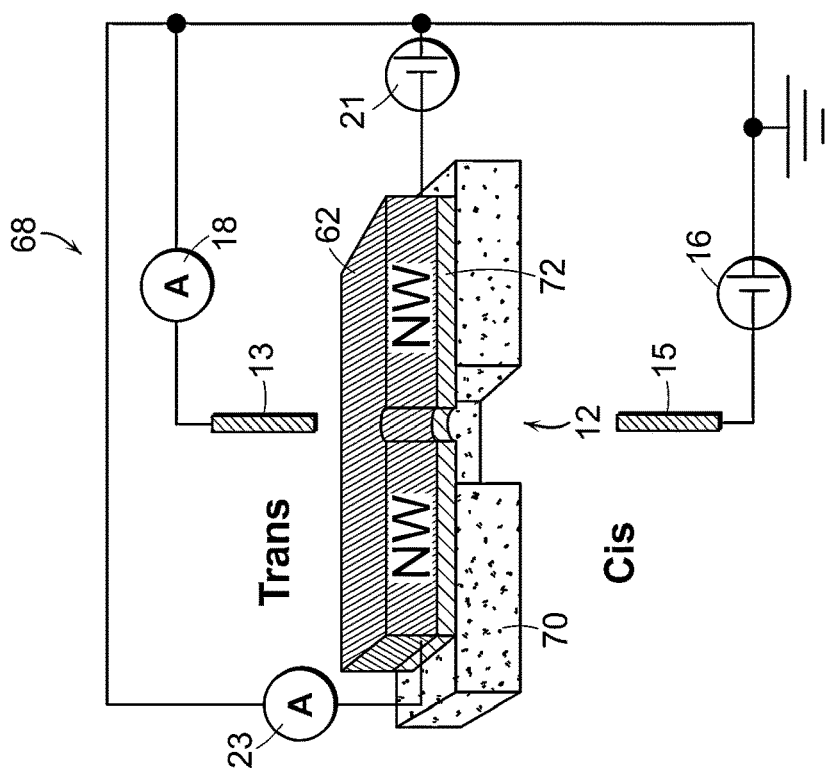
FIG. 19B
FIG. 19A

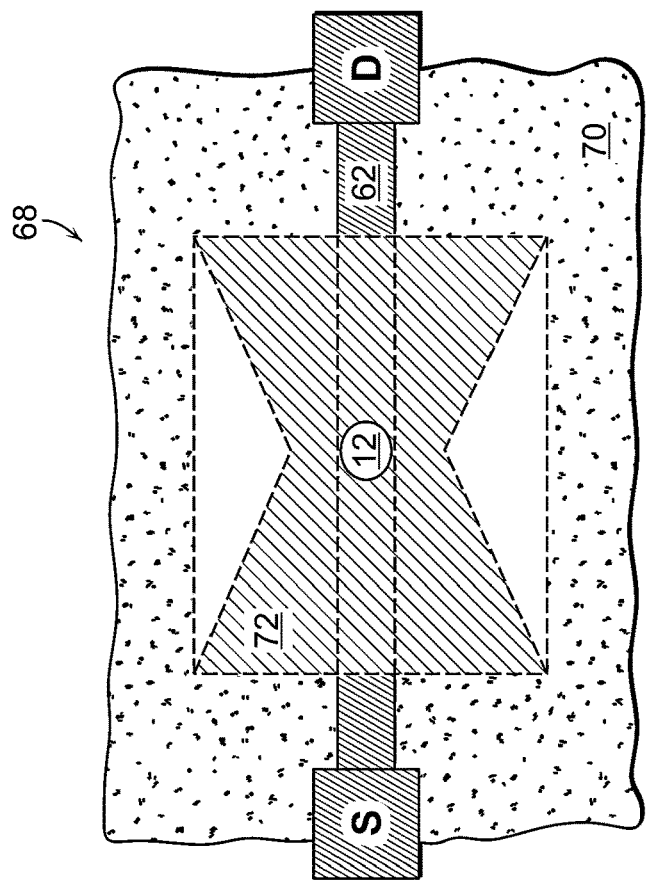
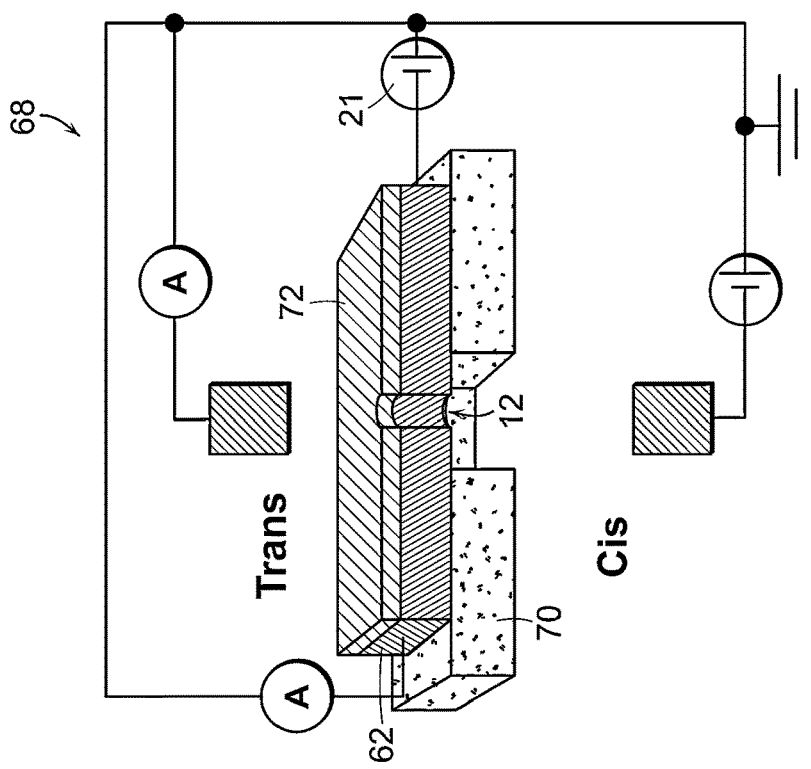
FIG. 20B
FIG. 20A

NANOPORE SENSOR HAVING A FLUIDIC PASSAGE AND TRANSISTOR SENSING OF LOCAL ELECTRICAL POTENTIAL AT THE FLUIDIC PASSAGE

CROSS-REFERENCE TO RELATED APPLICATIONS

This application is a continuation of U.S. application Ser. No. 17/007,290, filed Aug. 31, 2020, which is a divisional of U.S. application Ser. No. 15/015,277, filed Feb. 4, 2016, now U.S. Pat. No. 10,794,895, which claims the benefit of U.S. Provisional Application No. 62/112,630, filed Feb. 5, 2015, the entirety of all of which are hereby incorporated by reference.

STATEMENT REGARDING FEDERALLY SPONSORED RESEARCH

This invention was made with government support under OD003900 awarded by the National Institutes of Health. The government has certain rights in the invention.

BACKGROUND

This invention relates generally to sensing systems that employ a nanopore sensor, and more particularly relates to techniques for sensing species as the species translocate a nanopore sensor.

Both solid-state nanopores and biological nanopores are increasingly the focus of considerable effort in the development of a low cost, high throughput sensing system that can be employed for sensing a wide range of species, including single molecules such as polymer molecules. A common approach in nanopore-based sensing employs the measurement of ionic current flow through a nanopore that is provided in a highly resistive amphiphilic membrane between electrodes provided on either side of the membrane. As a molecule such as a polymer analyte like DNA is caused to translocate the nanopore, the ionic current flow through the nanopore is modulated by the different nucleotide bases of a DNA strand. Measurement in changes in ionic current flow can be carried out in order to determine a sequence characteristic of the polymer strand. Nanopore devices for detection of analytes other than polynucleotides have also been reported, for example in International Patent Application PCT/US2013/026414, published as WO2013/123379, for the detection of proteins. Whilst there has also been considerable effort in developing methods and systems using solid state nanopores in order to sequence DNA, there remain a host of challenges for commercial realization. In addition, various configurations of nanopores pose particular challenges. For example, in the use of an array of nanopores in which ionic current flow through each nanopore in the array can be measured, a measurement can be made between a common electrode and a plurality of electrodes provided on the respective opposite side of each nanopore. Here the plurality of electrodes needs to be electrically isolated from each other, limiting the level of integration density of nanopore devices.

Biological nanopores in some respects are advantageous over solid state nanopores in that they provide a constant and reproducible physical aperture. However the amphiphilic membranes in which they are provided are in general fragile and may be subject to degradation, providing ionic leakage pathways through the membrane. The speed of translocation of an analyte through a biological nanopore can be controlled by the use of an enzyme. Enzyme-assisted translocation of polynucleotides is typically on the order of 30 bases/second. In order to increase the throughput rate of analyte, much higher translocation speeds are desirable, but it is found that in general, the measurement of the a sensing signal can be problematic.

In order to circumvent the technical challenges posed by the ionic current measurement method for nanopore sensing, several alternative nanopore sensing methods have been proposed. Such alternative methods are in general directed to an arrangement in which there is recorded relatively local nanopore signals employing electronic sensors that are integrated with the nanopore. These nanopore sensing methods include, e.g., measurement of capacitive coupling across a nanopore and tunnelling current measurements through a species translocating a nanopore. While providing interesting alternative sensing techniques, such capacitive coupling and tunnelling current measurement techniques have not yet improved upon the conventional ionic current detection technique for nanopore sensing, and ionic current detection techniques remain challenged by signal amplitude and signal bandwidth issues.

SUMMARY OF THE INVENTION

There is provided herein a nanopore sensor that overcomes the limitations of signal amplitude and signal bandwidth demonstrated by conventional nanopore sensors. In the nanopore sensor provided herein, a nanopore is disposed in a support structure, the nanopore having a nanopore diameter and a nanopore fluidic resistance, $R_{Pore}$. There is provided a fluidic passage disposed in fluidic connection between the nanopore and a first fluidic reservoir including a fluidic solution having a first ionic concentration. The fluidic passage includes a passage length having a fluidic passage width, along at least a portion of a fluidic passage length, that is greater than the diameter of the nanopore and that is less than the fluidic passage length. The fluidic passage has a fluidic passage fluidic resistance, $R_{FP}$, of at least about 10% of the nanopore fluidic resistance, $R_{Pore}$, and no more than about 10 times the nanopore fluidic resistance, $R_{Pore}$. The nanopore is disposed in fluidic connection between the fluidic passage and a second fluidic reservoir including a fluidic solution having a second ionic concentration. At least one transistor is operatively connected electrically to sense electrical potential local to the fluidic passage.

This nanopore sensor enables high sensitivity and large bandwidth, with a localized, large sensing signal. As a result, nanopore sensing applications such as DNA sequencing can be accomplished with the nanopore sensor at a very high integration density and throughput of analyte. Other features and advantages of the invention will be apparent from the following description and accompanying figures, and from the claims.

BRIEF DESCRIPTION OF THE DRAWINGS

FIGS. 15A-15B are schematic top-down cross sections of example lateral fluidic passage configurations;

FIGS. 16A-16E are schematic side views of fluidic passage configurations arranged with elements for making a local electrical potential measurement.

FIGS. 19A-19B are a schematic view of a nanopore sensor configured for local electrical potential measurement with a nanowire FET disposed on a graphene membrane, and a plan view of an example implementation of this nanopore sensor, respectively;

FIGS. 20A-20B are a schematic view of a nanopore sensor configured for local electrical potential measurement with a graphene layer disposed on a nanowire FET, and a plan view of an example implementation of this nanopore sensor, respectively;

DETAILED DESCRIPTION

Figure 1A:
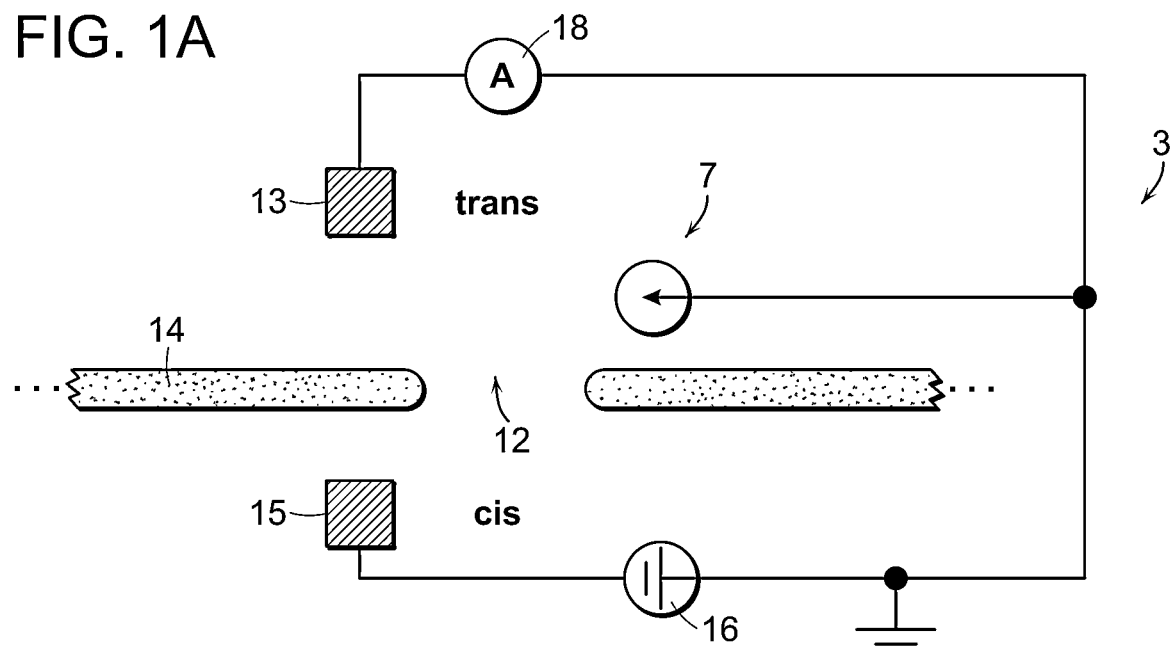
FIG. 1A is a schematic circuit diagram of a first example nanopore sensor configuration for measuring local electrical potential.

FIGS. 1A-1E are schematic views of nanopore sensor configurations provided herein that enable a local electrical potential sensing method for nanopore sensing. For clarity of discussion, device features illustrated in the figures are not shown to scale. Referring to FIG. 1A, there is shown a nanopore sensor 3 including a support structure 14, such as a membrane, in which is disposed a nanopore 12. The nanopore 12 is configured in the support structure between two fluidic reservoirs shown here schematically as a trans reservoir and a cis reservoir such that the nanopore 12 is the only path of fluidic communication between the cis and trans reservoirs. One reservoir is connected to an inlet to the nanopore while the other reservoir is connected to an outlet from the nanopore. In operation of the nanopore sensor for local electrical potential measurement detection of species translocation through the nanopore, one or more objects of a species, such as molecules, are provided in a fluidic solution in one of the reservoirs for translocation through the nanopore to the other of the two reservoirs. For many applications, and in particular for molecular sensing applications, it can be preferred to provide the molecules or other species objects in an ionic fluidic solution in one of the reservoirs, and can be provided in either one of the reservoirs.

The species objects to be translocated through the nanopore can include objects selected from, for example, DNA, DNA fragments, RNA, RNA fragments, PNA, nucleotides, nucleosides, oligonucleotides, proteins, polypeptides, amino acids and polymers. The species objects can include a tag that is released from a tagged nucleotide. With the aid of a polymerase, nucleotides along a nucleic acid molecule can be polymerized to generate a nucleic acid strand that is complementary to at least a portion of the nucleic acid molecule, whereby, during polymerization, a tag is released from an individual nucleotide of the nucleotides, and whereby the released tag translocates the nanopore, as described in WO 2013/191793, hereby incorporated by reference.

The nanopore may be provided as an aperture, gap, channel, groove, pore or other hole in the support structure and is provided with an extent, such as a diameter, for a corresponding geometry, that is suitable for sensing species objects of interest. For sensing molecule translocation through the nanopore, a nanopore of less than about 100 nm can be preferred, and a nanopore of less than 10 nm, 5 nm, or 2 nm can be more preferred. As discussed below, a nanopore of 1 nm can be suitable and even preferred for some molecular sensing applications.

The reservoirs or other components of the nanopore sensor may be configured to provide a driving force for moving objects of a species, such as molecules, toward the nanopore or through the nanopore from one of the reservoirs to the other of the reservoirs. For example, electrodes 13, 15 can be provided in a circuit with voltage and current elements 16, 18 to produce an electrophoretic force between the reservoirs for electrophoretically driving the species in the solution, towards the nanopore or through the nanopore from one reservoir to the other reservoir. To enable electrophoretic driving of the species, the fluidic solutions of the reservoirs can be provided as electrically conductive ionic solutions having pH and other characteristics that are amenable to the species in the solution. Thereby an electrical circuit can be connected with the reservoir solutions in series through the nanopore, with electrodes 13, 15 as shown in the figures, providing an electrical voltage bias between the solutions, across the nanopore. Translocation and control of the rate of translocation of species though the nanopore can be carried out with alternative techniques, such as an enzyme molecular motor.

In addition to or as an alternative to a driving force that is an applied voltage, a pressure gradient across the pore can be used to bring molecules towards the nanopore and/or through the nanopore. This pressure gradient can be produced by using a physical pressure, or a chemical pressure such as an osmotic pressure. An osmotic pressure can be produced from a concentration difference across the cis and trans chambers. The osmotic pressure can be produced by having a concentration gradient of an osmotically active agent, such as a salt, polyethelene glycol (PEG), or glycerol.

As shown in FIG. 1A, there can be provided in the nanopore sensor a transduction element 7 that senses the electrical potential local to the site of the element and that develops a characteristic that is indicative of that local electrical potential. An electrical connection, such as device or region of a device and/or circuit, a wire, or combination of circuit elements, that senses the electrical potential local to the site of the device and/or circuit can be provided as a transduction element 7, to develop a signal indicative of local electrical potential. The location of the electrical potential sensing can be in a reservoir, on a surface of the support structure, or other location within the nanopore sensor as described in detail below.

Figure 1C:
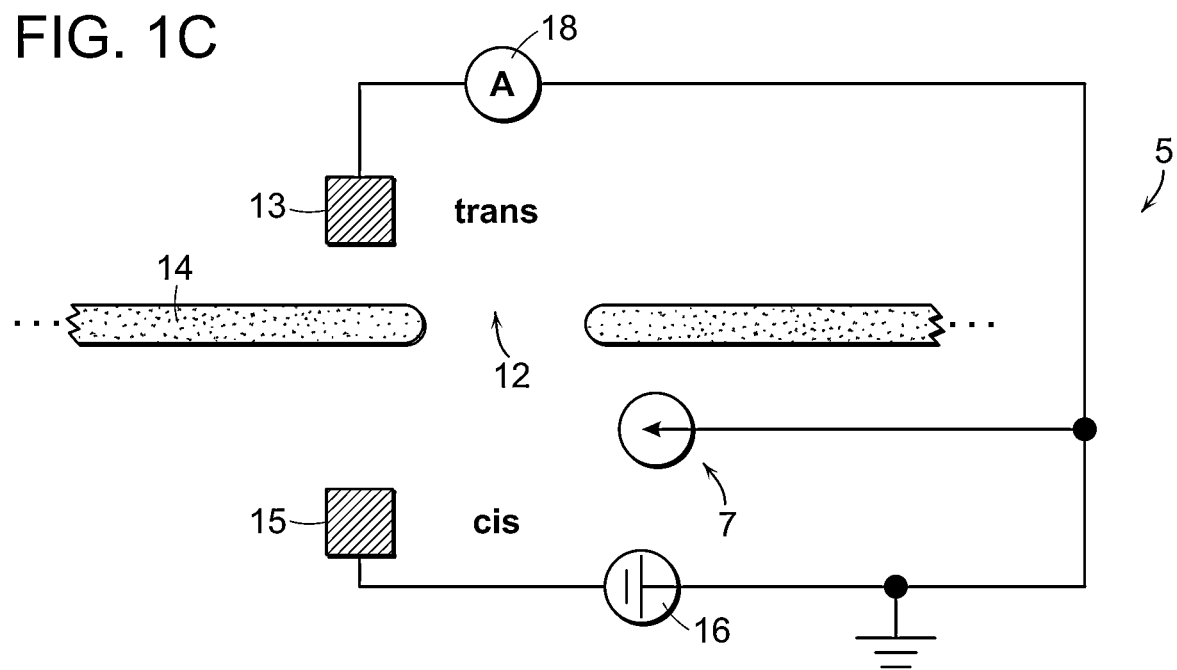
FIG. 1C is a schematic circuit diagram of a second example nanopore sensor configuration for measuring a local electrical potential.
Figure 1B:
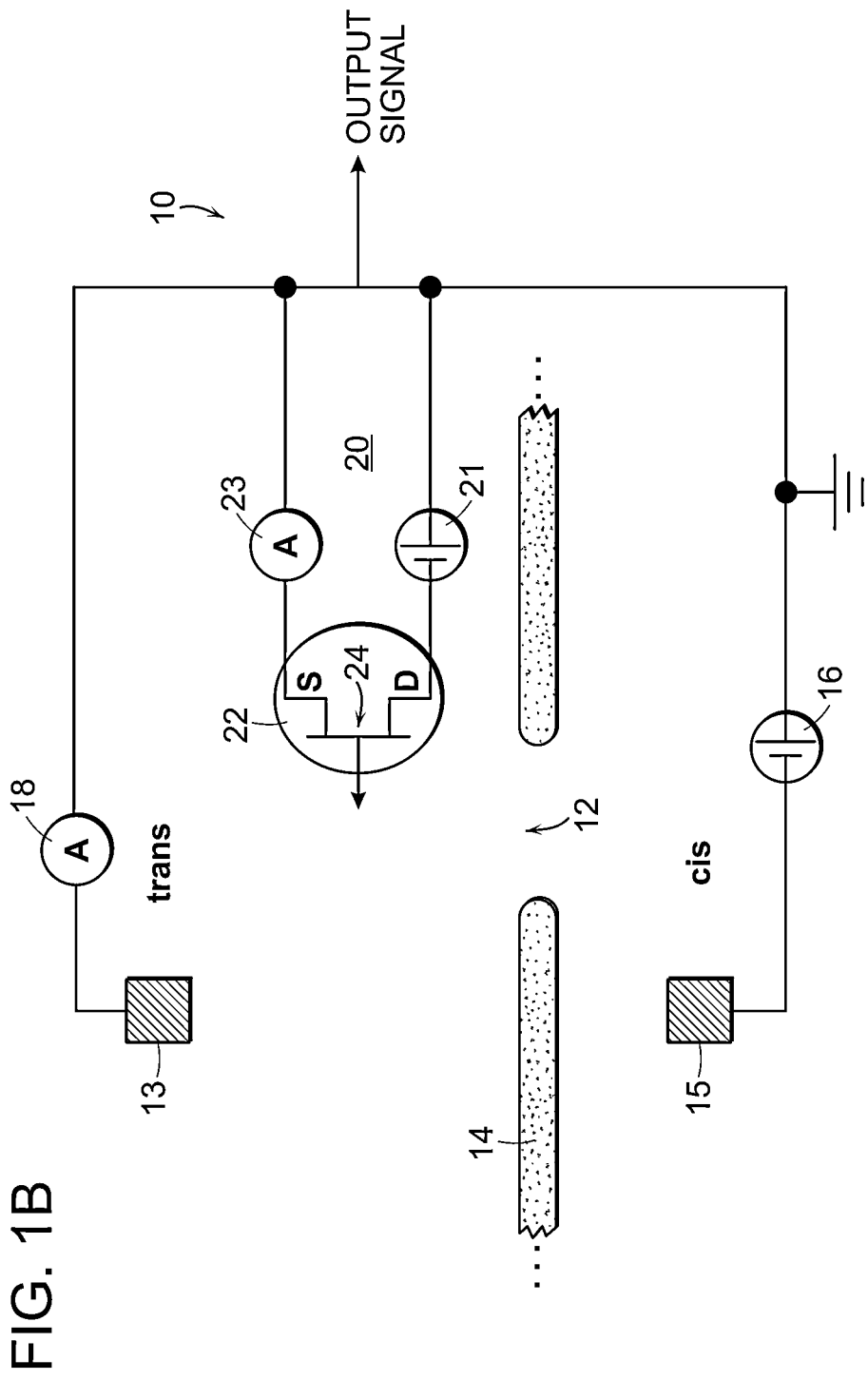
FIG. 1B is a circuit diagram of an example transistor implementation of the nanopore sensor configuration of FIG. 1A.

As shown in FIG. 1B, there can be provided a circuit 20 that includes, e.g., a transistor device 22, having a source, S, a drain, D, and a channel region 24. The channel region 24 is in this example physically disposed at a location in the nanopore sensor environment to make a local electrical potential measurement. This physical location of the channel region 24 of the transistor can be at any convenient and suitable site for accessing local electrical potential.

Figure 1D:
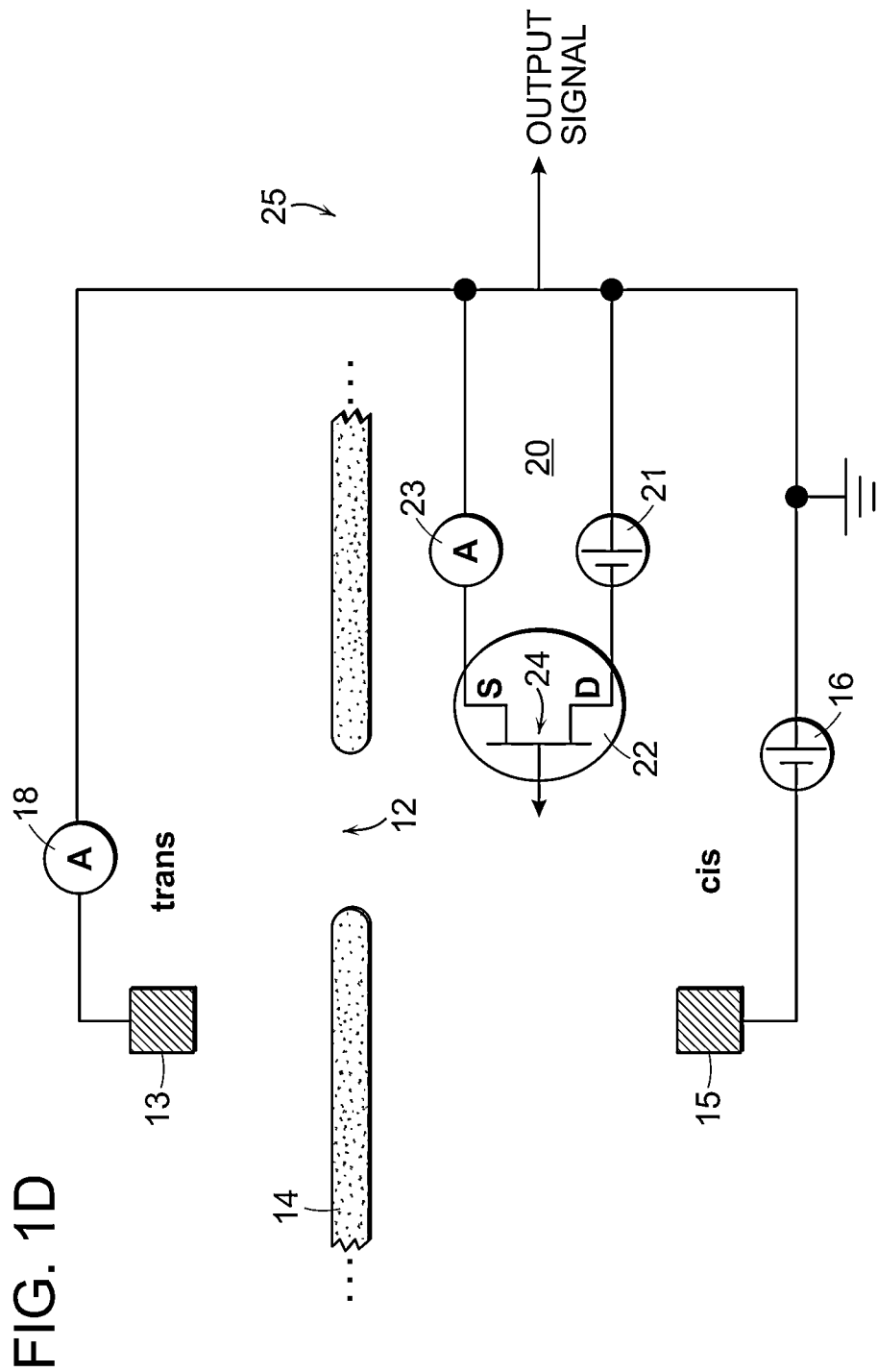
FIG. 1D is circuit diagram of an example transistor implementation of the nanopore sensor configuration of FIG. 1C.

In the arrangements of FIGS. 1A-1B, an electrical potential sensing circuit is configured local to the trans reservoir to provide a transistor or other device that measures the electrical potential local to the trans reservoir at the trans reservoir-side of the nanopore 12. Alternatively, as shown in FIG. 1C, an electrical transduction element 7, such as an electrical potential sensing device or circuit, can be configured at the cis reservoir side of the nanopore. Here, e.g., as shown in FIG. 1D, there can be provided a circuit 20 including a transistor 24 or other device for measuring electrical potential local to the cis reservoir at the cis reservoir side of the nanopore 12.

Figure 1E:
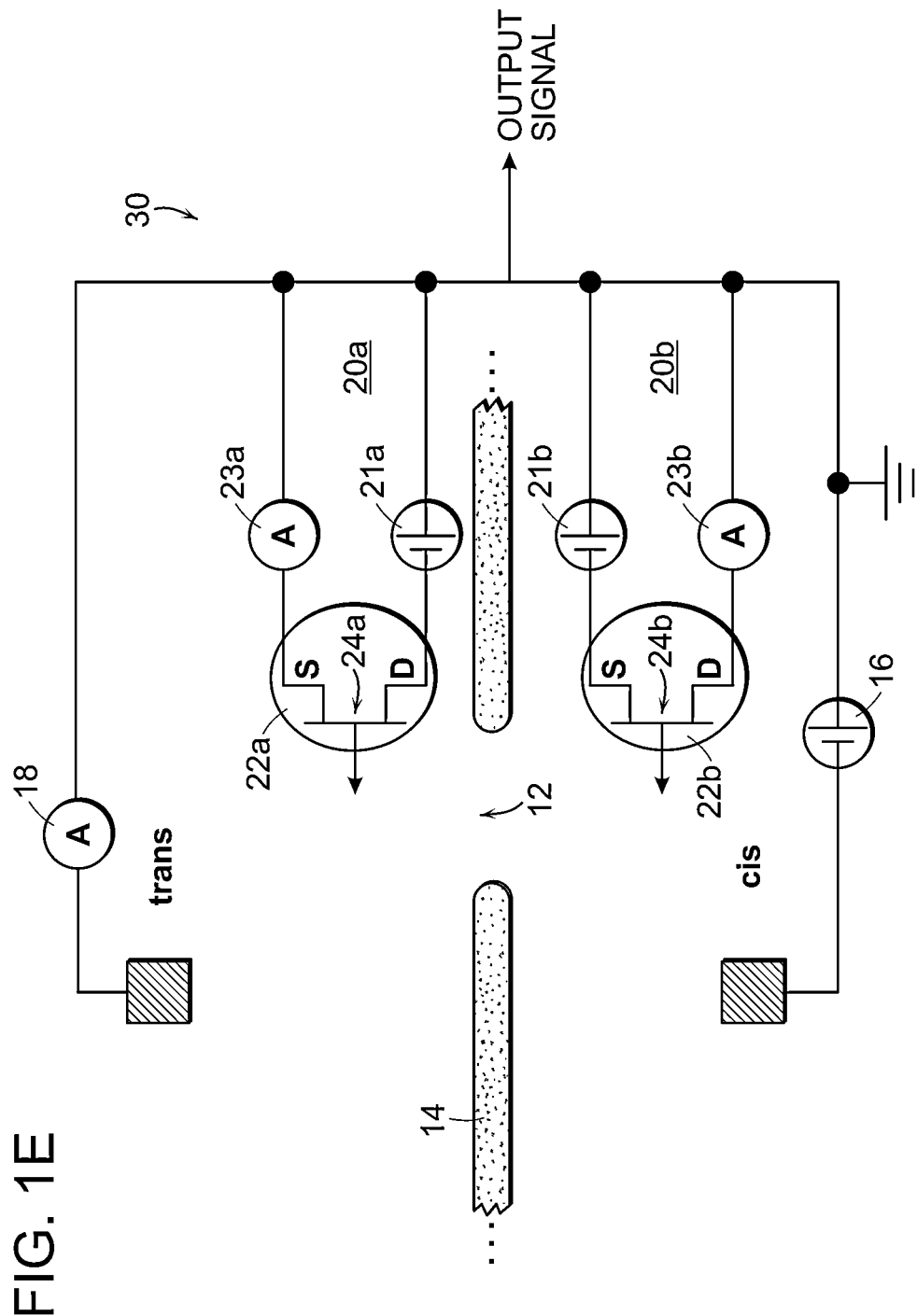
FIG. 1E is a circuit diagram of an example transistor implementation of a combination of the sensor configurations of FIGS. 1A and 1C.

In a further alternative configuration, as shown in FIG. 1E, there can be included two or more transduction elements, with circuits 20a, 20b, etc., connected to transduction elements such as transistors 22a, 22b that sense the electrical potential at two or more locations in the nanopore sensor system, such as each side of the nanopore support structure. Depending on the physical implementation of the electrical potential sensing circuit, the electrical potential at the two sides of the nanopore membrane 14 can thereby be measured with this arrangement. This is an example configuration in which is enabled a measurement of the difference in local potential between two sites in the nanopore sensor. It is therefore intended that the term "measured local electrical potential" refers to the potential at a single site in the nanopore sensor, refers to a difference or sum in local electrical potential between two or more sites, and refers to a local potential at two or more sites in the nanopore sensor configuration.

Figure 1F:
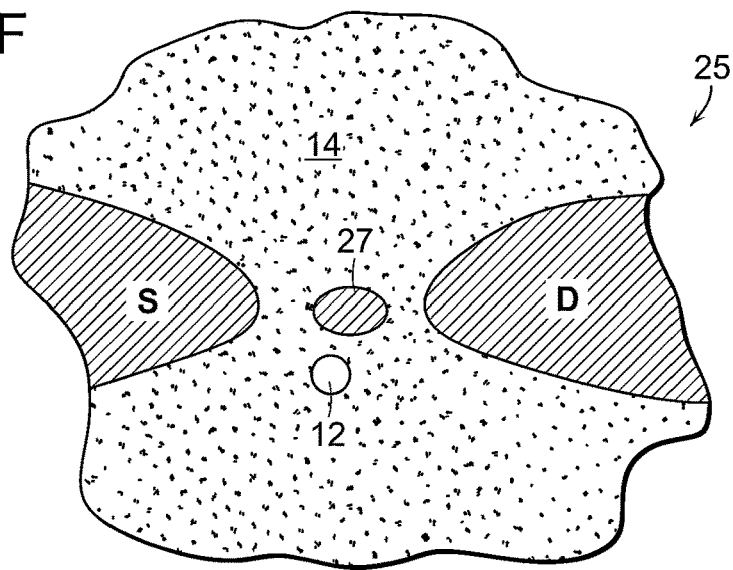
FIG. 1F is a schematic plan view of a single electron transistor implementation of a nanopore sensor configuration for measuring local electrical potential.

The local electrical potential measurement can be made by any suitable device and/or circuit or other transduction element, including biological or other non-solid state transduction elements, and is not limited to the transistor implementation described above. As shown in FIG. 1F, there can be provided a transduction element on the support structure 14 that is configured as a single electron transistor (SET) circuit 27. The source, S, and drain, D, regions of the SET are disposed on the support structure, providing tunneling barriers to the SET 27. In the resulting quantum dot system, the electrical conductance through the SET 27 depends on the energy level of the SET with respect to the Fermi level of the source, S, and drain, D. With the nanopore 12 located in the vicinity of the SET, the electrical potential, and corresponding energy level, of the SET changes as species objects translocate through the nanopore, changing the conductance of the SET circuit.

Figure 1G:
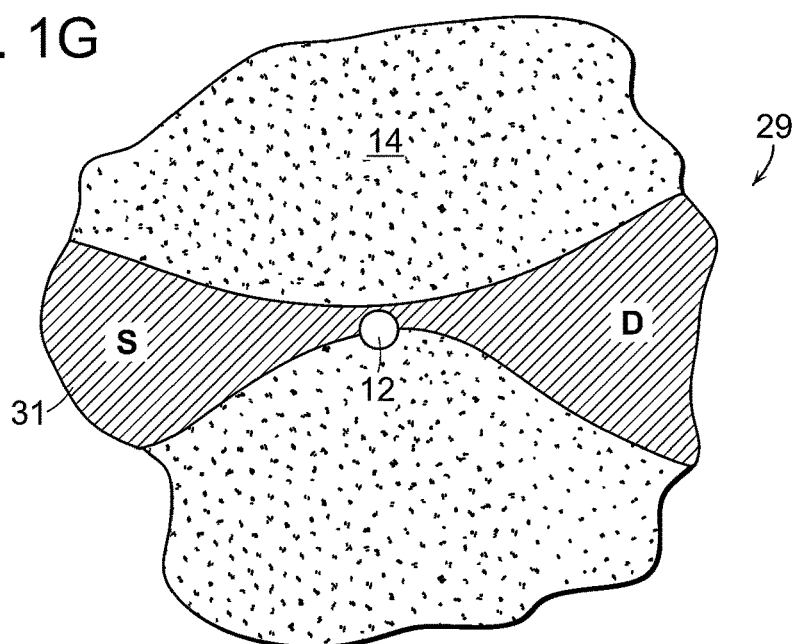
FIG. 1G is a schematic plan view of a quantum point contact implementation of a nanopore sensor configuration for measuring local electrical potential.

Further, as shown in FIG. 1G, there can be provided on the support structure 14 a quantum point contact (QPC) system 29 for making a local electrical potential measurement. In this system, an electrically conductive region 31 is provided that forms source, S, and drain, D, regions that are connected via a very thin conducting channel region at the site of the nanopore 12. The channel region is sufficiently thin that the electronic carrier particle energy states that are perpendicular to the channel region are quantized. As species objects translocate through the nanopore, the local potential around the QPC, thus the Fermi level inside the thin conduction channel region changes, resulting in a change in the number of quantized states below the Fermi level, and a corresponding change in QPC conductance.

A nanowire FET can also be configured at the site of the nanopore. The nanowire can be formed of any suitable electrically conducting or semiconducting material, including fullerene structures and semiconducting wires. The term "nanowire" as used herein refers to an electrical conduction channel that is characterized by a width that is compatible with the signal decay length measured from the nanopore site. The channel width is preferably on the same order of magnitude as the decay length and can be larger. The nanowire can be made from any semiconductor material that is stable in the selected reservoir solution.

Figure 1H:
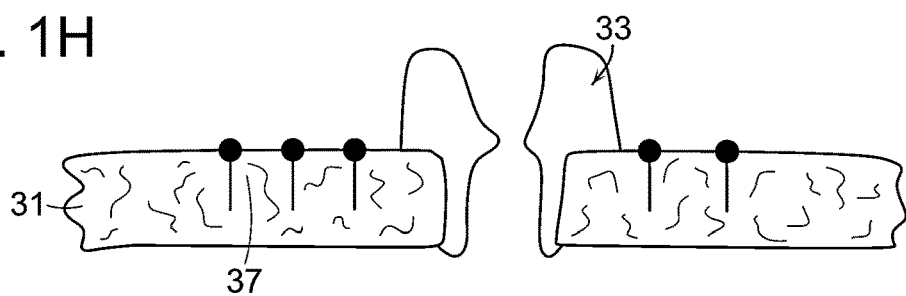
FIG. 1H is a schematic side view of a lipid bilayer including fluorescent dye arranged for implementation of a protein nanopore sensor configuration for measuring local electrical potential.

The nanopore sensor is not limited to solid state nanopore configurations with solid state voltage sensing devices. Biological nanopores and potential sensing arrangements can also be employed, e.g., with a protein nanopore or other suitable configuration. As shown in FIG. 1H, there can be provided an amphiphilic layer 31 in which is disposed a protein nanopore 33. A voltage-sensitive dye, e.g., a fluorescent direct dye 37, can be provided in the lipid bilayer as an electrical transduction element. With this arrangement, when a species object such as a molecule translocates through the protein nanopore, the voltage drop across the amphiphilic layer changes, and the fluorescence of the dye is modulated by the voltage change. Optical detection or sensing of the dye fluorescence and changes to that fluorescence provide sensing of the electrical potential at the nanopore. Optical microscopy or other conventional arrangement can be employed for making this potential measurement as an optical output signal from the nanopore sensor. This amphiphilic layer nanopore sensor is an example of a biological nanopore sensor that is based on sensing of the local potential at a site in the nanopore system. The method of local potential measurement for nanopore translocation detection is not limited to a particular solid state or biological configuration and can be applied to any suitable nanopore configuration.

The support structure can be formed from either or both organic and inorganic materials, including, but not limited to, microelectronic materials, whether electrically conducting, electrically semiconducting, or electrically insulating, including materials such as II-IV and III-V materials, oxides and nitrides, like $Si_3N_4$, $Al_2O_3$, and SiO, organic and inorganic polymers such as polyamide, plastics such as Teflon®, or elastomers such as two-component addition-cure silicone rubber, and glasses. A solid state support structure may be formed from monatomic layers, such as graphene, or layers that are only a few atoms thick such as those disclosed in U.S. Pat. No. 8,698,481, and U.S. Patent Application Publication 2014/174927, both hereby incorporated by reference. More than one support layer material can be included, such as more than one graphene layer, as disclosed in US Patent Application Publication 2013/309776, incorporated herein by reference. Suitable silicon nitride membranes are disclosed in U.S. Pat. No. 6,627,067, and the support structure may be chemically functionalized, such as disclosed in U.S. patent application publication 2011/053284, both hereby incorporated by reference.

For a selected support structure material composition, thickness, and arrangement, any suitable method can be employed for producing a nanopore in the support structure. For example, electron beam milling, ion beam milling, material sculpting with an energetic beam, dry etching, wet chemical or electrochemical etching, or other method can be employed for producing a nanopore, as described, e.g., in U.S. Patent Application Publication 2014/0262820, U.S. Patent Application Publication 2012/0234679, U.S. Pat. Nos. 8,470,408, 8,092,697, 6,783,643, and 8,206,568, all of which are hereby incorporated by reference. In addition, extrusion, self-assembly, material deposition on sidewalls of a relatively large aperture, or other nanopore formation method can be employed.

As an alternative to providing a completely solid state nanopore, a biological nanopore can be provided within a solid state aperture. Such a structure is disclosed for example in U.S. Pat. No. 8,828,211, hereby incorporated by reference. Further, a biological nanopore may be a transmembrane protein pore. The biological pore may be a naturally occurring pore or may be a mutant pore. Typical pores are described in U.S. Patent Application No. 2012/1007802, and are described in Stoddart D et al., Proc Natl Acad Sci, 12; 106(19):7702-7, Stoddart D et al., Angew Chem Int Ed Engl. 2010; 49(3):556-9, Stoddart D et al., Nano Lett. 2010 Sep. 8; 10(9):3633-7, Butler T Z et al., Proc Natl Acad Sci 2008; 105(52):20647-52, U.S. Patent Application Publication 2014/186823, and WO2013/153359, all of which are hereby incorporated by reference. The pore may be homo-oligomeric, namely, derived from identical monomers. The pore may be hetero-oligomeric, namely where at least one monomer differs from the others. The pore may be a DNA origami pore, as described by Langecker et al., Science, 2012; 338: 932-936, hereby incorporated by reference.

In one embodiment the pore can be provided within an amphiphilic layer. An amphiphilic layer is a layer formed from amphiphilic molecules, such as phospholipids, which have both hydrophilic and lipophilic properties. The amphiphilic layer can be a monolayer or a bilayer, with the layer selected from a lipid bilayer or non-natural lipid bilayer. The bilayer can be synthetic, such as that disclosed by Kunitake T., Angew. Chem. Int. Ed. Engl. 31 (1992) 709-726. The amphiphilic layer can be a co-block polymer such as disclosed by Gonzalez-Perez et al., Langmuir, 2009, 25, 10447-10450, and U.S. Pat. No. 6,723,814, both hereby incorporated by reference. The polymer can be, e.g., a PMOXA-PDMS-PMOXA triblock copolymer.

Figure 2A:
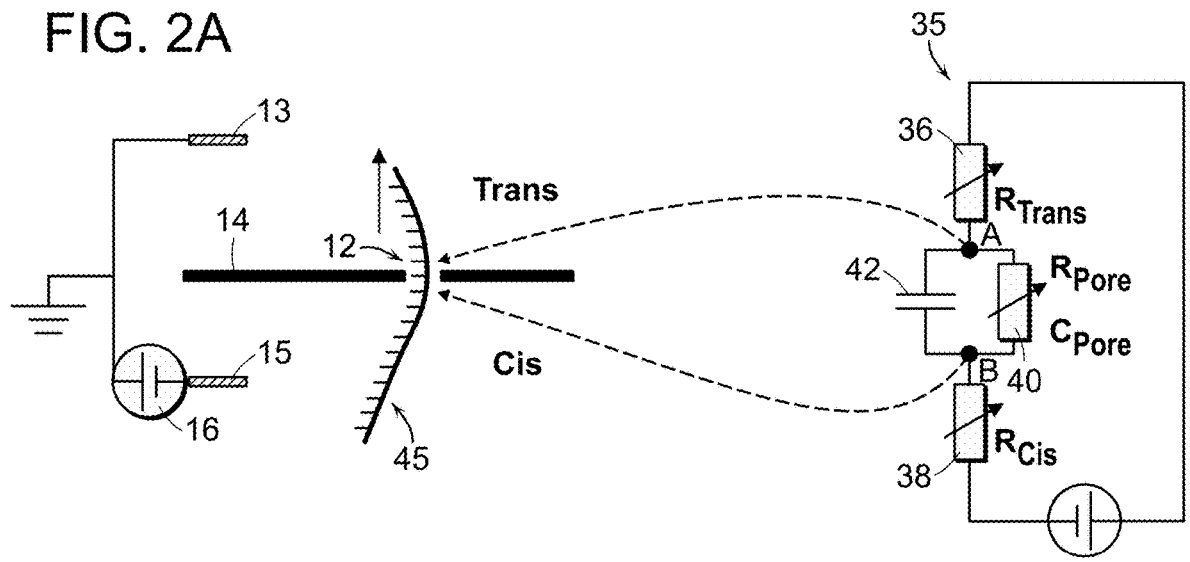
FIG. 2A is a schematic diagram and corresponding circuit elements for a nanopore sensor configuration for measuring local electrical potential.

Referring to FIG. 2A, any of these support structures, nanopores, and electrical configurations for measuring the local electrical potential at one or more sites in a nanopore sensor can be employed in a method for sensing the translocation of species through the nanopore. To explain the principle of this sensing, it is instructive to model the nanopore sensor as a circuit 35 including electrical components corresponding to physical elements of the sensor, as shown in FIG. 2A. The cis and trans reservoirs can each be modeled with a characteristic fluidic access resistance, $R_{Trans}$, 36, $R_{Cis}$, 38. This access resistance is defined for this analysis as the fluidic resistance in a reservoir solution local to the site of the nanopore, not in the bulk solution away from the nanopore. The nanopore can be modeled with a characteristic nanopore solution resistance, $R_{Pore}$, 40 that is the fluidic resistance of solution through the length of the nanopore between the two sides of the support structure in which the nanopore is disposed. The nanopore can also be modeled with a characteristic capacitance $C_{Pore}$, that is a function of the membrane or other support structure in which the nanopore is disposed. The access resistance of both chambers and the nanopore solution resistance are variable.

In a nanopore sensor starting condition in which no species are translocating the nanopore, the nanopore can be characterized by the solution resistance, $R_{Pore}$, given above, and both fluidic reservoirs can be characterized by the access resistances of the trans reservoir and the cis reservoir, $R_{Trans}$ and $R_{Cis}$, respectively. Then when a species object, such as a biological molecule 45, translocates the nanopore 12 as shown in FIG. 2A, the solution resistance, $R_{Pore}$, of the nanopore and the access resistances, $R_{Trans}$ and $R_{Cis}$, of each of the reservoirs, change because the molecule in the nanopore at least partially blocks the passageway through the nanopore length, changing the effective diameter of the nanopore. With such a blockage, the fluidic solution resistance of the nanopore and the access resistance of both reservoirs increase above the resistance of the nanopore and access resistance of both reservoirs with no molecule present in the nanopore.

The partial blockage of the nanopore by a species object effects the nanopore solution resistance and the reservoir access resistances differently, as explained in detail below. As a result, the partial blockage of the nanopore by a translocating species causes a corresponding redistribution of electrical voltage occurs between the nanopore and the cis and trans reservoirs solutions, and the electrical potential at sites throughout the nanopore sensor accordingly adjusts. The local electrical potential at both the sites denoted as A and B in FIG. 2A thereby changes accordingly with this change in nanopore solution resistance and redistribution of voltage between the reservoir solutions and the nanopore. A measurement of electrical potential at either of these sites, or at another site of the nanopore sensor configuration, or a measurement of a difference in local potential between two or more sites, thereby provides an indication of the translocation of the molecule through the nanopore.

The local electrical potential at a selected nanopore sensor site and changes in this potential can be sensed by an electrical transduction element disposed in the nanopore sensor. For example, changes in the conductance of the conducting channel in a transistor device can provide an electrical potential measurement. Transistor channel conductance therefore can be employed as a direct indication of the electrical potential local to the physical location of the transistor channel. The nanopore sensor arrangements of FIGS. 1A-1B correspond to a local electrical potential measurement at site A in the circuit 35 of FIG. 2A. The nanopore sensor arrangements of FIG. 1C-1D correspond to a local electrical potential measurement at site B in the circuit 35 of FIG. 2A. The nanopore sensor arrangement of FIG. 1E corresponds to a local electrical potential measurement at both sites A and B in the circuit 35 of FIG. 2A, and enables a determination of the difference between the potential at those two sites.

Figure 2B:
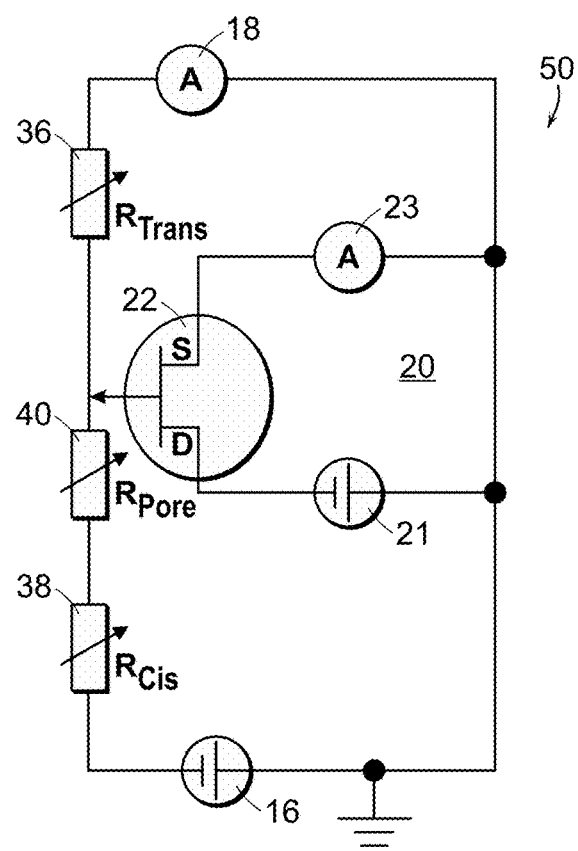
FIG. 2B is a circuit diagram for the nanopore sensor transistor implementation of FIG. 1B.

An electrical circuit equivalent of the example configuration of FIG. 1B is shown in FIG. 2B. Here is represented the access resistances of the cis and trans reservoirs, $R_{Cis}$, $R_{Trans}$, respectively, and the fluidic solution resistance, $R_{Pore}$, of the nanopore. The location of an electrical transduction element for measuring local potential, e.g., the channel of a transistor 22, is here positioned at the site A in FIG. 2A, providing a local electrical potential indication in the trans reservoir at the trans reservoir side of the nanopore. With this arrangement, as species objects such as molecules translocate through the nanopore, the output signal of the electrical potential measurement circuit can be monitored for changes in electrical potential, corresponding to changes in the state of the nanopore and the presence or absence of one or more objects in the nanopore.

This analysis can be applied to any nanopore sensor in which there is provided a local electrical transduction element. The analysis is not limited to the FET and other implementations described above, and is applicable to any suitable arrangement for any transduction element. All that is required is the provision of an electrical transduction element, such as a device, region of a device, circuit, or other transduction element that makes a local electrical potential measurement as species objects translocate the nanopore.

Figure 3A:
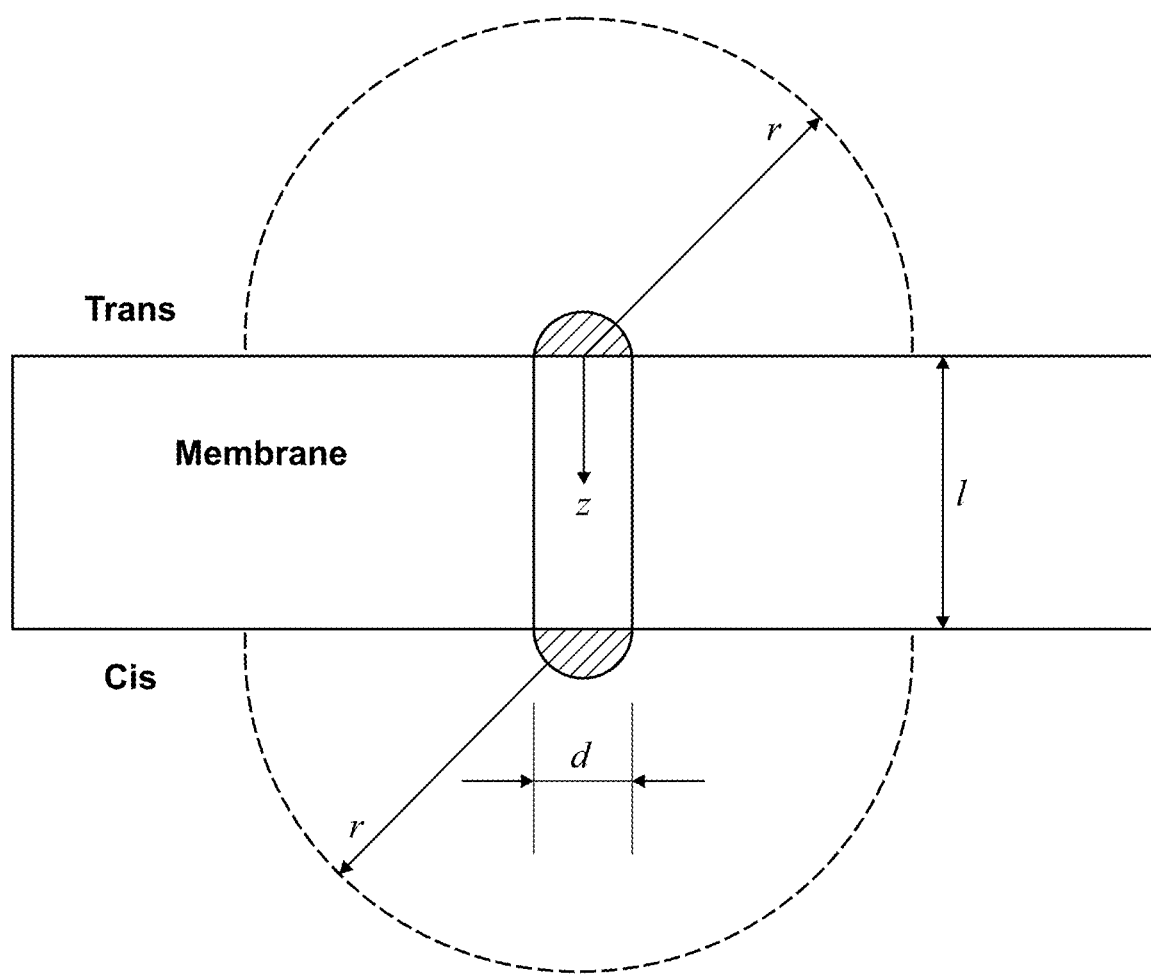
FIG. 3A is a schematic side view of the geometric features of a nanopore sensor configuration for measuring local electrical potential as-defined for quantitative analysis of the sensor.
Figure 3C:
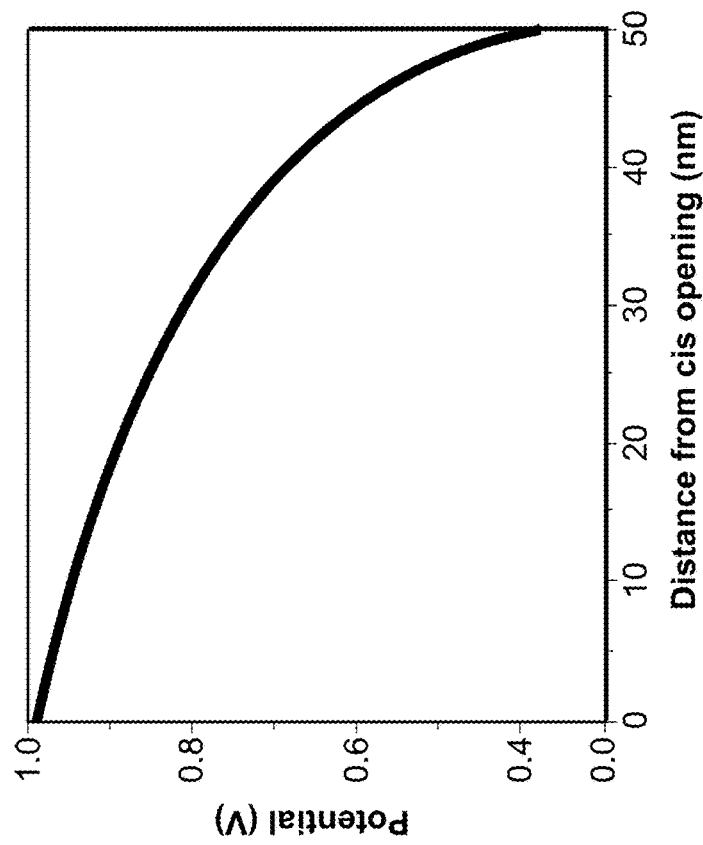
FIGS. 3B-3C are plots of the electrical potential in a nanopore of a nanopore sensor for measuring local electrical potential, here plotted as a function of distance from the nanopore into the cis reservoir, for a configuration in which the cis and trans reservoirs include fluidic solutions of equal ionic concentration and for a configuration in which the cis and trans reservoirs include fluidic solutions of unequal ionic concentration, respectively.
Figure 3B:
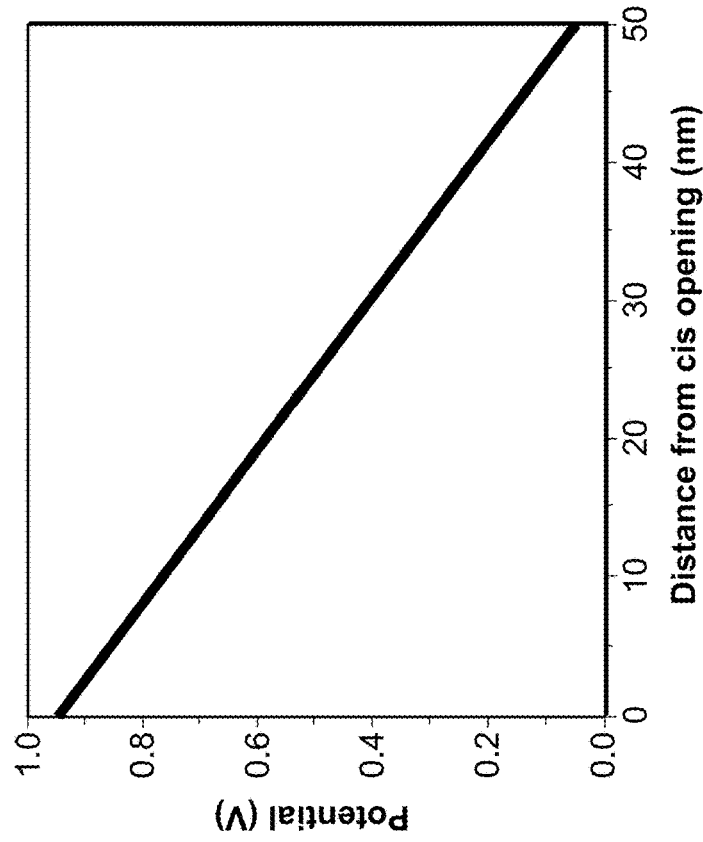
Figure 3E:
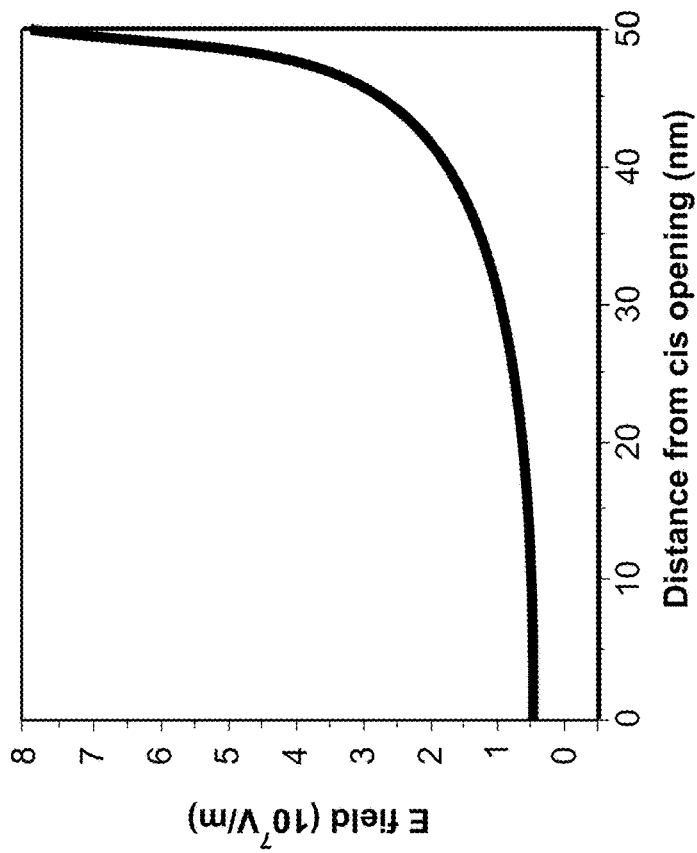
FIGS. 3D-3E are plots of the electrical field in a nanopore of a nanopore sensor for measuring local electrical potential, corresponding to the plots of electrical potential of FIGS. 3A-3B, respectively.

To further analyze the nanopore sensor system parameters, the nanopore sensor can be modeled as shown in the schematic representation of FIG. 3A. Several assumptions can be employed to enable an analytical calculation. First, geometrical changes of the nanopore support structure, such as a membrane, as well as the nanopore itself, and other regions of the nanopore sensor, caused by the inclusion of a local potential sensing transduction element can be ignored and the potential sensing transduction element can be modeled as a point potential detector. The fluidic reservoirs are assumed to include electrically conductive ionic solutions. The two reservoir solutions are specified to include distinct ionic concentrations that may be differing ionic concentrations. In one analysis, with differing ionic concentrations specified for the reservoirs, the ionic concentration distribution through the nanopore system is determined by the steady state diffusion that is driven by the cis/trans reservoir concentration difference; the diffusion is assumed to reach steady state. A further assumption can be made by approximating the buffer concentration distribution and electrical potential as being constant in small hemispheres on both sides of the nanopore. The nanopore sensor is assumed to be in steady state. Under these conditions, the diffusion equations of the nanopore sensor are given as:

$$\begin{cases} \frac{\partial C}{\partial t} = 0 & \text{(For both chambers and inside the nanopore)} \\ r\frac{\partial^2 C(r)}{\partial r^2} + 2\frac{\partial C(z)}{\partial z} = 0 & \text{(For both chambers)} \\ \frac{\partial C(z)}{\partial z} = const & \text{(Inside the nanopore)} \end{cases} \quad (1)$$

Where Cis fluidic ion concentration, t is time, r is location in a reservoir at a point measured from the nanopore, and z is distance through the nanopore length. If these diffusion equations are solved under the boundary conditions that in the cis reservoir far away from the nanopore, $C=C_{Cis}$, in the trans reservoir far away from the nanopore, $C=C_{Trans}$, the flux is the same in the nanopore and for both reservoirs, and the concentration is continuous at the nanopore opening in each reservoir, then the ionic concentration of the two reservoirs and the nanopore can be given as:

$$\begin{cases} C_C(r) = C_{Cis} - \frac{C_{Cis} - C_{Trans}}{4(2l+d)} \frac{d^2}{r} & \text{(Cis chamber)} \\ C_T(r) = C_{Trans} - \frac{C_{Trans} - C_{Cis}}{4(2l+d)} \frac{d^2}{r} & \text{(Trans chambers)} \\ C_P(r) = C_{Trans} + \frac{C_{Cis} - C_{Trans}}{2(2l+d)}(4z+d) & \text{(Nanopore)} \end{cases} \quad (2)$$

Here l and d are thickness of the nanopore support structure and nanopore diameter, respectively. Because the ionic concentration distribution is therefore known and the solution conductivity is proportional to the concentration, then the conductivity of solution, σ, is given as:

$$\sigma = \Sigma \cdot C. \quad (3)$$

Here Σ is the molar conductivity of solution. Assuming the total current is I, then the electrical potential drop through the nanopore sensor, with a cis reservoir voltage, $V_C$, a trans reservoir voltage, $V_T$, and a nanopore voltage, $V_P$, can be given as:

$$\begin{cases} dV_C(r) = \frac{Idr}{2\pi\Sigma C_C(r)r^2} & \text{(Cis chamber)} \\ dV_T(r) = \frac{-Idr}{2\pi\Sigma C_T(r)r^2} & \text{(Trans chambers)} \\ dV_P(r) = \frac{4Idz}{\pi\Sigma C_P(z)d^2} & \text{(Nanopore)} \end{cases} \quad (4)$$

If these three equations are solved with boundary conditions specifying that far away from nanopore in the cis reservoir the electrical potential equals the voltage applied across the structure or membrane, i.e., a transmembrane voltage (TMV), to electrophoretically drive an object through the nanopore, and that far away from nanopore in the trans chamber, the potential is 0 V, then the voltages in the nanopore sensor, namely, the voltage in the cis reservoir, $V_C(r)$, the voltage in the trans reservoir, $V_T(r)$, and the voltage in the nanopore, $V_P(r)$, are given as:

$$\begin{cases} V_C(r) = V + \frac{2I(2l+d)}{\pi\Sigma(C_{Cis} - C_{Trans})d^2} \ln\left(1 - \frac{(C_{Cis} - C_{Trans})d^2}{4(2l+d)C_{Cis}r}\right) \\ V_T(r) = \frac{2I(2l+d)}{\pi\Sigma(C_{Cis} - C_{Trans})d^2} \ln\left(1 + \frac{(C_{Cis} - C_{Trans})d^2}{4(2l+d)C_{Trans}r}\right) \\ V_P(r) = \frac{2I(2l+d)}{\pi\Sigma(C_{Cis} - C_{Trans})d^2} \ln\left(\frac{(4l+d)C_{Trans} + dC_{Cis} + 4(C_{Cis} - C_{Trans})z}{2(2l+d)C_{Trans}}\right) \end{cases} \quad (5)$$

Because the electrical potential is continuous at both nanopore openings into the reservoirs and because the total voltage applied is V, Expression (5) can be further simplified to:

$$\begin{cases} V_C(r) = V + \frac{V}{\ln(C_{Cis}/C_{Trans})} \ln\left(1 - \frac{d^2(1 - C_{Trans}/C_{Cis})}{4(2l+d)r}\right) \\ V_T(r) = \frac{V}{\ln(C_{Cis}/C_{Trans})} \ln\left(1 + \frac{d^2(1 - C_{Cis}/C_{Trans}-1)}{4(2l+d)r}\right) \\ V_P(r) = \frac{V}{\ln(C_{Cis}/C_{Trans})} \ln\left(\frac{(4l + d + dC_{Cis}/C_{Trans} + 4(C_{Cis}/C_{Trans} - 1)z}{2(2l+d)}\right) \end{cases} \quad (6)$$

With this expression, the electric field, $E_P(r)$ inside nanopore can be given as:

$$E_P(r) = \frac{dV_P(r)}{dz} = \quad (7)$$

$$\frac{4V(C_{Cis}/C_{Trans} - 1)}{\ln(C_{Cis}/C_{Trans})} \cdot \frac{1}{4l + d + dC_{Cis}/C_{Trans} + 4(C_{Cis}/C_{Trans} - 1)z}.$$

With this expression, the electrical potential change at the trans reservoir side of the nanopore can be estimated by the electrical potential change due to a reduction in the nanopore area, A, by the presence of a species object, such as a molecule, in the nanopore, as:

$$\delta V_T|_{d/2} = \frac{\partial V_T}{\partial A}\bigg|_{d/2} \delta A = \frac{2\delta AV}{\pi \ln(C_{Cis}/C_{Trans})} \frac{(4l+d)(C_{Cis}/C_{Trans}-1)}{(2l+d)(d^2(C_{Cis}/C_{Trans}-1)+4(2l+d)r}\bigg|_{d/2} = \quad (8)$$

$$\frac{2\delta AV}{\pi \ln(C_{Cis}/C_{Trans})} \frac{(4l+d)(C_{Cis}/C_{Trans}-1)}{(2l+d)(d^2(C_{Cis}/C_{Trans}+1)+4ld)}$$

Here $\delta A$ is the cross-sectional area of the molecule. The resistances of the nanopore sensor, namely, $R_{Cis}$, $R_{Trans}$, and $R_{Pore}$, can be computed based on the above expressions for voltage drop across the reservoirs and the nanopore as:

$$\begin{cases} R_{Cis} = \frac{-2(2l+d)}{\pi\Sigma(C_{Cis}-C_{Trans})d^2} \ln\left(1 - \frac{(C_{Cis}-C_{Trans})d}{2(2l+d)C_{Cis}}\right) \\ R_{Trans} = \frac{2(2l+d)}{\pi\Sigma(C_{Cis}-C_{Trans})d^2} \ln\left(1 + \frac{(C_{Cis}-C_{Trans})d}{2(2l+d)C_{Trans}}\right) \\ R_{Pore} = \frac{2(2l+d)}{\pi\Sigma(C_{Cis}-C_{Trans})d^2} \ln\left(\frac{(4l+d)C_{Cis}+dC_{Trans}}{(4l+d)C_{Trans}+dC_{Cis}}\right) \end{cases} \quad (9)$$

So, the total resistance and ionic current of the nanopore sensor are given as:

$$\begin{cases} R = R_{Cis} + R_{Trans} + R_{Pore} = \frac{2(2l+d)}{\pi\Sigma(C_{Cis}-C_{Trans})d^2} \ln\left(\frac{C_{Cis}}{C_{Trans}}\right) \\ I = V/R = \frac{\pi\Sigma(C_{Cis}-C_{Trans})d^2 V}{2(2l+d)\ln(C_{Cis}-C_{Trans})} \end{cases} \quad (10)$$

With these expressions, it is demonstrated that the electrical characteristics of the nanopore sensor, and in particular the distribution of electrical potential in the sensor, depends directly on the ionic concentration of the fluidic solutions in the cis and trans reservoirs. Specifically, the ratio of the reservoir solution concentrations directly impacts the magnitude of the change in local potential due to species translocation of the nanopore.

FIGS. 3B-3E are plots of electrical potential and electric field in the nanopore, demonstrating these conditions. Given a cis/trans buffer solution concentration ratio=1:1, a 50 nm-thick nitride membrane, a 10 nm diameter nanopore in the membrane, and a 1 V transmembrane voltage, i.e., 1 V applied between the solutions in the two reservoirs, then the electrical potential in the nanopore as a function of distance from the nanopore opening at the cis reservoir is plotted in FIG. 3B, based on Expression (6) above. That same potential is plotted in FIG. 3C for a condition in which the cis/trans buffer solution concentration ratio is instead 100:1. Note the increase in electrical potential at a given nanopore location for the unbalanced buffer solution ratio at points closer to the lower-concentration reservoir.

Figure 3D:
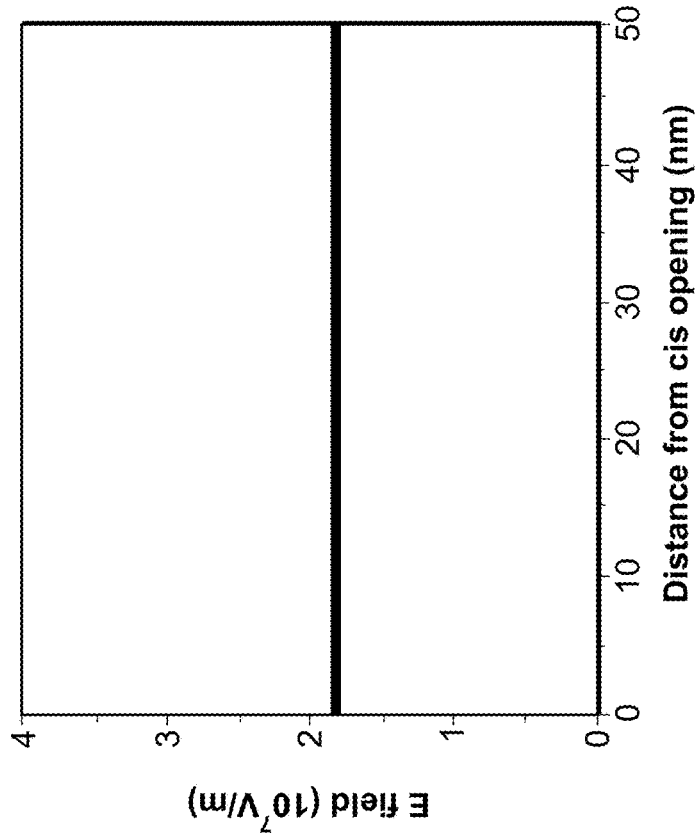

FIG. 3D is a plot of the electric field in the nanopore under the conditions given above, here for a balanced buffer solution ratio, based on Expression (7) above. That same electric field profile is plotted in FIG. 3E for a condition in which the cis/trans buffer solution concentration ratio is instead 100:1. Note the increase in electrical potential at a given nanopore location for the unbalanced buffer solution ratio, and that the electric field is dramatically stronger at points closer to the low concentration, higher resistance, reservoir.

With this finding, it is discovered that with a condition in which the reservoir solutions are both provided as electrically-conductive ionic solutions of the same ionic concentration, the ratio of the access resistance of the cis reservoir, $R_{Cis}$, the access resistance of the trans reservoir, $R_{Trans}$, and the solution resistance of the nanopore, $R_{Pore}$, are all fixed and the nanopore resistance is much larger than the reservoir access resistances. But under non-balanced ion concentration conditions, the reservoir having a lower ionic concentration has a larger access resistance, that can be on the order of the nanopore resistance, while the higher-ionic concentration reservoir resistance becomes comparably negligible.

Based on a recognition of this correspondence, it is herein discovered that to maximize a local potential measurement in the nanopore sensor, in one embodiment, the ionic reservoir solutions can be provided with differing ion concentrations. With this configuration of unbalanced ionic concentration, the local potential measurement is preferably made at a site in the reservoir which includes the lower ionic concentration. It is further preferred that the buffer concentration of the lower-ion concentration solution be selected to render the access resistance of that reservoir of the same order of magnitude as the nanopore resistance and much larger than the resistance of the high-ion concentration solution, e.g., at least an order of magnitude greater than that of the high-ion concentration solution, so that, for example, if the local potential measurement is being made in the trans reservoir:

$$R_T, R_P \gg R_C \quad (11)$$

Based on this discovery then, for a given nanopore diameter, which sets the nanopore resistance, $R_P$, it is preferred in one embodiment to decrease the ionic solution buffer concentration of the reservoir designated for local potential measurement to a level at which the access resistance of that reservoir is of the same order of magnitude as the nanopore resistance. This reservoir access resistance should not dominate the nanopore sensor resistance, but should be on the order of the nanopore resistance.

Figure 4A:
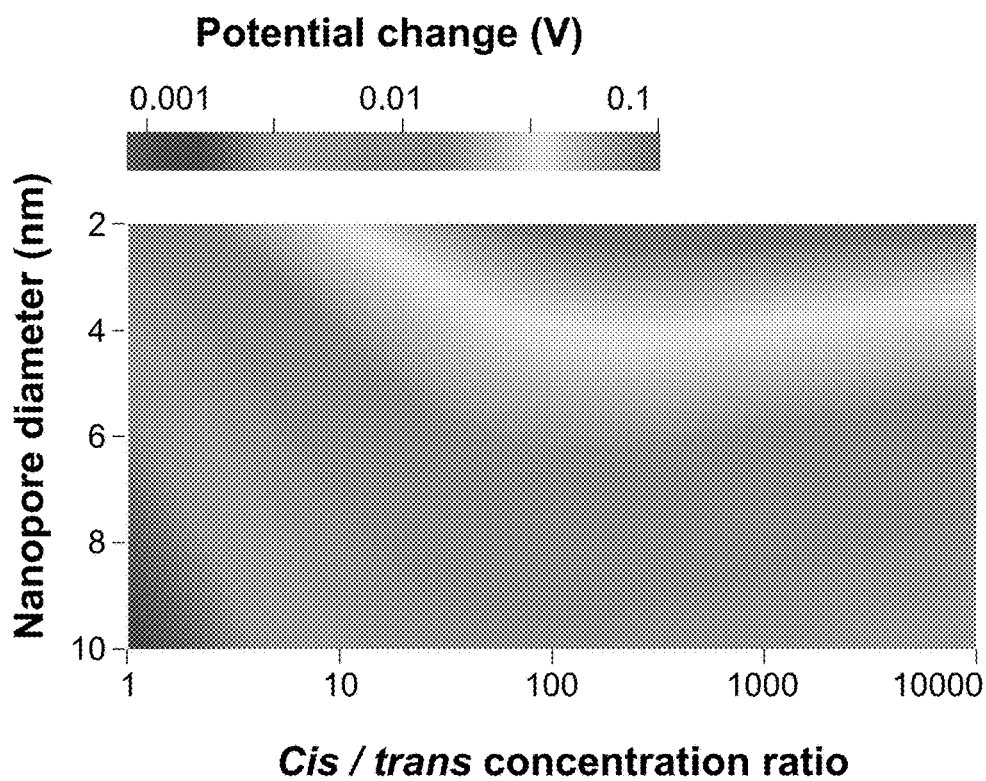
FIG. 4A is a plot of the change in potential in a nanopore for a 50 nm-thick nanopore membrane and a configuration of a 1 V transmembrane voltage (TMV) for electrophoretic species translocation as a dsDNA molecule translocates through the nanopore, as a function of the $C_{Cis}/C_{Trans}$ ionic concentration ratio for various nanopore diameters below 10 nm where the nanopore is configured for local electrical potential measurement.
Figure 4B:
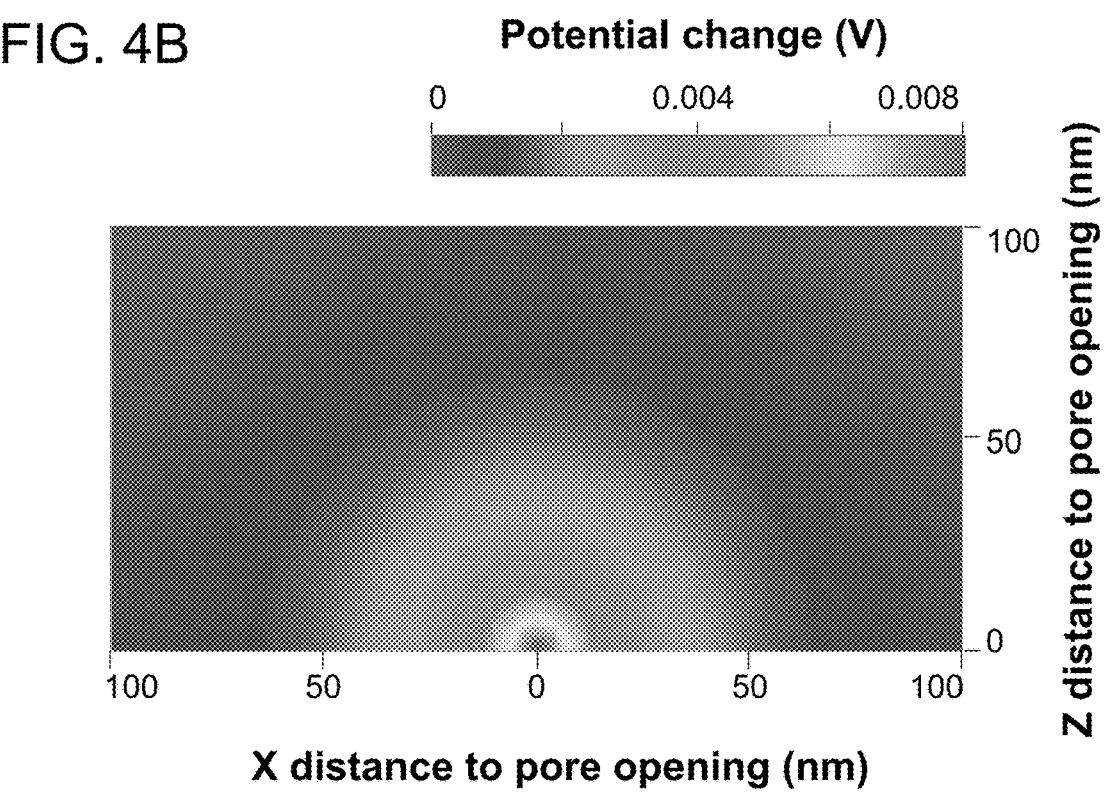
FIG. 4B is a plot of the change in potential in the trans reservoir for a 10 nm-diameter nanopore at 1 V TMV for the conditions of the plot of FIG. 4A.

This condition can be quantitatively determined directly by electrically modelling the nanopore sensor components in the manner described above. Based on Expression (8) above, there can be determined the ratio of solution concentrations that maximize the potential change during nanopore translocation of a selected object for given nanopore sensor parameters. FIG. 4A is a plot of Expression (8) for a 50 nm-thick nanopore membrane and a configuration of a 1 V TMV for electrophoretic species translocation as a dsDNA molecule translocates through the nanopore. The potential change is shown as a function of the $C_{Cis}/C_{Trans}$ ionic concentration ratio for various nanopore diameters below 10 nm. From this plot, it is found that the local potential change in the trans reservoir is maximized for a ~100:1 $C_{Cis}/C_{Trans}$ chamber buffer concentration ratio for any nanopore diameter modelled here. FIG. 4B is a plot of the corresponding calculated potential change distribution in the trans reservoir for a 10 nm-diameter nanopore at 1 V TMV for the selected 100:1 $C_{Cis}/C_{Trans}$ solution concentration ratio.

This demonstrates that based on the discovery herein, in one embodiment, for a given reservoir site that is selected for making electrical potential measurements, the ratio of ionic fluid buffer concentration in the two reservoirs can be selected with the lower buffer concentration solution in the measurement reservoir, to maximize the amplitude of the electrical potential changes at that selected measurement site. The distribution of this resulting potential change is highly localized within several tens of nanometers of the nanopore, as shown in FIG. 4B. For the 100:1 $C_{Cis}/C_{Trans}$ solution concentration ratio and nanopore parameters given just above, it can be determined, e.g., based on Expression (9) above, that the access solution resistance of the trans reservoir and the solution resistance of the nanopore are indeed within the same order of magnitude.

With this arrangement of reservoir fluidic solution buffer concentrations and potential measurement configuration, it is noted that the local potential sensing technique produces a local potential measurement signal that depends on the trans-membrane voltage (TMV) and the ionic current signal. Other sensor based nanopore technologies generally rely on a direct interaction between a translocating species and the nanopore sensor through, e.g., electrical coupling or quantum mechanical tunnelling. For these techniques, the nanopore output signal is typically not directly related to the TMV or ionic current and should not change significantly when the TMV is changed. In contrast, in the local potential measurement system herein, the nanopore sensor signal is proportional to the TMV and can be regarded as a linear amplification of the ionic current signal. As a result, both the local potential measurement signal and the ionic current signal amplitudes depend on the TMV linearly, but the ratio between them is a constant for a given nanopore geometry and reservoir solution concentrations, as evidenced by the expressions given above.

An advantage of the local potential measurement method is the characteristically high-bandwidth capability of the measurement with low noise. Low signal bandwidth is one of the issues that limits direct nanopore sensing by the conventional ionic current blockage measurement technique, due to the difficulties of high bandwidth amplification of very small measured electrical current signals. This can be particularly true for a small nanopore when employed for DNA sensing. In the local potential sensing method, a large local electrical potential signal is measured instead of a small current signal, so the signal bandwidth is not limited by the capabilities of a current amplifier. As a result, high-bandwidth signal processing electronics can be integrated on a solid state nanopore sensing structure.

Further, except for intrinsic shot noise and Johnson noise, the majority of noise contributions to an ionic current blockage measurement technique are introduced through the capacitive coupling cross a nanopore membrane and this capacitive coupling component of noise can be overwhelming at certain stages of nanopore operation. Conventionally, a very small membrane area exposure to a reservoir solution is required in an effort to minimize noise. In the local potential measurement method herein, because the local potential signal decays within a few tens of nanometers around the nanopore for reasonable reservoir concentration ratios, the local potential measurement signal is only affected by capacitive coupling between reservoir solutions within this local volume. Therefore, the majority of capacitive coupling noise is automatically rejected in the local electrical potential measurement sensing method.

Figure 4C:
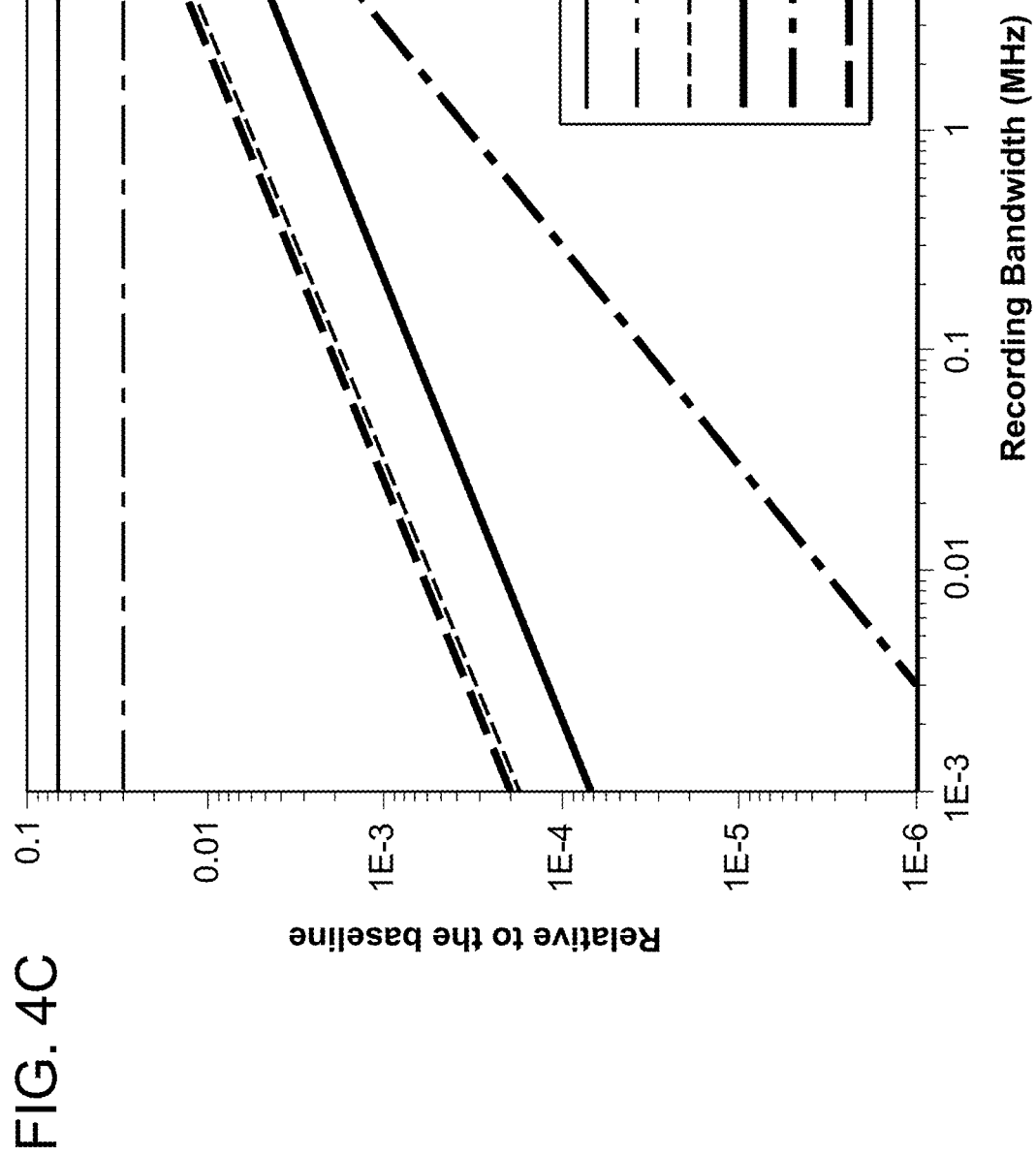
FIG. 4C is a plot of noise sources and signal as a function of recording bandwidth for a nanopore sensor configured for local electrical potential measurement.
Figure 4D:
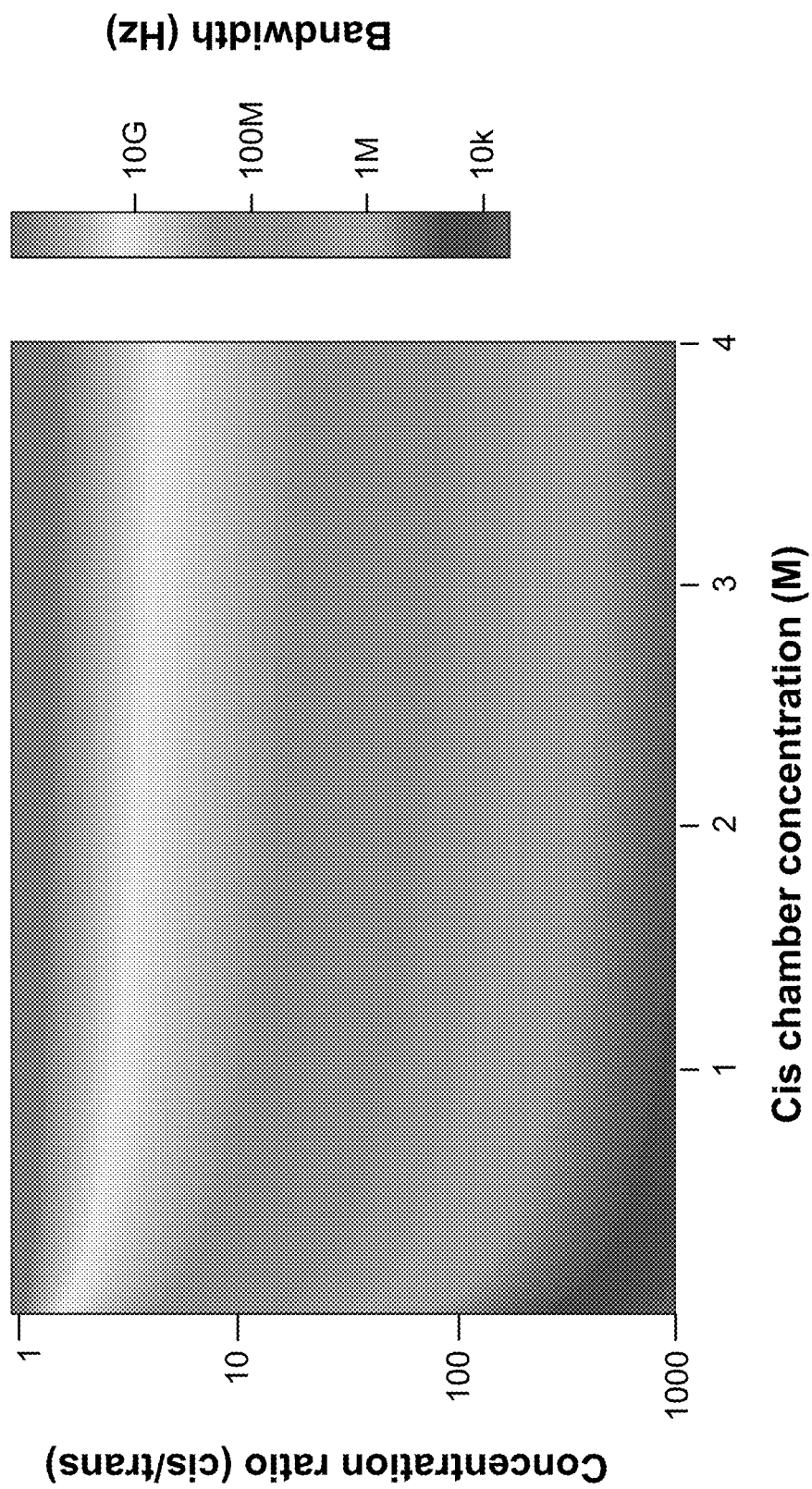
FIG. 4D is a plot of the bandwidth of a nanopore sensor configured for local electrical potential measurement as a function of cis chamber solution concentration for a range of reservoir solution concentration ratios.

Referring to FIGS. 4C-4D, the reservoir buffer solution concentration ratio can be selected, in one embodiment, to optimize the signal bandwidth of the nanopore sensor. Given that the local potential measurement is to be made on one side of the nanopore, say the trans side of the nanopore, then the cis reservoir solution concentration is set as high as reasonable, e.g., about 4 M, about a saturated solution, to minimize the nanopore solution resistance. Then, the signal noise as a function of bandwidth is analyzed, e.g., based on the plot of FIG. 4C. Here are plotted the various contributions to noise as well as the signal expected for a fluidic nanopore operation. The plot labelled "free space" refers to a computation based on free-space molecular size. The plot labelled "Bayley" refers to computation based on molecular size from previous work by Bayley et al, in J. Clarke et al., "Continuous Base Identification for Single-Molecule Nanopore DNA Sequencing," *Nature Nanotechnology*, N. 4, pp. 265-270, 2009. The two signal lines are the minimum signal difference that is attained between the four DNA bases, which minimum signal exists between the A and the T bases. Here the nanopore is given as a 1 nm-diameter nanopore in a graphene membrane, with a 4 M cis reservoir solution concentration, a buffer concentration ratio between the reservoirs of 50:1, and a voltage noise density of about $10^{-9}$ V/√Hz. The dielectric loss factor for graphene is unknown, so 1 was used for convenience. Finding the cross point of the signal and total noise in the plot sets the 1:1 signal-to-noise ratio (S/N). This is the highest possible signal bandwidth. For example, for the fluidic nanopore operation, the 1:1 S/N ratio is at a bandwidth of about 100 MHz. A bandwidth greater than about 50 MHz can be preferred as well as the 100 MHz bandwidth.

Referring to the plot of FIG. 4D, the 100 MHz bandwidth corresponds to reservoir solution concentration ratio of about 50:1, where the local potential is to be made in the low-concentration reservoir side of the nanopore. For the nanopore sensor parameters used in this example, any reservoir concentration ratio higher than about 50:1 will decrease the bandwidth. Any concentration ratio lower than about 50:1 will decrease the signal-to-noise ratio. Therefore, it is discovered herein that the bandwidth can be optimized and there exists an optimization point of reservoir concentration ratio, say 50:1. The reservoir solution concentration ratio therefore can be selected, in one embodiment, based on a trade-off between the characteristic noise of the nanopore sensor and the desired operational bandwidth of the nanopore sensor. It is to be recognized therefore that to minimize noise, the reservoir solution concentration ratio can be increased, but that the bandwidth may be correspondingly reduced. Alternatively, electronic signal processing, such as low-pass filtering, or other processing of the signal, can be employed.

It is further to be recognized that in general, a nanopore of smaller diameter produces a larger signal for a given species object to translocate through the nanopore. For applications such as sensing a particular molecule, like DNA, however, the nanopore extent is preferably based on the molecule extent, and the tuning of the reservoir concentration ratio is made accordingly.

Figure 4E:
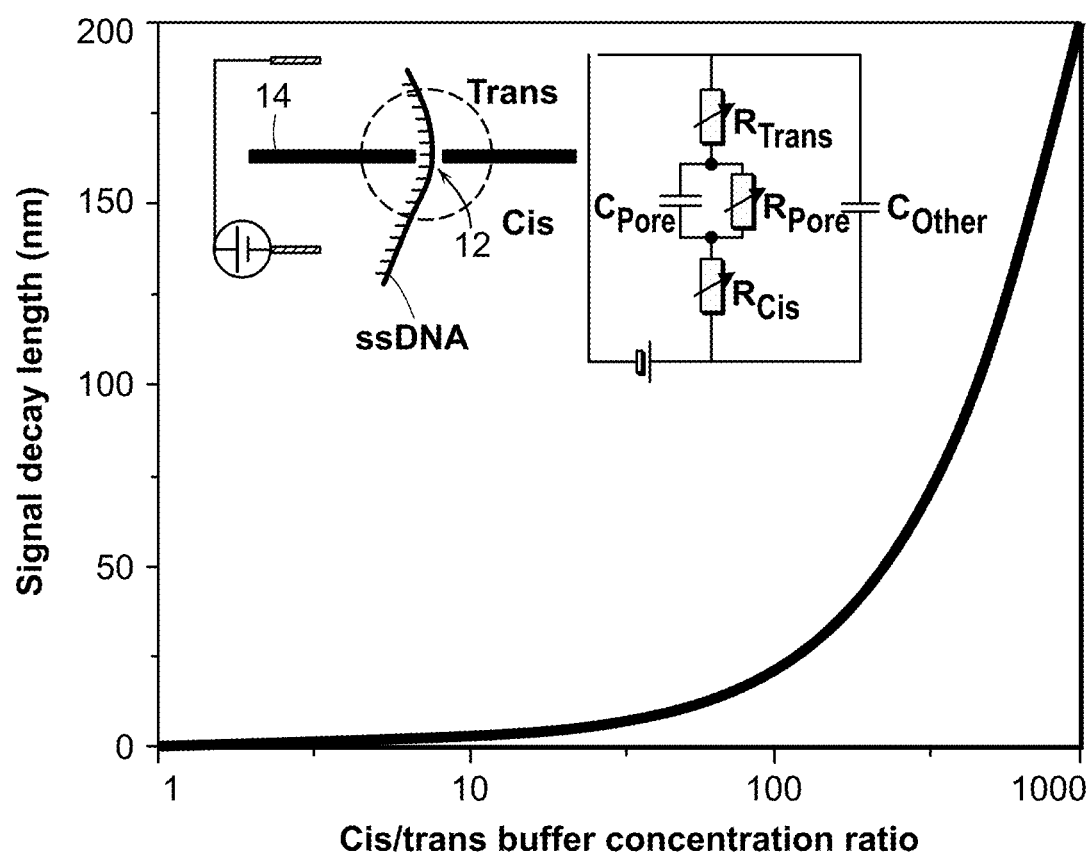
FIG. 4E is a plot of signal decal length from the nanopore site in a nanopore configured for local electrical potential measurement as a function of cis and trans reservoir solution concentration ratio.

The reservoir buffer solution concentration ratio can also be selected, in a further embodiment, to produce a signal decay length, measured from the site of the nanopore, that accommodates a selected local potential measurement device. It is recognized that the decay length of the signal should be sufficiently large to accommodate the arrangement of a potential measurement device within the decay length. FIG. 4E is a plot of signal decay length for a range of buffer concentration ratios, given that the local potential measurement is to be made on the trans reservoir side of the nanopore. The plot is based on the circuit model shown inset in the plot.

Based on this analysis, it is shown that at concentration ratios greater than about 20 or 30, there is produced a sufficient signal decay length to accommodate a device that can measure the local electrical potential within the decay length. At concentration ratios greater than about 50:1, ample decay length is provided for making a potential measurement within the decay length. A signal decay length greater than about 5 nm can be preferred, as well as a signal decay length of, e.g., about 10 nm and about 20 nm.

This particular embodiment with a nanopore sensor analysis for specifying the relative cis and trans solution ionic concentrations is based on a consideration of the changes in nanopore resistance and reservoir access resistances that are caused by species translocation through a nanopore. The methodology herein provides a further analysis, methods, and structures that additionally consider changes in the resistance of the cis and trans reservoir fluids away from the immediate vicinity of the nanopore during species translocation.

Figure 5:
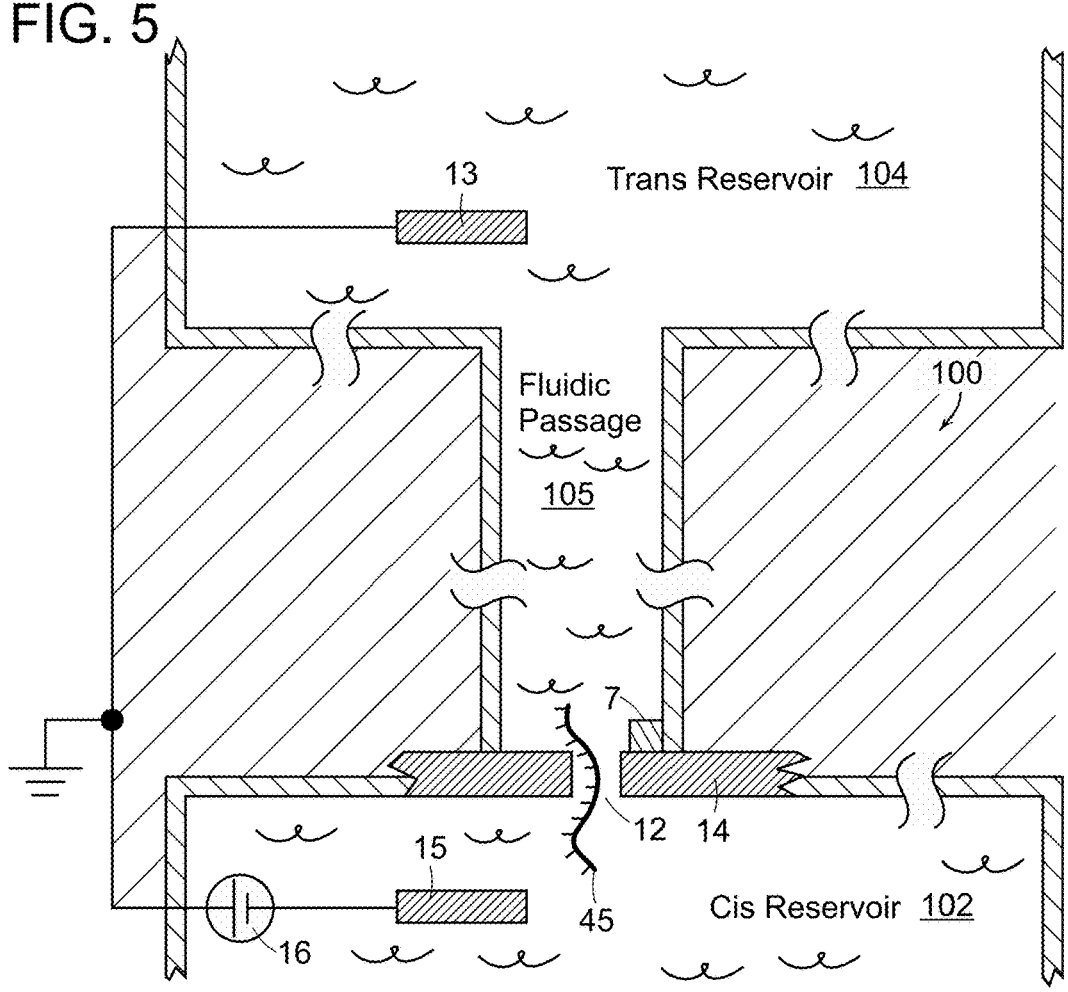
FIG. 5 is a schematic view of a nanopore sensor including a fluidic passage connected between a first reservoir, here the trans reservoir, and a nanopore in a support structure.

Referring to FIG. 5, in this further embodiment, there is schematically shown a nanopore sensor 100 provided herein, the nanopore sensor 100 including a cis reservoir 102 and a trans reservoir 104 on opposing sides of a nanopore 12 that is disposed in a support structure 14. The nanopore must be traversed in a path of fluidic communication between the two reservoirs. A fluidic passage 105 is disposed between one reservoir, here shown as the trans reservoir, and the nanopore 12 to fluidically connect that reservoir to the nanopore through the fluidic passage. The fluidic passage has a passage length that is greater than passage cross-sectional extent, width, or diameter, and is connected to enable fluidic communication between the nanopore and the reservoir to which the passage leads. The second reservoir, here the cis reservoir, is arranged for fluidic communication with the fluidic passage by way of the nanopore. The second reservoir does not need to include a second fluidic passage.

As in the nanopore sensor examples described above, the nanopore sensor 100 of this embodiment can include electrodes 13, 15, and a voltage source 16 for applying an electrical potential between the reservoirs, across the solid state support structure. The nanopore is disposed in the suitable support structure and is solid state, biological, or some combination of the two in the manner described above.

Figure 6:
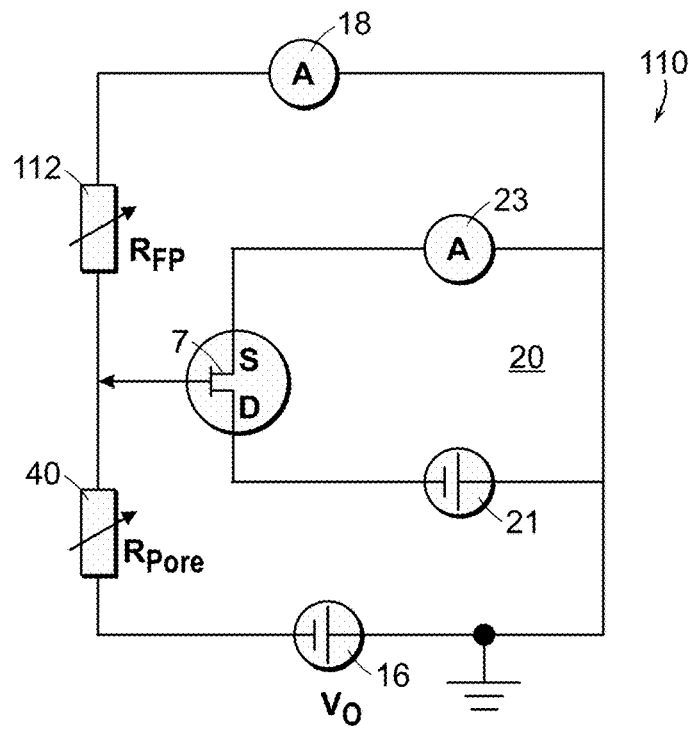
FIG. 6 is a circuit model of the of nanopore sensor of FIG. 5.

This nanopore sensor embodiment can be electrically modelled as shown in the circuit of FIG. 6. In this model, the aspect ratio of the nanopore, i.e., the ratio of nanopore diameter and length, and the aspect ratio of the fluidic passage are a priori specified to be sufficiently large that the fluidic access resistance of the trans and cis reservoir chambers can be ignored. There is then defined a resistance of the fluidic passage, $R_{FP}$, and the nanopore resistance, $R_{PORE}$. It is further a priori specified that the fluidic resistance of the fluidic passage, $R_{FP}$, is much larger than the bulk fluidic resistance of the cis reservoir and is much larger than the bulk fluidic resistance of the trans reservoir. As a result, as shown in FIG. 6 there can be modelled the nanopore sensor resistance as a fluidic passage resistance and a nanopore resistance.

Referring to both FIG. 6 and FIG. 5, an electrical transduction element 7, like that described above, is provided in the sensor to sense the electrical potential local to fluidic passage 105, to develop a characteristic that is indicative of the local electrical potential in the fluidic passage. An electrical connection, such as device or region of a device and/or circuit, a wire, or combination of circuit elements, that senses the electrical potential local to the site of the device and/or circuit can be provided as a transduction element to develop a signal indicative of local electrical potential. The location of the electrical transduction element 7 can be in a reservoir, on a surface of the support structure, as shown in FIG. 5, at a location within the fluidic passage, or other location within the nanopore sensor.

As shown in FIG. 6, in one embodiment, there can be provided a circuit 20 for supporting an electrical transduction element that is, e.g., a transistor device, having a source, S, a drain, D, and a channel region. The channel region can be physically disposed at a location in the nanopore sensor environment to make a local electrical potential measurement. This physical location of the channel region of the transistor can be at any convenient and suitable site for accessing local electrical potential.

Now considering this nanopore sensor arrangement, if the resistance of the fluidic passage 105 is comparable to the resistance of the nanopore 12, then local electrical potential measurement of the fluidic passage maximizes signal measurements indicative of species translocation through the nanopore in the manner discussed above, with reference to the access resistance of one reservoir relative to the nanopore, as in Expression (11). With a measurement of local potential at the site shown in the circuit of FIGS. 5-6, then the sensed voltage, $V_{Sens}$, is given as:

$$V_{Sens} = V_0 R_{FP}/(R_{Pore} + R_{FP}) \qquad (12)$$

where $R_{Pore}$ is the resistance of the nanopore, $R_{FP}$ is the resistance of the fluidic passage, and $V_0$ is the voltage 16 applied across the nanopore from the circuit.

The voltage signal, $V_{Sig}$, to be detected during species translocation through the nanopore is the small voltage change that is caused by the correspondingly small resistance change of the nanopore due to the partial blockage of the nanopore by the translocating species, with $V_{Sig}$ given as:

$$V_{Sig} = \frac{\partial V_{Sens}}{\partial R_{Pore}} dR_{Pore}. \qquad (13)$$

This signal is maximized when $$\frac{\partial V_{Sig}}{\partial R_{FP}} = 0,$$

requiring $R_{FP} = R_{pore}$. This relation demonstrates that if the fluidic passage resistance is not the same as the nanopore resistance, then the voltage signal that can be detected is smaller than a possible maximized voltage signal. The ratio, $R_{Signal}$, between the actual voltage signal that is attained and the maximized measured voltage signal tells how far the system is away from the optimal condition, with the ratio metric given as:

$$R_{Signal} = \frac{4(R_{FP}/R_{Pore})}{\left(1 + \frac{R_{FP}}{R_{Pore}}\right)^2} \qquad (14)$$

Figure 7:
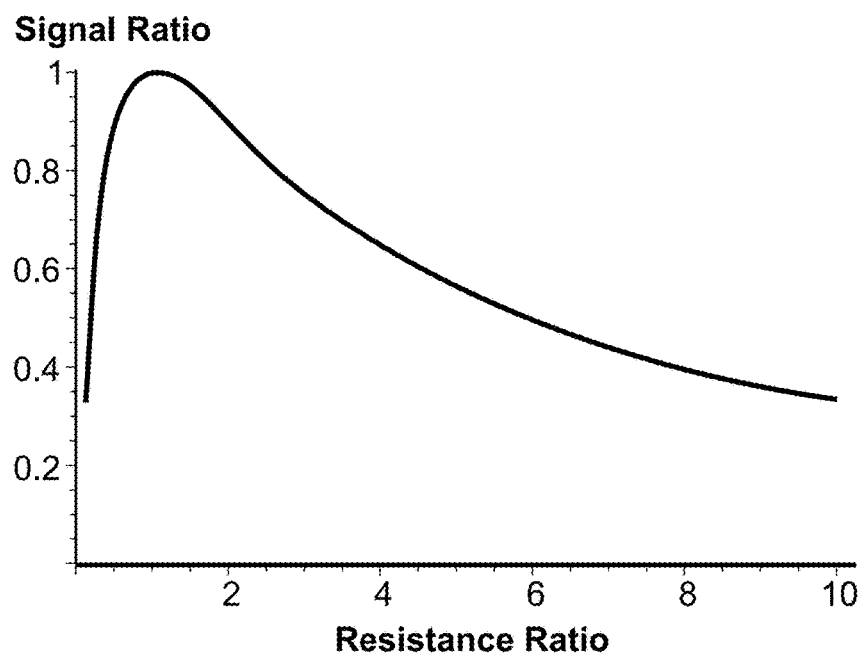
FIG. 7 is a plot of the ratio of measured transconductance signal to maximum achievable transconductance signal as a function of the ratio between the fluidic passage resistance and the nanopore resistance.

Expression (14) is plotted in FIG. 7. This plot indicates that when the fluidic passage resistance is 10% of the nanopore resistance, the voltage signal, $V_{Sig}$, is more than 30% of the maximum attainable signal. Thus, for purposes of this analysis, a condition in which when the fluidic passage resistance, $R_{FP}$, is at least about 10% of the nanopore resistance, $R_{Pore}$, and is no more than about 10 times the nanopore resistance, is considered to be matching of the fluidic passage resistance and the nanopore resistance.

To determine the structural and geometric requirements of the fluidic passage that meet these resistance matching requirements, it can in one example methodology be assumed that both the nanopore and the fluidic passage are generally cylindrical in geometry. Further, as stated above, the access resistance of the cis and trans reservoirs can be ignored for this analysis, given that the aspect ratio of the nanopore and the fluidic passage are relatively high relative to the cis and trans reservoirs. Finally, it is assumed that diffusion of ionic concentrations between the cis and trans reservoirs is in a steady state condition if the ionic concentrations in the two reservoirs are different.

Figure 8:
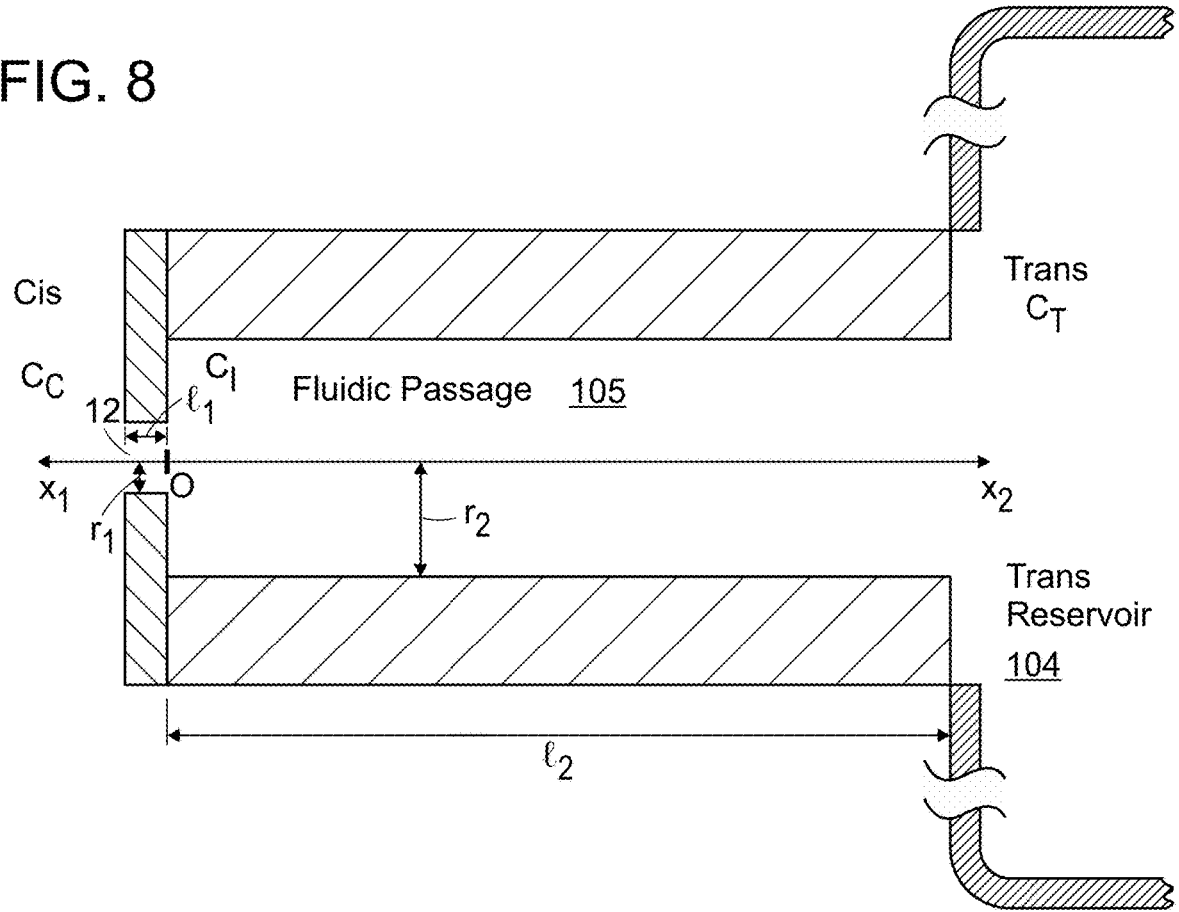
FIG. 8 is a schematic side view of the nanopore sensor of FIG. 5 with the definition of geometric parameters.

FIG. 8 is a schematic view defining the geometry of the fluidic passage 105. Here $l_1$, $r_1$ and $l_2$, $r_2$ are the length and the radius of the nanopore and the fluidic passage, respectively. $C_C$, $C_I$ and $C_T$ are the ionic solution concentrations in the cis chamber, the ionic solution concentration at the interface between the nanopore and the fluidic passage, and the ionic concentration in the trans chamber, respectively.

Under steady state conditions, the diffusion flux, Flux, of ionic concentration in the nanopore and the fluidic passage is equal, in a condition stated as:

$$\text{Flux} \propto \frac{C_C - C_I}{l_1} r_1^2 = \frac{C_I - C_T}{l_2} r_2^2 = const \quad (15)$$

whereby the interface concentration, $C_I$, can be determined as:

$$C_I = \frac{C_C l_2 r_1^2 + C_T l_1 r_2^2}{l_2 r_1^2 + l_1 r_2^2} \quad (16)$$

so that the ionic concentration in the nanopore, $C_{Pore}$, and the ionic concentration in the fluidic passage, $C_{FP}$, are given as:

$$\begin{cases} C_{Pore} = \frac{C_C - C_I}{l_1} x_1 + C_I \\ C_D = C_I - \frac{C_I - C_T}{l_2} x_2 \end{cases} \quad (17)$$

Under normal measurement conditions, the conductivity, $\sigma$, of a solution is in general approximately proportional to the ionic concentration of the solution, as:

$$\sigma = \sum \cdot C,$$

where $\Sigma$ is the molar conductivity of the solution and C is the ionic concentration. With this relation, the resistance, $R_{Pore}$, of the nanopore and the resistance, $R_{FP}$, of the fluidic passage, are given as:

$$\begin{cases} R_{Pore} = \int_0^{l_1} \frac{dx_1}{\sum C_{Pore} \pi r_1^2} = \frac{l_1}{\pi \sum r_1^2 (C_C - C_I)} \ln\left(\frac{C_C}{C_I}\right) \\ R_{FP} = \int_0^{l_2} \frac{dx_2}{\sum C_{FP} \pi r_2^2} = \frac{l_2}{\pi \sum r_2^2 (C_I - C_T)} \ln\left(\frac{C_I}{C_T}\right) \end{cases} \quad (18)$$

The resistance ratio can then be determined from Expression (18) as:

$$\frac{R_{FP}}{R_{Pore}} = \frac{\ln\left(\frac{C_C l_2 r_1^2 + C_T l_1 r_2^2}{C_T l_2 r_1^2 + C_T l_1 r_2^2}\right)}{\ln\left(\frac{C_C l_2 r_1^2 + C_C l_1 r_2^2}{C_C l_2 r_1^2 + C_T l_1 r_2^2}\right)}. \quad (19)$$

To obtain a maximum voltage signal, this ratio of resistance is optimally unity, or $$\frac{R_{FP}}{R_{Pore}} = 1.$$

By setting this ratio to the value 1 in expression (19), then:

$$\ln\left(\frac{C_C l_2 r_1^2 + C_C l_1 r_2^2}{C_C l_2 r_1^2 + C_T l_1 r_2^2}\right) = \ln\left(\frac{C_C l_2 r_1^2 + C_T l_1 r_2^2}{C_T l_2 r_1^2 + C_T l_1 r_2^2}\right) \quad (20)$$

To simplify this expression, the ratio of ionic concentrations in the cis and trans chambers, $C_C/C_T$, can be defined as $R_C$, and the ratio of the fluidic passage radius to the nanopore radius, $r_2/r_1$, can be defined as $R_r$. The aspect ratio of the nanopore, $AR_{Pore}$, can be defined as $AR_{Pore}=l_1/r_1$, and the aspect ratio of the fluidic passage, $AR_{FP}$, can be defined as $AR_{FP}=l_2/r_2$. The simplified expression is then given as:

$$AR_{FP} = \frac{1}{\sqrt{R_C}} \cdot R_r \cdot AR_{Pore} \quad (21)$$

This expression shows directly that to match the resistance of the fluidic passage with the nanopore resistance, the aspect ratio of the fluidic passage must increase proportionally to the ratio of the fluidic passage radius and the nanopore radius. If the fluidic solution ionic concentrations in the cis and trans chambers are equal, then the aspect ratio of the fluidic passage is set only by the ratio of radii of the fluidic passage and the nanopore. If the fluidic solution ionic concentrations are unequal, then the aspect ratio required of the fluidic passage to meet this condition is reduced by a corresponding factor, given that the low-concentration solution is provided in, e.g., the fluidic passage and trans chamber while the high-concentration solution is provided in the cis chamber. In one embodiment, a large ionic concentration ratio can be employed, in the manner described above, in concert with a fluidic passage design, to produce a reduced aspect-ratio requirement for the fluidic passage while maintaining the resistance matching between the fluidic passage and the nanopore.

When manufacturing or other considerations do not permit the fabrication of a fluidic passage with dimensions that produce a substantial resistance match to that of the nanopore, then the full ratio Expression (14) above can be considered, giving the relationship of all variables in the ratio as:

$$\frac{R_{FP}}{R_{Pore}} = \frac{\ln\left(\frac{R_C AR_{FP} + AR_{Pore} R_r}{AR_{FP} + AR_{Pore} R_r}\right)}{\ln\left(\frac{R_C AR_{FP} + R_C AR_{Pore} R_r}{R_C AR_{FP} + AR_{Pore} R_r}\right)} \quad (22)$$

Figure 9:
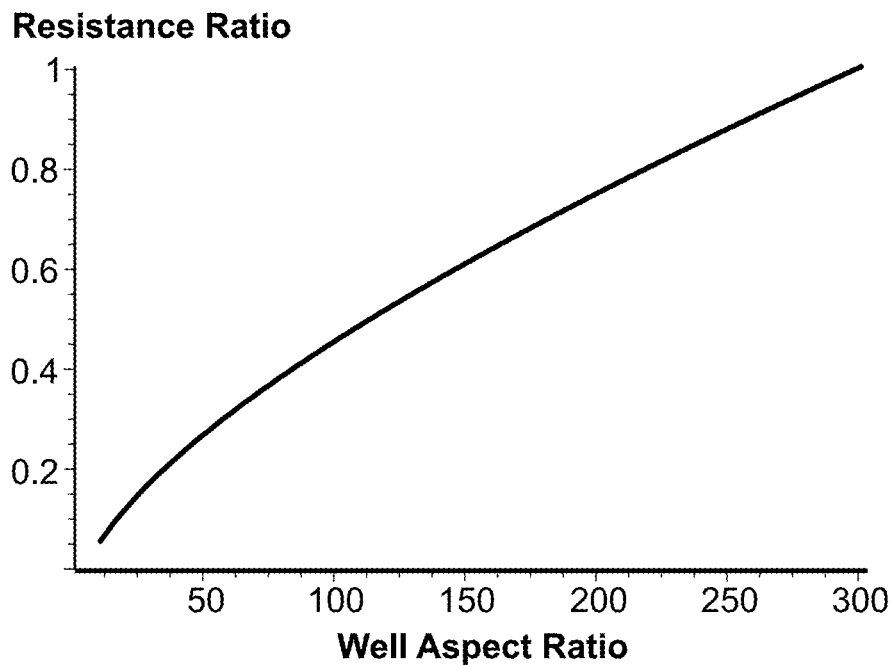
FIG. 9 is a plot of the ratio of resistance of the fluidic passage to resistance of the nanopore in the sensor of FIG. 5 as a function of ratio of fluidic passage diameter to fluidic passage length, for selected sensor dimensions.

Considering examples of this relationship, if the diameter of the fluidic passage is 1000 times larger than the diameter of the nanopore, e.g., 1.5 µm vs. 1.5 nm, then for a 3:1 aspect ratio of nanopore length to nanopore diameter, the aspect ratio of the fluidic passage is set as 300:1 for fluidic passage length to fluidic passage diameter, here 450 µm deep, to match the nanopore resistance when a difference in ionic concentration of 100:1 is employed between cis and trans chambers. This result is shown in the plot of FIG. 9, which shows the resistance ratio for a 3:1 aspect-ratio nanopore, 100:1 ionic concentration difference, and assumption of fluidic passage diameter of 1000 time nanopore diameter.

Figure 10:
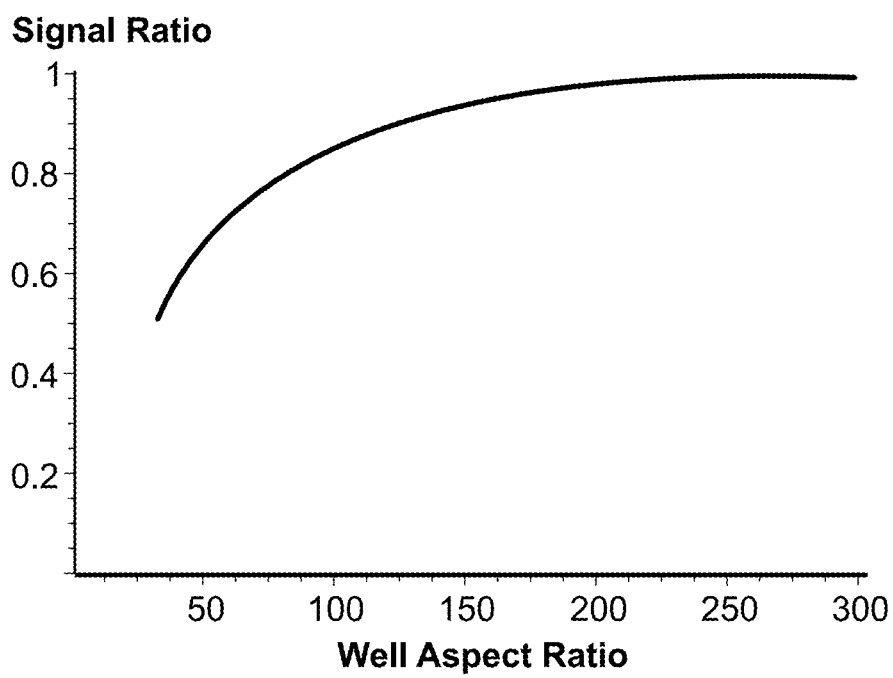
FIG. 10 is a plot of the of the ratio of measured transconductance signal to maximum achievable transconductance signal as a function of the ratio fluidic passage diameter to fluidic passage length, for selected sensor dimensions.

Such perfect resistance matching is not required. As explained above, when the fluidic passage resistance is 10% of the nanopore resistance, the voltage signal, $V_{Sig}$, is more than 30% of the maximum attainable signal. For example, given a fluidic passage having a 50:1 aspect ratio, having a 75 µm length, such can provide >20% of the nanopore resistance, as shown in the plot of FIG. 9, and can result in ~60% of the maximum voltage signal, as shown in the plot of FIG. 10. Based on the resistance-voltage signal relationship, as shown in the FIG. 9 plot, there can be determined the fluidic passage aspect ratio that is required to meet a performance specification for the nanopore sensor. Thus, no particular fluidic passage aspect ratio is required so long as the length of the passage is greater than the diameter of the passage. All that is required is the arrangement of an electrical transduction element at some site in the nanopore sensor that can measure the electrical potential local to the fluidic passage.

This nanopore arrangement including a fluidic passage connected between the nanopore and one of the reservoirs can compensate for some of the limitations imposed by only differing the cis and trans chamber ionic solution concentrations. In a nanopore sensor including differing ionic concentrations but no fluidic passage, the ionic concentration affects the nanopore resistance as well as cis and trans reservoir access resistances, and in this scenario the ability to match the nanopore resistance with one reservoir access resistance is limited, accordingly limiting the voltage signal that can be produced. Further, fluidic access resistance is localized in the vicinity of the nanopore, and is a function of distance from the nanopore, so that for electrical transduction elements, such as an amphiphilic membrane layer, that are mobile, there can be significant signal fluctuation. The inclusion of a fluidic passage between the nanopore and one reservoir enables structural definition of a fluidic resistance and adds an additional control parameter to the nanopore sensor. By control of both fluidic passage aspect ratio as well as cis and trans reservoir ionic solution concentrations, the nanopore sensor can be tuned to optimize voltage signal measurement.

Figure 11:
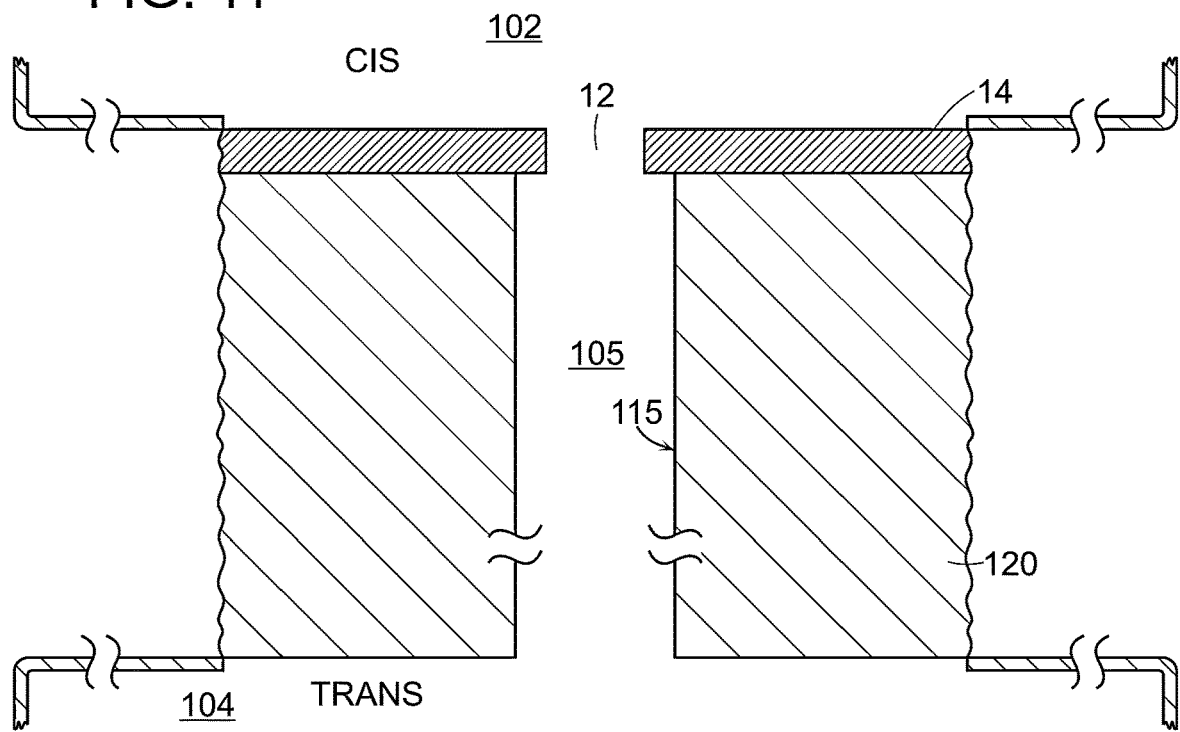
FIG. 11 is a schematic side view of a first fluidic passage configuration.

The fluidic passage connecting a reservoir to a nanopore can be configured in any convenient arrangement that enables a selected aspect ratio and integration with the nanopore sensor. Referring to FIG. 11, the fluidic passage 105 can be formed as a well, a trench, a channel, or other fluidic holding chamber in a structure provided for defining the nanopore. For example, the fluidic passage can be a duct, a channel, an open-ended trench, a path, or other geometry in a structure 120 that is arranged with a support structure 14 in which the nanopore 12 is disposed. In this example, a support structure layer 14 is disposed on a substrate 120 for providing the nanopore 12. The fluidic passage is formed in the substrate 120. The walls 115 of the fluidic passage can be configured to provide a suitable fluidic passage cross-sectional geometry, e.g., generally circular, elliptical, round, square, or other geometry. The fluidic passage is connected to a reservoir, e.g., the trans reservoir, having any dimensionality; the figures represent the trans reservoir schematically to indicate that the trans reservoir has any dimensionality and is not in general a high-aspect ratio passage like the fluidic passage.

Figure 12:
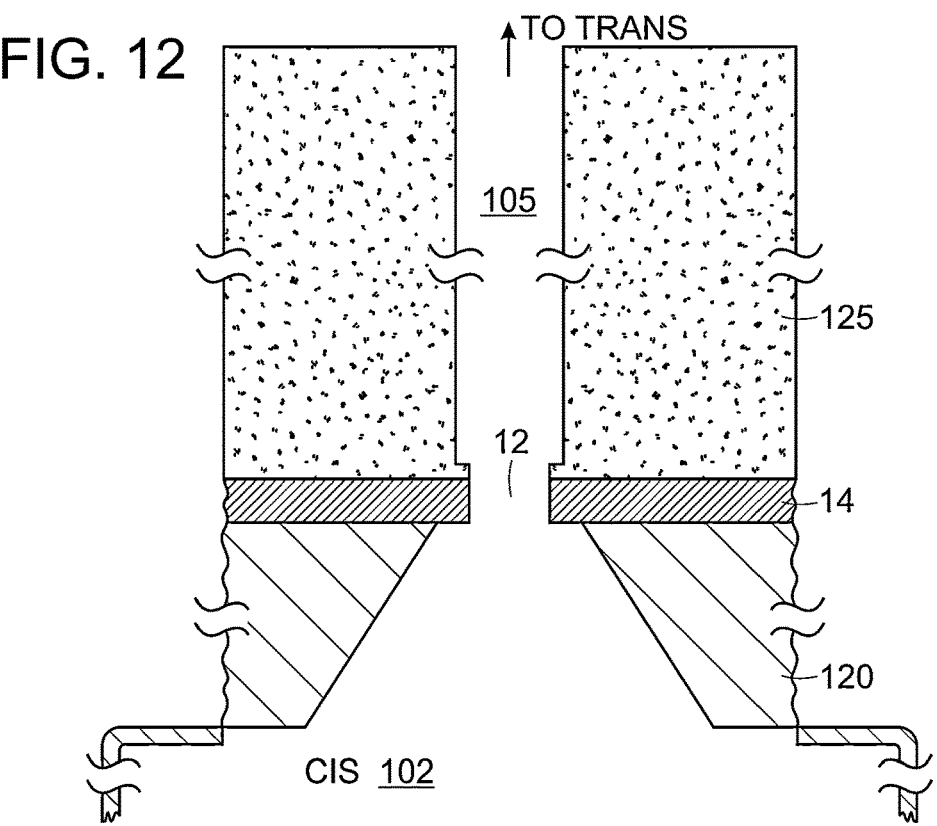
FIG. 12 is a schematic side view of a fluidic passage disposed on a support structure for a nanopore.

Referring to FIG. 12, the fluidic passage 105 can be disposed opposite a nanopore support structure. For example, a layer 125 of material can be provided on a nanopore support structure 14, with the fluidic passage 105 defined in the material layer 125. A substrate or structure 120 that supports the nanopore support structure 14 can be provided opposite the fluidic passage, on the opposite side of the support structure 14. The fluidic passage configurations of FIGS. 11-12 demonstrate that the fluidic passage can be disposed on any convenient location of the nanopore sensor.

Figure 13:
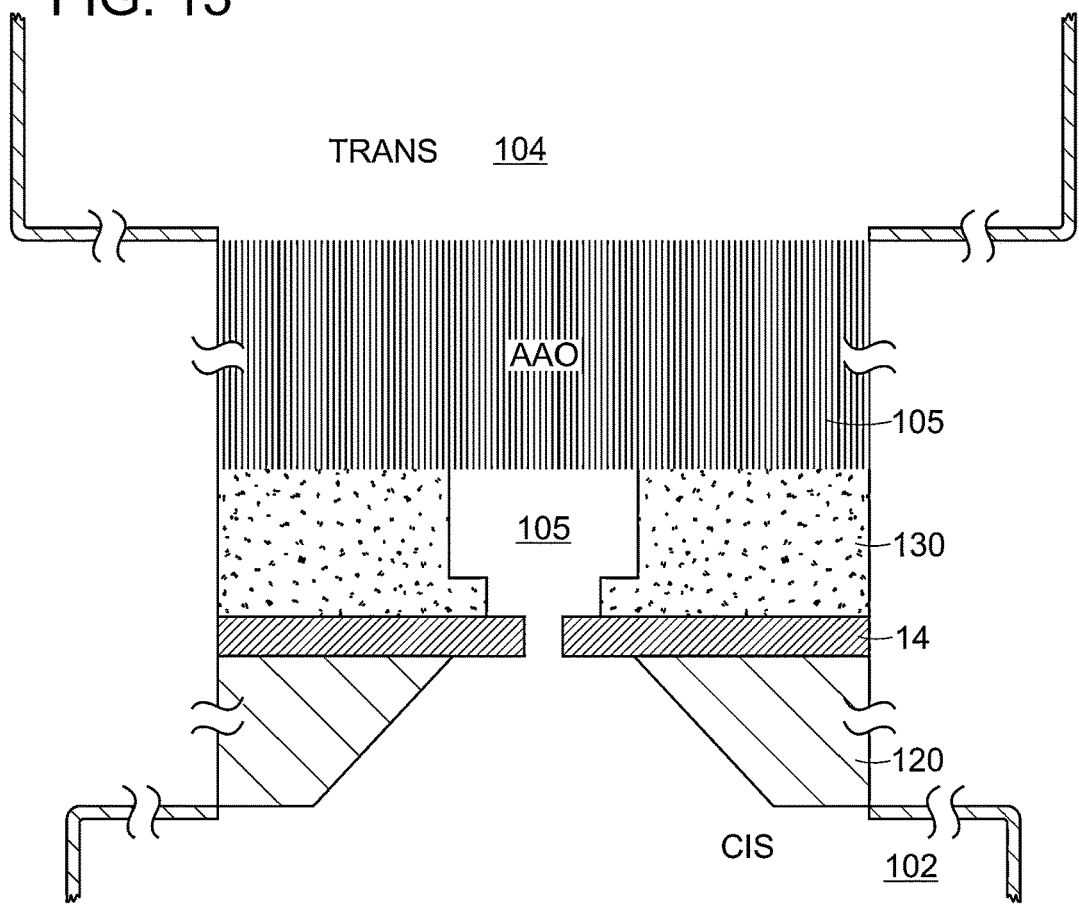
FIG. 13 is a schematic side view of a anodized aluminum oxide fluidic passage configuration.

Referring to FIG. 13, the fluidic passage 105 can be provided as a population of pores, wells, channels, or other geometry, in a selected arrangement. For example, the fluidic passage 105 can include a layer of anodized aluminum oxide (AAO). AAO is a conventional material that can be formed with very high aspect ratio holes e.g., >1000:1, having a diameter of about 100 nm. These AAO holes are arranged in a quasi-hexagonal lattice in two dimensions with a lattice constant in the range of several hundred nanometers. An aluminum oxide film can be anodized under controllable anodizing conditions, and such anodization can be conducted on a film having surface pre-patterning, to tune the AAO lattice constant and hole diameter. The population of AAO holes work in concert to provide an effective aspect ratio. This AAO arrangement is an example of a holey film, membrane, or other structure having a population of holes, wells, pathways, or other channels, that can be employed as a fluidic passage.

In addition, any fluidic passage configuration can be filled with a gel or other porous substance, or a selected material that is disposed in the fluidic passage to increase the fluidic resistivity of the fluidic passage.

Figure 14:
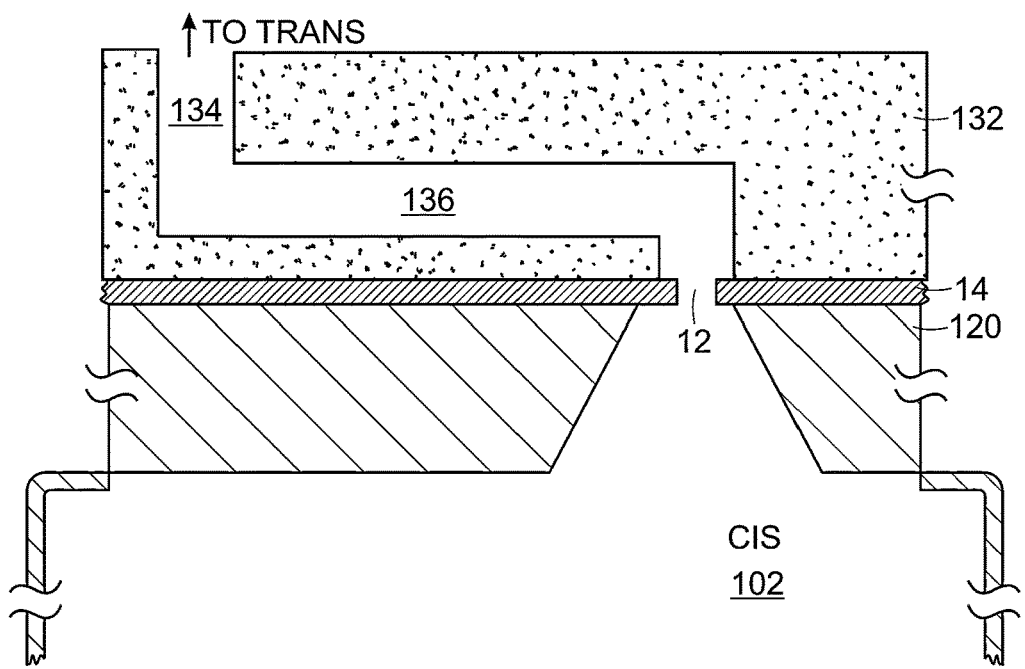
FIG. 14 is a schematic side view of a lateral fluidic passage configuration.

The fluidic passage can be configured in a vertical arrangement, horizontal arrangement, or combination of horizontal and vertical geometries. Referring to FIG. 14, in one embodiment, there is schematically shown a fluidic passage including a vertical passage section 134 and a horizontal passage section 136. Such arrangements can be provided in, e.g., a surface layer 132 on a support structure 14, or can be integrated into a substrate or other structural feature.

Referring to FIGS. 15A and 15B, the fluidic passage 105 can be configured in a lateral or vertical geometry of any suitable path for achieving a selected fluidic passage aspect ratio. As shown in the schematic view in FIG. 15A, a path that winds around itself, either laterally or vertically, can be configured for achieving a selected fluidic passage aspect ratio. As shown in the schematic view of FIG. 15B, a serpentine path, either lateral or vertical, can be alternatively employed as a fluidic passage. No particular geometry is required, and the fluidic passage can traverse multiple materials and different support structure members in connecting between a reservoir and a nanopore. The geometry can be formed in a layer on a support structure, substrate, or combination of elements in the sensor. The port 140 of the fluidic passage can be connected in the horizontal or vertical direction to provide fluidic communication between a reservoir of liquid and the nanopore.

These various fluidic passage configurations can in various embodiments include, e.g., an AAO film having holes of about 150 nm in diameter, with a hole-to-hole distance of about 300 nm, and a film thickness of between about 100 µm-1000 µm; a planar PDMS/oxide/nitride channel having a width of between about 0.5 µm-1 µm, a depth of between about 100 nm-200 nm, and a length of between about 200 µm-500 µm; a deep well in a dielectric material with a well diameter of between about 0.5 µm-2 µm and a diameter of between about 20 µm-50 µm; and a silicon wafer well having a diameter of between about 2 µm-6 µm and a depth of between about 200 µm-300 µm. In each of these examples, the cis and trans ionic concentrations can be the same or can be different, with a selected ionic concentration ratio, e.g., between about 50:1-1000:1 as a ratio of cis:trans ionic concentrations.

Turning to implementation of a fluidic passage with an electrical transduction element for making a local potential measurement in the fluidic passage, as explained above, a local electrical potential measurement can be made in the nanopore sensor with any suitable device or circuit that accommodates the nanopore implementation. Referring to FIGS. 16A-16E, the fluidic passage configurations described just above can be adapted to include an electrical transduction element at the site of the nanopore connection to the fluidic passage. The configuration of FIG. 16A corresponds to the fluidic passage design of FIG. 11. Here, a silicon-on-insulator (SOI) wafer can be employed to form the substrate 120 with a buried oxide layer (BOX) and silicon layer 152 provided atop thereof. The nanopore 12 can be formed in these layers 150, 152. The silicon layer 152 can be configured as a conductance channel for making a local potential measurement at the site of the nanopore, with electrically conducting source 154 and drain 156 regions provided for measuring the conductance that is transduced by the silicon conductance channel. Similarly, as shown in FIGS. 16B, a silicon layer 152 can be configured as a conductance channel region with source and drain regions 154, 156, here in a layer 125 that defines the fluidic passage. As shown in FIG. 16C, a sensing electrode 158 or electrodes, of metal, carbon nanotubes, or other material, can be configured at the site of the nanopore 12 and connected for sensing by, e.g., a drain electrode 156.

Referring to FIGS. 16D-16E, lateral fluidic passage channels are shown in cross section with a transduction element. In the configuration of FIG. 16D, the fluidic passage 105 is provided in a layer 159, such as a nitride layer. The nitride layer 159 is provided on a support structure 14 such as a silicon layer 152 from a SOI waver, with an underlying BOX layer 150. Source and drain regions 154, 156 are provided in connection to the silicon layer 152, patterned as a channel for transducing the local electrical potential at the nanopore. In the configuration shown in FIG. 16E, the fluidic passage, shown in cross-section to depict a channel such as that in FIGS. 15A-15B, is provided in a top layer 160, such as PDMS. The channel can be moulded into the top layer 160 and then connected to the nanopore sensor structure. A silicon layer 152 from a SOI wafer can be configured as a conductance channel, with source and drain regions 154, 156, connected for transducing the local electrical potential at the nanopore. Each of these configurations in FIGS. 16A-16E enable a sensing of the local electrical potential in the fluidic passage at nanopore.

For any of the nanopore sensor embodiments, with or without a fluidic passage, a range of further electrical transduction elements can be employed. For many applications, a nanowire-based FET device can be a well-suited device, but such is not required herein. The SET, QPC, lipid bilayer, or other device and nanopore implementation, whether biological or solid state, can be employed. Any circuit or device that enables a local potential measurement can be employed.

Figure 17:
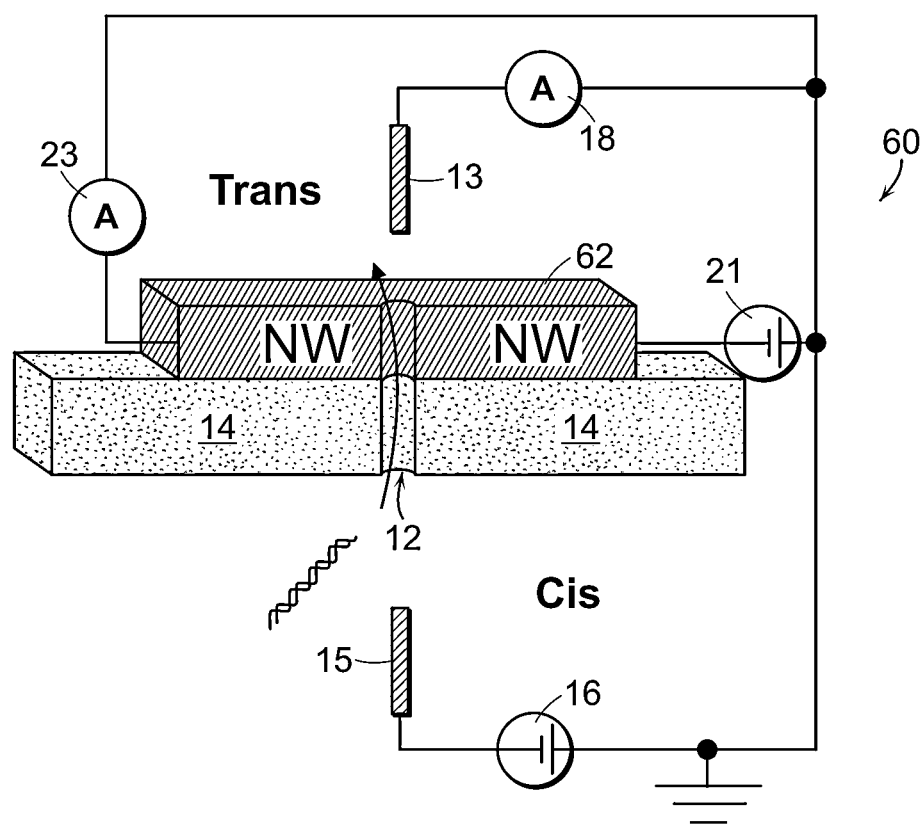
FIG. 17 is a schematic view of a nanopore sensor configured for local electrical potential measurement with a nanowire FET disposed on a membrane.

In one example, a nanowire FET can be configured at the site of the nanopore as shown in FIG. 17 here shown without the fluidic passage for clarity. In this nanowire implementation 60, there is provided a nanowire 62 on the support structure 14 in which is disposed the nanopore 12. The nanowire can be formed of any suitable electrically conducting or semiconducting material, including fullerene structures and semiconducting wires. The term "nanowire" as used herein refers to an electrical conduction channel that is characterized by a width that is compatible with the signal decay length measured from the nanopore site as described above. The channel width is preferably on the same order of magnitude as the decay length and can be larger. The nanowire can be made from any semiconductor material that is stable in the selected reservoir solution.

Figure 18:
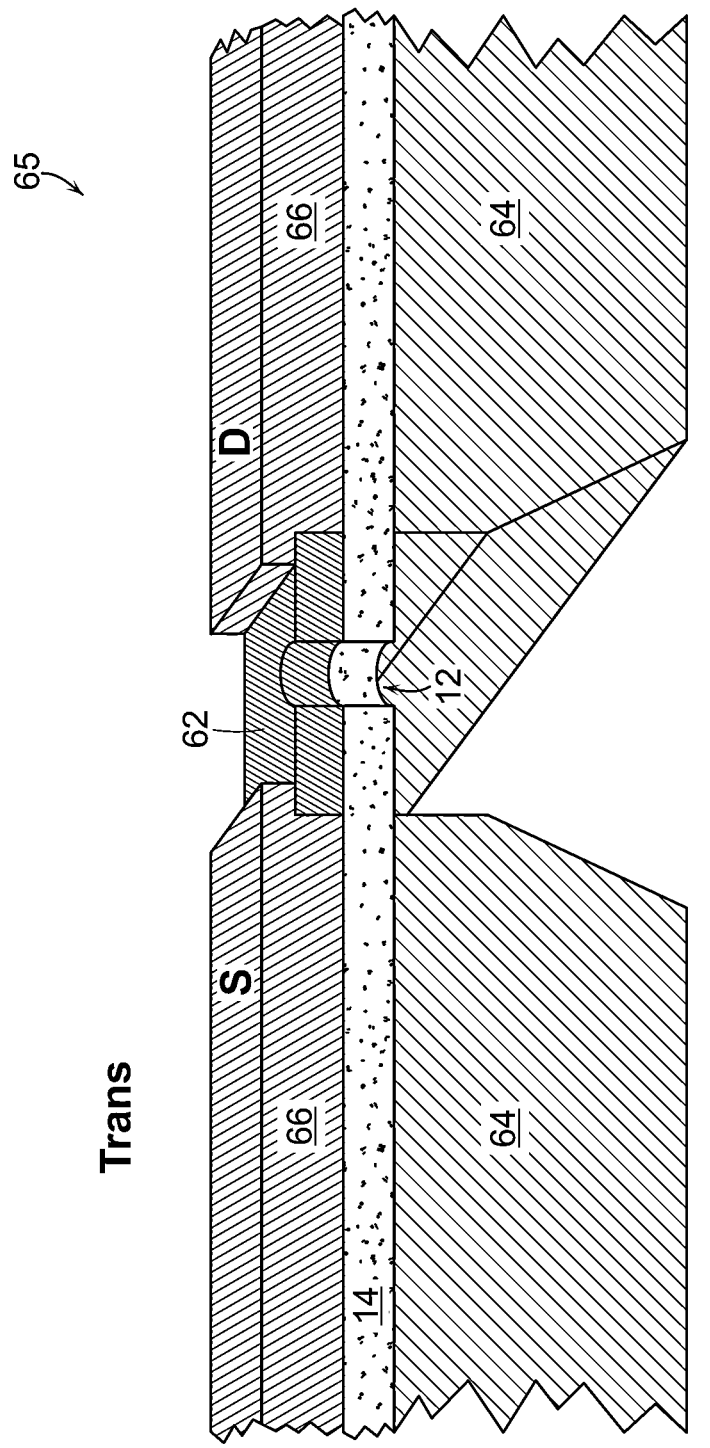
FIG. 18 is a perspective view of one example implementation of the nanopore sensor configuration of FIG. 17.

FIG. 18 is a perspective view of an implementation 65 of the nanopore sensor of FIG. 6. Here is shown the nanowire 62 provided on a membrane support structure 14 that is self-supported across its extent, like a trampoline, between a support frame at the edges, provided on a support structure 64 such as a substrate. The nanowire is provided on the membrane with a nanopore extending through the thickness of the nanowire and the membrane. As shown in FIGS. 17 and 18, the nanopore 12 does not extend across the width of the nanowire. There is a region of the nanowire that is unbroken along the extent of the nanopore so that electrical conduction is continuous along the length of the nanowire. A metallization region or other electrically conducting region is provided at each end of the nanowire to form source (S) and drain (D) regions. With this configuration, the nanopore sensor can be configured with cis and trans reservoirs and a fluidic passage connected to one of the reservoirs, for detecting translocation of species from one reservoir through the nanopore to the other reservoir.

Referring also to FIGS. 19A-19B, the support structure and nanowire configuration can be implemented in a variety of alternative arrangements, and a support structure, such as a membrane support layer, is not required for applications in which a nanowire material is self supporting and can itself function as a support structure in which the nanopore is disposed. For example, as shown in FIGS. 19A-B, in a graphene-based nanopore sensor 68, there can be provided a support layer 70, which in turn supports a graphene membrane 72. The graphene membrane 72 is self-supported across an aperture in the support layer 70. The graphene membrane in turn supports a nanowire 62, with a nanopore 12 extending through the thickness of the nanowire and the graphene, and the nanowire remaining continuous along some point of the nanowire. As shown in FIGS. 20A-20B, this arrangement can be altered, with the nanowire 72 instead disposed under the graphene layer 72, on a support layer 70.

Figure 21B:
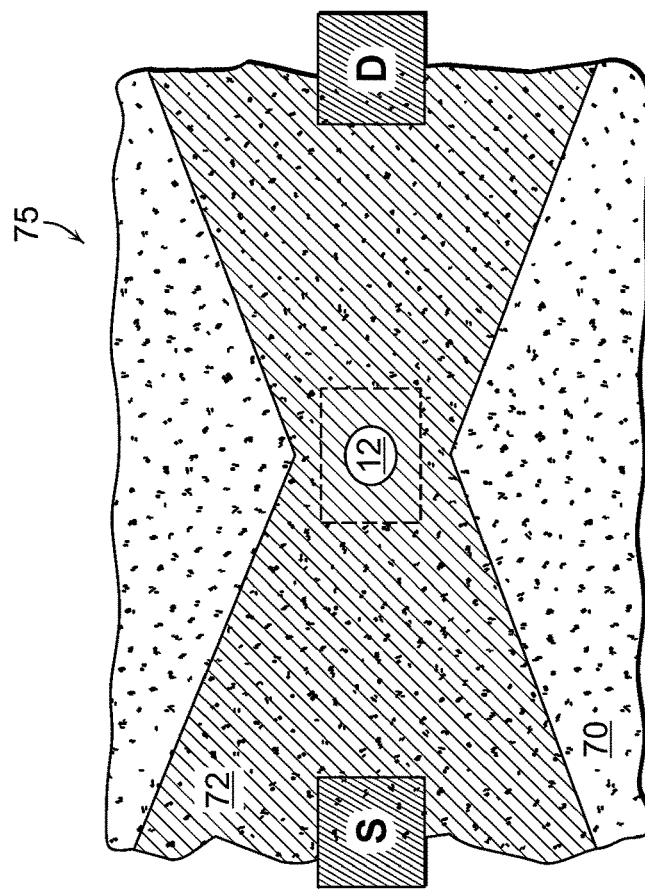
FIGS. 21A-21B are a schematic view of a nanopore sensor configured for local electrical potential measurement with a graphene membrane, and a plan view of an example implementation of this nanopore sensor, respectively.
Figure 21A:
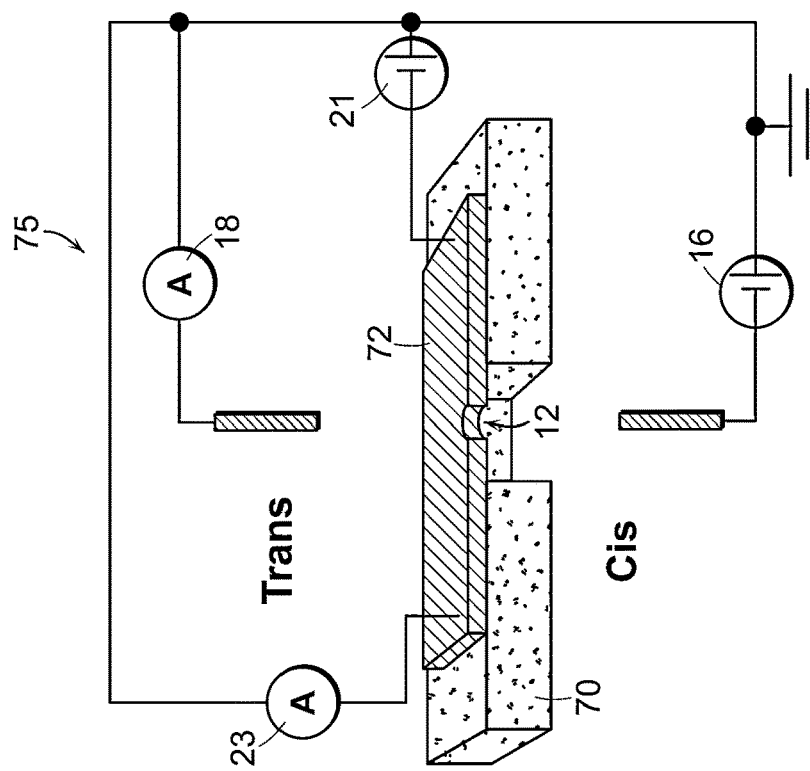

In an alternative graphene-based nanopore sensor 75, as shown in FIGS. 21A-21B, there can be configured a support structure, such as a support layer 70, on which is disposed a graphene layer 68 that functions to provide a structure in which a nanopore 12 is configured and that itself functions to provide a nanowire. The graphene can be provided in any suitable geometry that provides the requisite nanowire at the site of the nanopore 12. In this configuration, the graphene layer 68, due to its thickness and conductivity, senses the local electrical potential on both sides of the nanopore, i.e., the conductance of the graphene layer changes as a function of the local potential in both the trans and cis reservoirs. The nanopore sensor signal of a local potential measurement is therefore for this graphene-based nanopore sensor an indication of the difference between the cis and trans reservoir potentials.

Thus any in a very wide range of electrical transduction elements that can be employed to measure the electrical potential local to the fluidic passage of the nanopore sensor. A semiconductor-based FET or other sensing device, a sensing metal electrode connected to a device such as an FET device, a graphene-based device, or other suitable transduction element can be employed.

As demonstrated by these arrangements, the support layer, support layer membrane, nanowire, and support structure can be configured with any in a wide range of materials combinations and thicknesses. The fluidic passage configurations described above can be integrated into any of these arrangements. For many applications, it can be preferred that the structure in which the nanopore is disposed be as thin as possible, and preferably no thicker than the extent of a species object, or object region to be detected. As explained above, support structure materials can include nitrides, oxides, conductors, semiconductors, graphene, plastics, or other suitable material, which can be electrically insulating or electrically conducting.

Figure 22B:
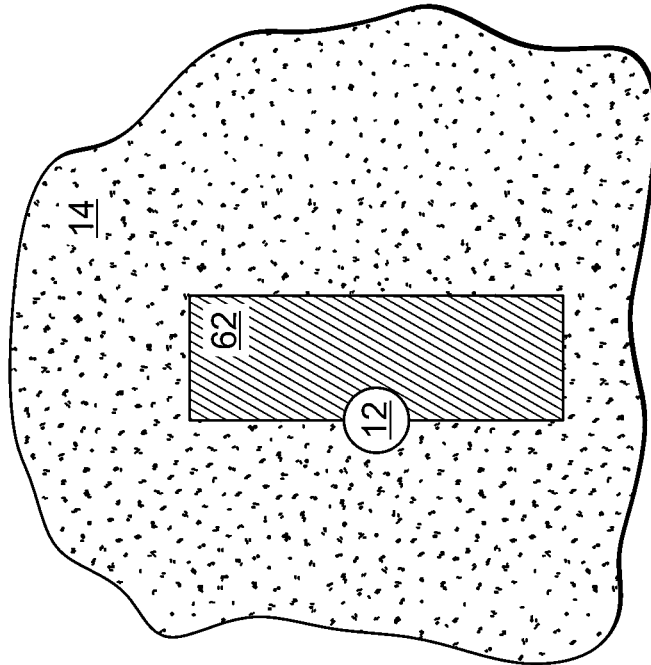
FIGS. 22A-22D are schematic plan views of example locations of a nanopore with respect to a nanowire in a nanopore sensor configured for local electrical potential measurement.
Figure 22A:
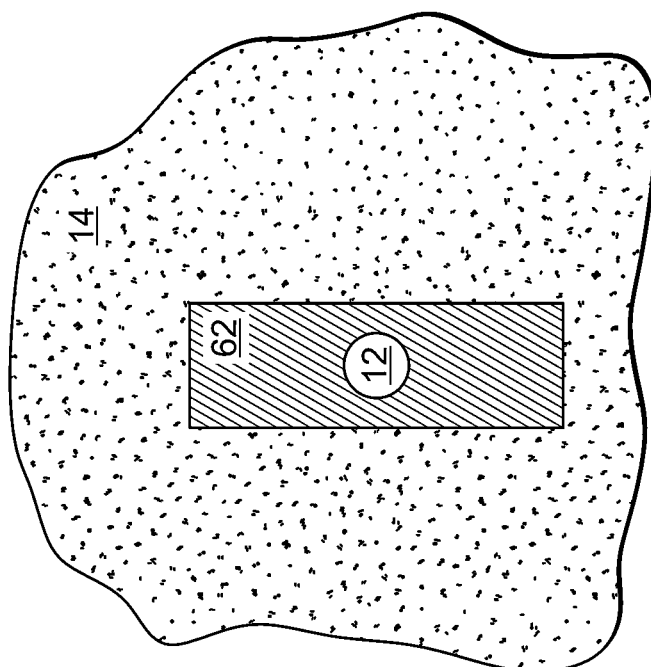
Figure 22D:
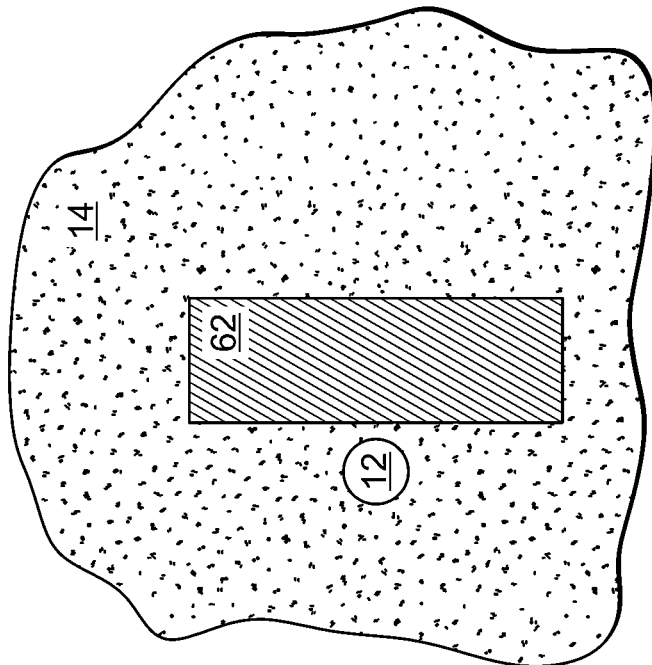
Figure 22C:
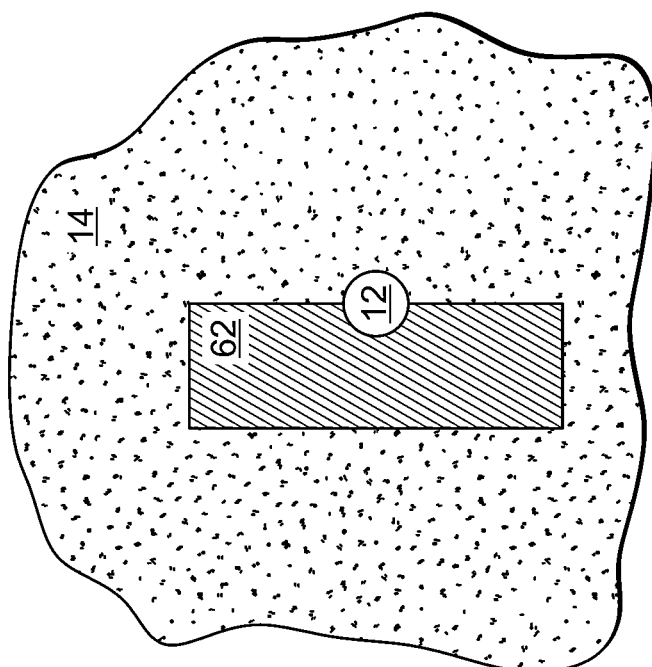

As shown in FIGS. 22A-22D, for a nanowire implementation, the nanopore is provided at the location of a nanowire 62 such that an unbroken, continuous path for electrical conduction is provided through the nanowire. The nanopore can be provided at a central region of the nanowire, as depicted in FIG. 22A, can be provided at an edge of the nanowire, as depicted in FIGS. 22B-22C, or can be provided at a site near to or adjacent to the nanowire, as depicted in FIG. 22D. In all cases, a continuous path for electrical conduction is provided through the nanowire.

In the nanopore arrangements of FIGS. 22A-22C, it is found that that the sensitivity of the nanopore region is also significantly enhanced compared to the sensitivity of the same region prior to nanopore drilling. This sensitivity localization can be understood by a model accounting for the reduction of the cross-sectional area of the nanowire as a conduction channel, assuming all other material properties, such as doping level and mobility remain unchanged. The reduced cross-sectional area of the nanowire increases the resistance of the nanopore region and therefore alleviates series resistance and signal attenuation from other portions of the nanowire. Quantitatively, this sensitivity enhancement at the nanopore region can be obtained from the following equation for a rectangular-shaped nanopore as an example:

$$\Delta = \left(\frac{\rho_0 L}{\rho(L - L_0) + \rho_0 L_0}\right)^2. \quad (23)$$

Here, $\Delta$ is the sensitivity enhancement defined as the sensitivity of the device with a nanopore divided by the sensitivity without the nanopore, and $\rho_0$ and $\rho$ are the linear resistivities of the nanowire conduction channel with and without the nanopore, respectively. L is the total channel length and $L_0$ is the channel length of the nanopore region, which for this square example is equal to the side length of the nanopore along the nanowire axial direction. For other portions of nanowire, because all parameters remain the same but the total channel resistance is increased slightly due to the nanopore, the sensitivity should decrease slightly after nanopore drilling. The combination of increased sensitivity at the nanopore region and decreased sensitivity of all other nanowire portions makes the sensitivity of a nanopore sensor enhanced, self-aligned and localized at the nanopore.

In fabrication of the nanopore sensor, both for embodiments including a fluidic passage and embodiments not including a fluidic passage, first considering a nanowire-based solid state nanopore sensor, a short-channel nanowire can be preferred, and for many applications, a silicon nanowire (SiNW) can be preferred because the SiNW has been demonstrated as an excellent electrical potential and charge sensor for sub-cellular and single-virus level signalling with remarkable stability in solution. To minimize signal attenuation from channel series resistance, the SiNW channel can be reduced, if desired, to less than about 200 nm by nickel solid-state diffusion. SiNWs can be fabricated by, e.g., chemical vapor deposition, or other suitable process, and disposed on a selected membrane, such as a nitride membrane, by solution. For many applications, a commercially-available nitride membrane chip can be suitably employed. Electron beam lithography or optical lithography can be employed for producing source and drain electrodes at ends of the nanowire. All electrodes and electrical contacts are to be passivated with, e.g., a nitride or oxide material, and such can be accomplished after metal evaporation and before lift-off processes. The nanopore can be produced at a selected site by, e.g., electron beam, or by other beam species or etching process that produces a selected nanopore dimension.

In fabrication of a graphene-based nanopore sensor including a nanowire structure on top of the graphene membrane, like the graphene-based nanopore sensor of FIGS. 19A-19B, first a membrane, such as a nitride membrane, is processed to form a micron-sized aperture in the membrane, e.g., by electron beam lithography or photolithography and reactive ion etching (RIE). Then a graphene sheet or piece is disposed on the nitride membrane, covering the aperture, to form a graphene membrane. The graphene sheet can be synthesized by CVD or other process, or produced by mechanical exfoliation, and transferred to the nitride membrane, over the nitride membrane aperture.

Electron beam lithography or photolithography can then be conducted with metal evaporation to define electrodes in the conventional manner on the nitride membrane. Dielectrophoresis or other suitable process can then be employed to align a nanowire, such as a silicon nanowire, on top of the graphene membrane at the location of the aperture in the nitride membrane. Electron beam lithography or photolithography can then be conducted with metal evaporation to define the source and drain contacts at ends of the SiNW. Thereafter, excessive graphene can be removed by electron beam lithography or photolithography and, e.g., UV-ozone stripper, oxygen plasma, or other suitable method to remove graphene from regions outside the intended graphene membrane location. Finally, a nanopore is produced through a site at the nanowire and the underlying graphene membrane by, e.g., electron beam milling, ion beam milling, etching, or other suitable process as described above.

In fabrication of a graphene-based nanopore sensor including a graphene membrane that is on top of a nanowire FET structure, like the graphene-based nanopore sensor of FIGS. 20A-20B, a suitable structure can be employed for configuring the arrangement, e.g., with a silicon-on-insulator chip (SOI). In this example, an aperture is first formed through the backside thick silicon portion of the SOI chip, e.g., by $XF_2$ etching, stopping on the oxide layer, to form an oxide-silicon membrane. Then electron beam lithography or photolithography is employed to remove the oxide layer from the SOI chip in a smaller aperture region, producing a membrane of silicon from the thin silicon region of the SOI chip. This silicon membrane is then etched to form a nanowire of silicon, e.g., with electron beam lithography or photolithography and chemical etching or RIE. In one example, a dove-tail-shaped Si piece is formed as shown in FIG. 20B, aligned with the aperture in the oxide membrane of the SOI chip.

Electron beam lithography or photolithography can then be conducted with metal evaporation to define electrodes in the conventional manner on the oxide layer. Then a graphene sheet or piece is disposed on the oxide membrane, covering the aperture, to form a graphene membrane over the silicon nanowire. The graphene sheet can be synthesized by CVD or other process, or produced by mechanical exfoliation, and transferred to the oxide membrane, over the SiNW and oxide membrane aperture. It is recognized that because the graphene sheet is being overlaid on top of the patterned silicon layer, the graphene piece may not be flat. If leakage is a concern for this configuration, then a thin layer of, e.g., $SiO_x$ can be coated around the graphene edges to form a sealed edge condition.

Thereafter, excessive graphene can be removed by electron beam lithography or photolithography and, e.g., UV-ozone stripper, oxygen plasma, or other suitable method to remove graphene from regions outside the intended graphene membrane location. Finally, a nanopore is produced through a site at the overlying graphene and the silicon nanowire, e.g., by electron beam, in relation to the location of the most narrow Si geometry.

In fabrication of a graphene-based nanopore sensor like that depicted in FIG. 21A, first a membrane, such as a nitride membrane, is processed to form a micron-sized aperture in the membrane, e.g., by electron beam lithography or photolithography and reactive ion etching (RIE). Then a graphene sheet or piece is disposed on the nitride membrane, covering the aperture, to form a graphene membrane. The graphene sheet can be synthesized by CVD or other process, or produced by mechanical exfoliation, and transferred to the nitride membrane, over the nitride membrane aperture.

Electron beam lithography or photolithography can then be conducted with metal evaporation to define source and drain electrodes in the conventional manner on the graphene membrane. Thereafter, the graphene is patterned in a dove-tail or other selected shape by electron beam lithography or photolithography and, e.g., UV-ozone stripper, oxygen plasma, or other suitable method to produce a narrow graphene region in the vicinity of the selected site for a nanopore. Finally, a nanopore is produced through the graphene membrane by, e.g., electron beam.

In fabrication of a SET-based nanopore sensor like that of FIG. 1F, any suitable membrane material, both electrically conductive and electrically insulating, can be employed. A nitride membrane structure or other structure can be employed, such as a graphene membrane or combination graphene-nitride membrane structure as-described above. If an electrically conducting membrane material is employed, it can be preferred to coat the material with an insulating layer, such as an oxide or nitride layer, on the side of the membrane on which the SET is to be formed. Electron beam lithography and metal evaporation techniques can then be employed to form the source and drain regions and the SET region out of a suitable metal. A nanopore can then be formed at the location of the SET in the manner given above. If an insulating layer is provided on an electrically conducting membrane material and the insulating layer coated the length of the nanopore through the membrane, then it can be preferred to remove that insulating material from the nanopore sidewall by, e.g., HF or other suitable etching, from the backside of the nanopore, to remove the insulator layer from the nanopore and from the adjacent vicinity of the nanopore.

In fabrication of a QPC arrangement like that of FIG. 1G with a nanopore, an SOI structure can be employed, removing the thick silicon layer in the manner described above, and then using electron beam lithography to define the top silicon layer structure in the QPC arrangement. The nanopore can then be formed through the membrane in the manner given above.

In all of these processes, there can be included one or more process steps and additional materials to form a fluidic passage connected between the nanopore and one of the fluidic reservoirs. A planar channel can be defined by patterned etching of a nitride or oxide layer at the nanopore site, with an oxide, glass, PDMS, or other material bonded onto the nitride or oxide layer to seal the fluidic passage channel. Alternatively, a thick material layer, such as an oxide layer, nitride layer, PDMS layer, polymer or other layer, can be etched or drilled, e.g., by deep reactive ion etching (RIE) to define a fluidic passage. Further, as described above, an underlying support substrate, such as a silicon wafer, can be etched, e.g., by RIE, to form a fluidic passage through the thickness of the wafer. These example processes are not intended to be limiting and are provided as general examples of techniques for producing nanopore sensors. Any suitable support structure material and device material can be employed.

The nanopore sensor fabrication processes can be tailored to accommodate any suitable nanopore structure, whether solid state, biological, or some combination of the two. As explained above, there can be employed a protein nanopore disposed in an aperture of a solid state support structure such as an FET channel material as described above. Further as described above, a protein nanopore can be employed as disposed in an amphiphilic layer, or aperture in a solid state support structure at the site of an FET channel. Any combination of materials can be employed in the support structure that contains the nanopore.

In each of these processes, it is preferred that the dimensions of the nanopore be selected based on a selected ratio of the reservoir buffer solution concentrations, to achieve a desired electrical potential measurement in the manner described above, in conjunction with consideration for the species objects to be investigated with the nanopore sensor. The analytical expressions above can be employed to determine an optimum nanopore size for a given species to be detected by translocation through the nanopore, in concert with the other nanopore sensor parameters and operation, for enabling electrical potential measurement for nanopore sensing of the species.

This is particular important for maximizing the ability to distinguish between different species objects as nanopore translocation of the objects is conducted. The graphene-based nanopore sensors described above are particularly attractive for sensing molecular species such as DNA and other biopolymer species because the graphene thickness is on the order of a DNA base extent. But because graphene is electrically gated on both sides of the graphene by the cis and trans reservoir solutions, and the electrical potential in the two reservoirs is opposite, the sum of electrical potentials that is indicated by the graphene potential measurement is smaller than that indicated by the implementation of a nanowire on one side of a membrane. But for a small nanopore, e.g., of about 1 nm in diameter, and with a sufficiently large ratio in buffer concentration between the cis and trans reservoirs, the sum of electrical potentials that is indicated by the graphene potential measurement is comparable to that of a nanowire nanopore sensor.

In general, as nucleotides or other polymer translocates through the nanopore, the rate of translocation can be controlled by a polymer binding moiety, for a graphene-based nanopore sensor or other nanopore support structure material. Typically the moiety can move the polymer through the nanopore with or against an applied field. The moiety can be a molecular motor using for example, in the case where the moiety is an enzyme, enzymatic activity, or as a molecular brake. Where the polymer is a polynucleotide there are a number of methods for controlling the rate of translocation including use of polynucleotide binding enzymes. Suitable enzymes for controlling the rate of translocation of polynucleotides include, but are not limited to, polymerases, helicases, exonucleases, single stranded and double stranded binding proteins, and topoisomerases, such as gyrases. In particular the enzyme may be a helicase or modified helicase such as disclosed by WO2013-057495 and WO2014-013260. For other polymer types, moieties that interact with that polymer type can be used. The polymer interacting moiety may be any disclosed in WO-2010/086603, WO-2012/107778, and Lieberman K R et al, J Am Chem Soc. 2010; 132(50): 17961-72), and for voltage gated schemes, Luan B et al., Phys Rev Lett. 2010; 104(23): 238103.

It is recognized that more than one polymer unit may contribute to the measured signal during translocation of the polymer, in which case the signal may be referred to as being k-mer dependent, a k-mer being k polymer units of a polymer, where k is a positive integer. The extent to which the signal is dependent upon a k-mer is dependent upon the shape and length of the aperture and the polymer type. For example, with the translocation of a polynucleotide through an MspA pore, the signal may be considered as being dependent upon 5 nucleotide bases. Alternatively, for example where the nanopore support structure is mono-atomically thin, the signal may be dependent upon only a small number of polymer units and may even be dominated by a single polymer unit. The measured signals may be used to determine a sequence probability of polymer units or to determine the presence or absence of an analyte. Suitable exemplary methods of signal analysis are disclosed in WO2013-041878 and WO2013-121224.

Example I

Fabrication of a SiNW FET in a Nanopore Sensor

SiNWs were synthesized using an Au-nanoparticle-catalyzed chemical vapor deposition (CVD) method. 30 nm-diameter gold nanoparticles (Ted Pella Inc., Redding, CA) were dispersed on a silicon wafer coated with a 600 nm-thick layer of silicon oxide (NOVA Electronic Materials Inc., Flower Mound, TX). Boron-doped p-type SiNWs were synthesized at 435° C. and 30 Torr, with 2.4 standard cubic centimeters per minute (sccm) silane as a silicon source, 3 sccm diborane (100 ppm in helium) as a boron dopant source and 10 sccm argon as the carrier gas. The nominal doping ratio was 4000:1 (Si:B) and the growth time was 20 minutes. The resulting SiNWs were dissolved in ethanol by gentle sonication for ~10 seconds. Then the NW solution was deposited onto a 50 nm-thick, 100 µm×100 µm silicon nitride TEM membrane grid (SPI supplies, West Chester, PA). Electron beam lithography and evaporation of a 60 nm-thick layer of nickel were carried out to fabricate ~1 µm spaced-apart source and drain electrodes on the nanowire. A layer of thickness of about 75-100 nm of silicon nitride was then deposited by plasma enhanced CVD (NEXX Systems, Billerica, MA) on the chip immediately after metal evaporation, to passivate all electrodes.

Lift-off of the mask was then carried out to produce a nanowire on a nitride membrane having passivated source and drain electrodes. The structure was then annealed by a rapid thermal processor (HeatPulse 610, Total Fab Solutions, Tempe, AZ) in forming gas at 380° C. for 135 seconds to shrink the nanowire channel to an extent less than about 200 nm. After conductivity testing of the resulting SiNW FET, the structure was cleaned by UV-ozone stripper (Samco International Inc., Amityville, NY) at 150° C. for 25 minutes on each side. The structure was then loaded into a field emission transmission electron microscope (TEM) (JEOL 2010, 200 kV) and a nanopore of about 9 nm or 10 nm in extent was drilled by through the nanowire at a selected location by convergent high energy electron beam into one spot for approximately 2-5 minutes. The nanopore was sited at the edge of the nanowire, as depicted in the arrangement of FIG. 22B, whereby a substantial portion of the nanowire width was continuous.

Example II

Sensitivity Profiling of a SiNW FET In a Nanopore Sensor

The sensitivity of the SiNW FET sensor of the nanopore sensor was characterized by scanning gate microscopy (SGM). A SiNW FET device was fabricated in accordance with the method of Example I, here with ~2 µm long channel length to accommodate the limited spatial resolution of SGM. SGM was performed in a Nanoscope IIIa Multi-Mode AFM (Digital Instruments Inc., Tonawanda, NY) by recording the conductance of the nanowire as a function of the position of a −10 V biased conductive AFM tip (PPP-NCHPt, Nanosensors Inc., Neuchatel, SW). The AFM tip was 20 nm above the surface during SGM recording.

Figure 23:
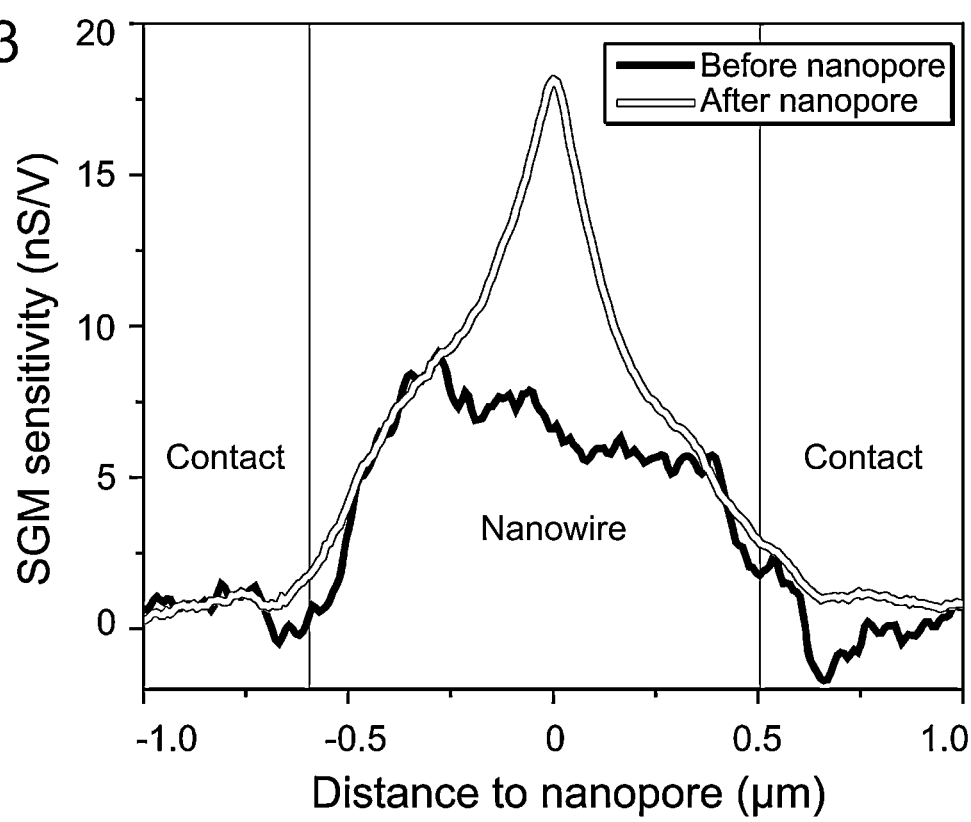
FIG. 23 is a plot of the sensitivity of a nanowire in a nanopore sensor configured for local electrical potential measurement before and after formation of a nanopore at the nanowire location.

Prior to formation of a nanopore at the nanowire site, an SGM profile was produced across the nanowire. Then a nanopore was formed at the edge of the nanowire in the arrangement depicted in FIG. 22B. With the nanopore present, the SGM profile of the nanowire was again produced. The SGM profile was determined by averaging the conductance over the apparent width (~100 nm) of the Si NW in a perpendicular direction using WSxM software. FIG. 23 is a plot of sensitivity, defined as conductance change divided by AFM tip gate voltage, along the nanowire before nanopore formation and after nanopore formation. It is clear that the sensitivity of the device is sharply localized and aligned with the nanopore. More importantly, the sensitivity of the nanopore region is also significantly enhanced compared to the sensitivity of the same region prior to nanopore formation.

Example III

Cleaning and Assembly of a Nanowire-Nanopore in a Nanopore Sensor

The nanowire-nanopore assembly produced by the method of Example I above was cleaned by UV-ozone stripper (Samco International Inc.) at 150° C. for 25 minutes on each side after formation of the nanopore. This cleaning process is preferred to remove any possible carbon deposition on the structure. Then the structure was annealed in forming gas at 250° C.-350° C. for 30 seconds to recover the conductance of the nanowire. A further 25 minute room temperature UV-ozone cleaning was performed on each side of the structure to ensure hydrophilicity of the nanopore just before assembly.

To assemble the nanowire-nanopore structure with fluidic reservoirs for species translocation through the nanopore, PDMS chambers were sonicated first in DI water, then 70% ethanol and finally pure ethanol, each for ~30 minutes and then stored in pure ethanol. Just before assembly, PDMS chambers were baked in a clean glass petri dish at ~80° C. for ~2 hours to remove most of the absorbed ethanol.

A printed circuit board (PCB) chip carrier was produced for making electrical connection to the nanopore sensor, and was cleaned by Scotch-Brite (3M, St. Paul, MN) to remove the copper surface oxide and any contaminants such as glue. The PCB was then sonicated in isopropyl alcohol and then in 70% ethanol, each for ~30 minutes. Gold solution electrodes were cleaned in piranha solution for ~1 hour just before assembly.

The cleaned nanowire-nanopore structure was glued into a ~250 µm-deep center pit of the PCB chip carrier using Kwik-Cast (World Precision Instruments, Inc., Sarasota, FL) silicone glue, with the device side surface approximately flush to the surface of the rest of PCB chip carrier. The source and drain electrical contacts of the device were wired to copper fingers on the chip carrier by wire bonding (West-Bond Inc., Anaheim, CA). The front PDMS chamber was formed of a piece of PDMS with a ~1.8 mm hole in the center, with a protrusion of ~0.5 mm around one side of the hole opening, for pressing against the nanopore membrane surface to ensure a tight seal. The PDMS chambers were mechanically clamped onto both sides of the chip carrier and Au electrodes were inserted through the PDMS reservoirs. The gold electrodes function as electrical connections for biasing the PDMS chamber solutions to produce a trans-membrane voltage (TMV) for driving species translocation through the nanopore electrophoretically.

The trans chamber was selected as the reservoir in which potential measurements would be made for the nanopore sensor. Thus, the assembly was arranged with the membrane oriented such that the nanowire was located facing the trans reservoir. The trans chamber was filled with a solution having a concentration of ~10 mM buffer, with 10 mM KCl+0.1×TAE buffer: 4 mM tris-acetate and 0.1 mM EDTA solution. The cis chamber was accordingly filled with a higher ionic concentration solution to provide the requisite reservoir concentration ratio to provide a higher assess resistance at the site of local potential measurement, in the trans chamber. The cis chamber was filled with a solution of ~1 M buffer, as 1 M KCl+1×TAE buffer: 40 mM tris-acetate and 1 mM EDTA. Both solutions were auto-cleaved, degassed by house vacuum and filtered by 20 nm Anotop syringe filter (Whatman Ltd., Kent, UK) before use.

Example IV

Nanopore Sensing of DNA Translocation Through the Nanopore

The nanowire-nanopore structure produced by the methods of the examples above and assembled with the solutions having buffer concentrations as prescribed by Example III was operated for sensing translocation of species objects, namely, double stranded DNA molecules of 1.4 nM pUC19 (dsDNA). Both the ionic current through the nanopore and the current from the nanowire FET device were measured.

The ionic current was amplified by an Axon Axopatch 200B patch-clamp amplifier (Molecular Devices, Inc., Sunnyvale, CA) with β=0.1 (1 nA convert to 100 mV) and 2 kHz bandwidth. The nanowire FET current was amplified by a DL 1211 current amplifier (DL Instruments) with a $10^6$ magnification (1 nA convert to 1 mV) and a 0.3 ms rise time. Both the trans-membrane voltage (TMV) and voltage between the nanowire FET source and drain electrodes, $V_{sd}$, were acquired by an Axon Digidata 1440A digitizer (Molecular Devices, Inc.). Both nanopore ionic current and nanowire FET signals were fed into a 1440A digitizer, and recorded at 5 kHz by a computer. Operation of the nanopore sensor was carried out in a dark Faraday cage. To avoid 60 Hz noise that could be introduced by the electrical grounding from different instruments, the ground line was removed from all current amplifiers and all instruments (Amplifiers and digitizer) and the Faraday cage and were manually grounded to the building ground together.

Figure 24A:
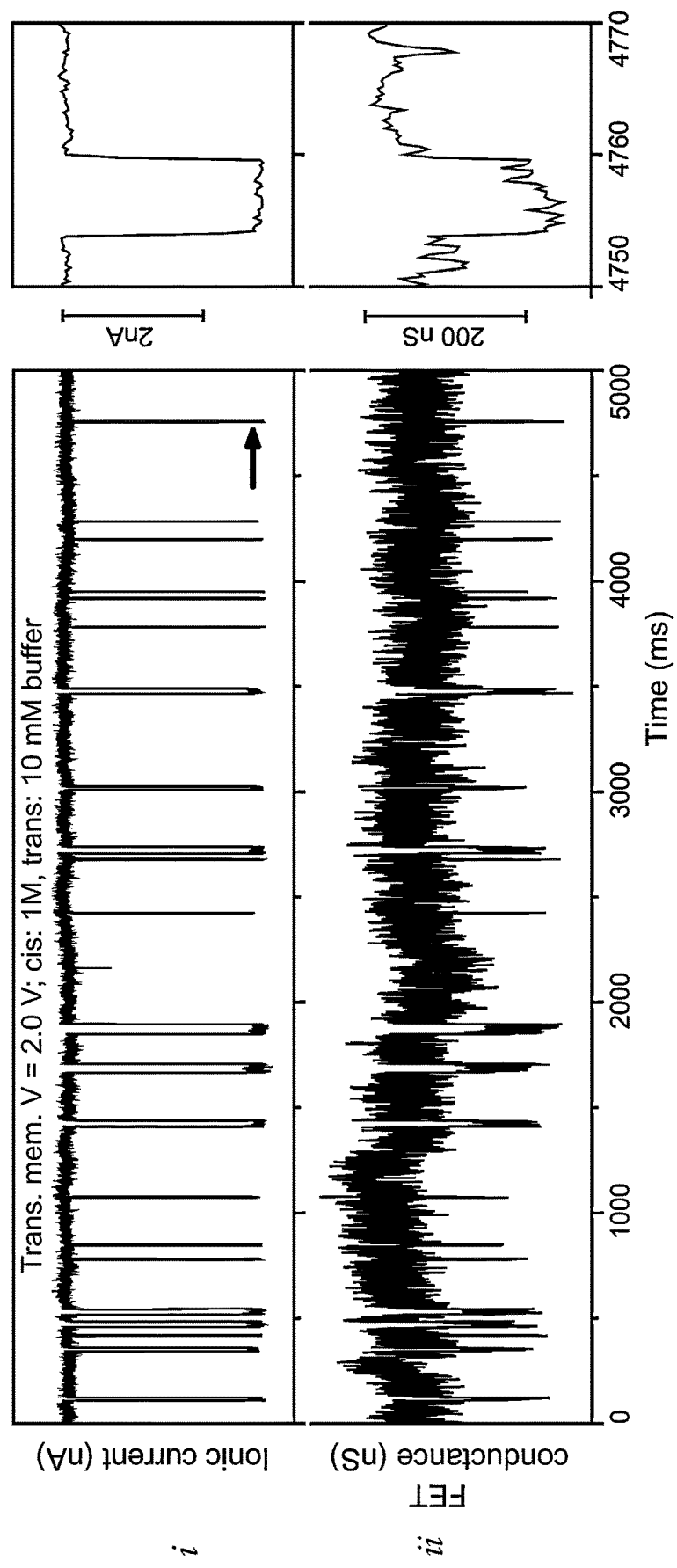
FIG. 24A is a plot of i) measured ionic current through a nanopore and ii) measured nanowire FET conductance, respectively, as DNA translocates through a nanopore in a nanopore sensor configured for local electrical potential measurement, for a TMV of 2 V and 100:1 cis/trans reservoir solution concentration ratio, with a local potential measurement made in the trans reservoir.
Figure 24B:
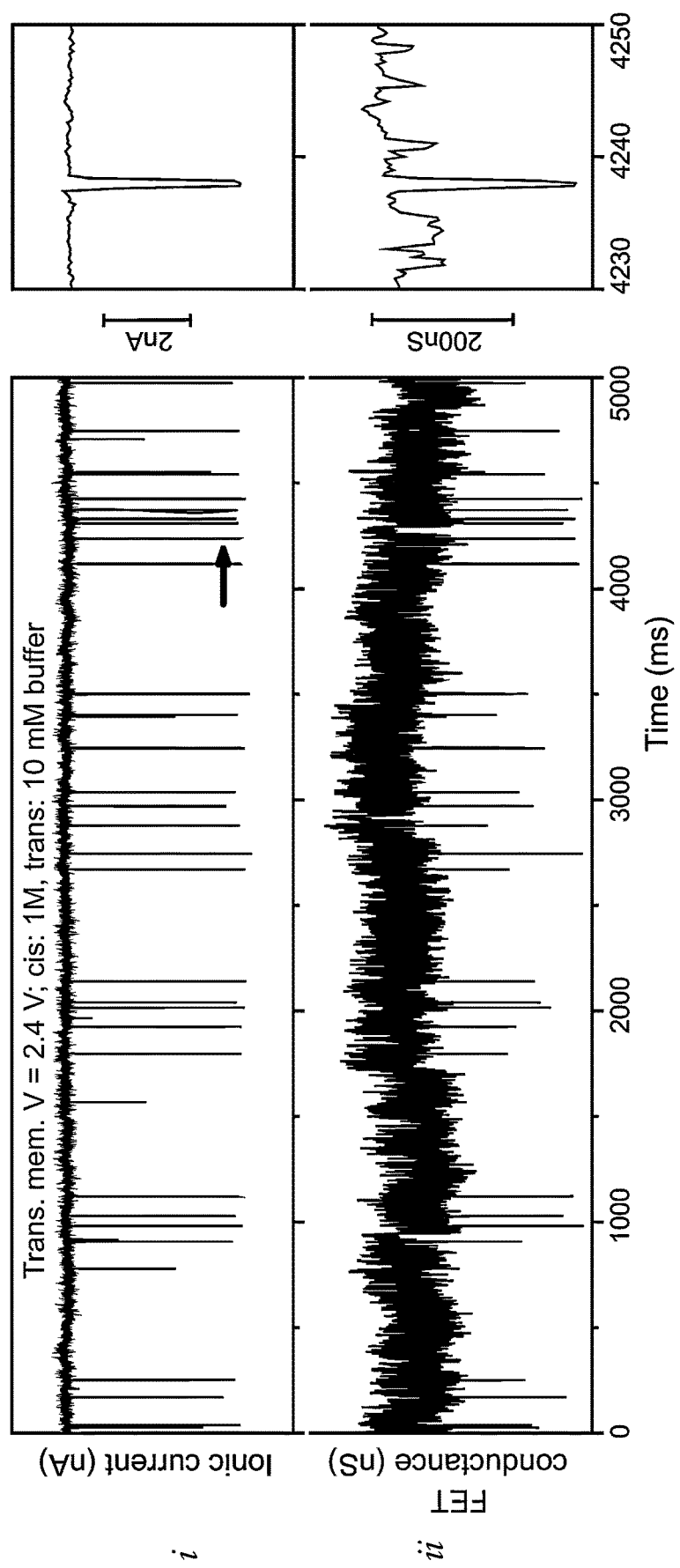
FIG. 24B is a plot of i) measured ionic current through a nanopore and ii) measured nanowire FET conductance, respectively, as DNA translocates through a nanopore in a nanopore sensor configured for local electrical potential measurement, for a TMV of 2.4 V and 100:1 cis/trans reservoir solution concentration ratio, with a local potential measurement made in the trans reservoir.

Upon introduction of the dsDNA into the cis reservoir, intermittent translocation events were recorded from the nanopore ionic current signal channel when the TMV reached ~2 V. For the nanowire FET signal channel, similar events were recorded in the conductance trace with almost perfect time correlation with the ionic current measurements. FIG. 24A includes a plot, i, of the measured ionic current through the nanopore, and a plot, ii, of the measured nanowire FET conductance for a 2.0 V TMV. FIG. 24B shows a plot, i, of the measured ionic current through the nanopore, and a plot, ii, of the measured nanowire FET conductance for a 2.4 V TMV. As the TMV was increased, the duration and frequency of translocation events measured by ionic current through the nanopore and measured by nanowire FET local potential sensing decreased and increased respectively. From the plots it is shown that the local potential measurement sensing method perfectly tracks the sensing by conventional ionic current measurement. The local potential measurement method thereby enables the determination of the time of and the duration of translocation of an object through the nanopore.

To directly compare the signal amplitudes of the FET local potential measurement signal and the nanopore ionic current measurement signal, the FET conductance signal of ~200 nS and baseline of ~24 µS was converted into a current by multiplying the signal by the 150 mV source-drain voltage. This calculation indicates that for ~2 nA of change in ionic current through the nanopore, with a ~12 nA baseline, there is produced an amplification to ~30 nA of FET current in the nanowire local potential measurement, with a ~3.6 µA baseline. Considering that current fabrication processes are not optimized for low noise devices and that a far higher signal-to-noise ratio has been demonstrated for SiNWs in general, the noise and signal-to-noise ratio of the nanowire FET itself is not be the fundamental limiting factor of this measurement.

Example V

Local Potential Measurement Dependence on Cis and Trans Reservoir Buffer Concentration Difference To determine the impact of different ionic concentration fluids in the cis and trans reservoirs of the nanopore sensor, a nanowire-nanopore structure was configured following the procedure in Example III above, but here with both cis and trans chambers filled with 1 M KCl buffer instead of solutions having differing buffer concentrations. Operation of the nanopore sensor was then conducted with dsDNA provided in the trans reservoir, following the procedure of Example IV above, with a TMV of 0.6 V. The ionic current through the nanopore was measured, as was the local potential, via nanowire FET conductance in the manner of Example IV.

Figure 24C:
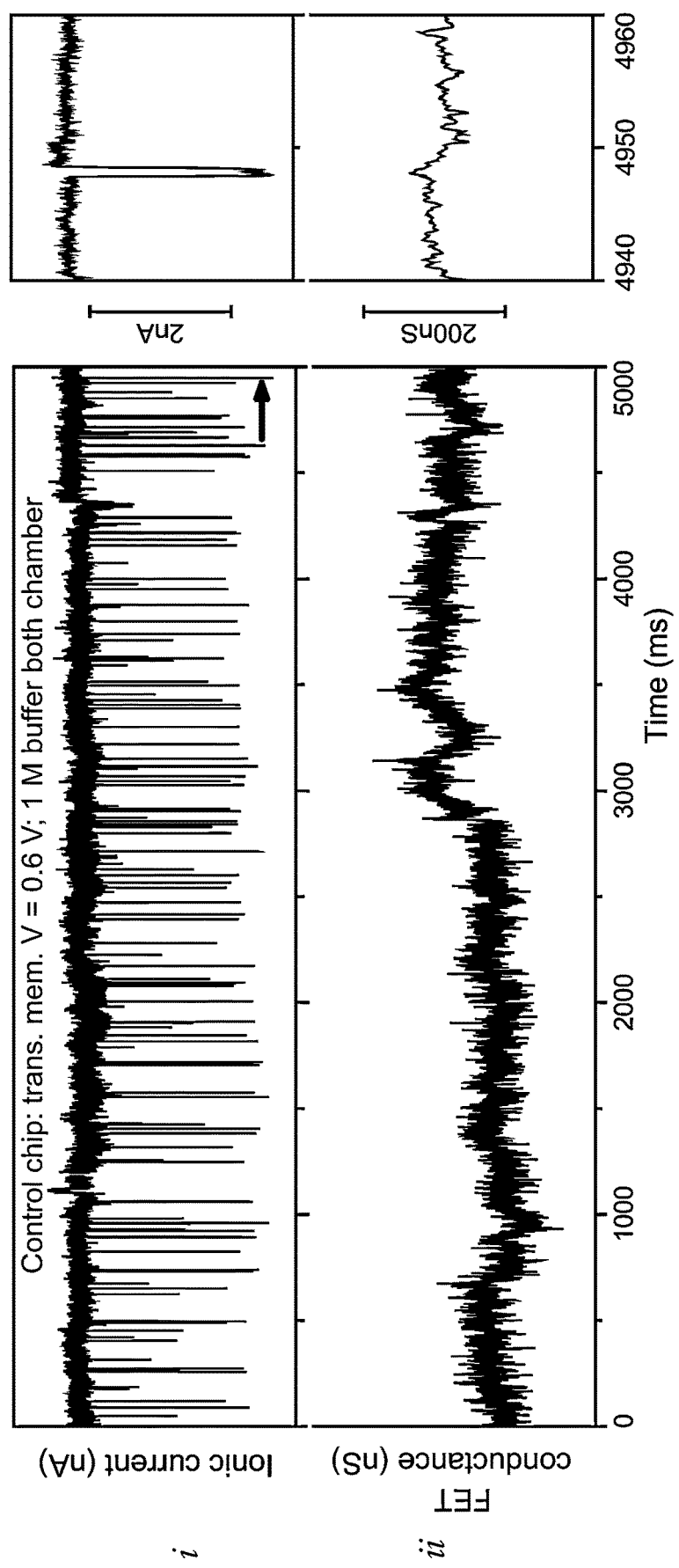
FIG. 24C is a plot of i) measured ionic current through a nanopore and ii) measured nanowire FET conductance, respectively, as DNA translocates through a nanopore in a nanopore sensor configured for local electrical potential measurement, for a TMV of 0.6 V and 1:1 cis/trans reservoir solution concentration ratio, with a local potential measurement made in the trans reservoir.

FIG. 24C provides plots including plot i, of the measured ionic conductance and ii, of the measured FET conductance. As shown in the plots, translocation events were sensed by changes in ionic current when the TMV reached 0.5-0.6 V but the simultaneously-recorded FET conductance change was negligible at that voltage. The reservoir solution concentration ratio is therefore understood to play an important role in the signal generation.

Under the balanced buffer solution concentration conditions (1 M/1 M) of this experiment, the nanopore solution resistance contributes the majority of the resistance of the nanopore sensor; thus, almost all of the TMV drops across the nanopore. The electrical potential in the vicinity of the nanowire sensor is accordingly for this condition very close to ground regardless of any change in the solution resistance of the nanopore and access resistances of the reservoirs due to blockade during species translocation. Under the non-balanced buffer conditions (10 mM/1 M) of Example IV above, the nanopore solution resistance and the trans chamber access resistance are comparable, while the access resistance of cis chamber is still negligible. Any change of the solution resistance in the nanopore and access resistance in the trans reservoir causes a corresponding redistribution of TMV and thus a change in the electrical potential in the vicinity of the nanopore at the trans chamber, and this potential change is what is easily detected by the local potential measurement of the nanopore sensor.

This example validates the discovery herein that local potential measurement nanopore sensing is preferably conducted with a difference in buffer solution concentration between the reservoirs of a nanopore sensor, and that the local potential measurement is to be conducted at the reservoir-side of the nanopore having a higher resistance, or correspondingly lower concentration. This condition is not applicable to nanopore sensors wherein the membrane is sufficiently thin to operate as a nanowire and to sense the potential on both sides of the membrane, as in graphene nanopore sensors in which a graphene nanowire provides an indication of a difference between potential on the two sides of a nanopore. In this case, a difference in buffer solution concentration is still preferable, but the local potential measurement is not strictly limited to one side or the other of the nanopore, given that the nanowire measurement inherently senses the potential on both sides of the membrane.

Note in the experiments above in which the reservoir solution concentrations were equal and were unequal required differing transmembrane voltages to initial translocation through the nanopore. For potential measurement in the trans reservoir, with equal solution concentrations, the electric field through the nanopore is constant, as shown in the plot of FIG. 3D. When the reservoir concentrations are different, e.g., the 100:1 concentration of the examples above, then the electric field through the nanopore is smaller on the cis reservoir-side of the nanopore. To produce the same electric field as that obtained with equal reservoir solution concentrations, the transmembrane voltage is required to be increased by about 4 times. This explains the data of the plots of FIGS. 23 and 24.

Example VI

Multi-Channel Nanopore Sensing

Three nanowire nanopore sensors were constructed following the methods of the examples above. The three nanopore sensors were integrated with a common reservoir system, with a 1 M KCl buffer solution in the cis chamber and a 10 mM KCl buffer in the trans chamber. A transmembrane voltage of 3 V was employed, and 1.4 nM of pUC19 DNA was provided for translocation through the nanopores.

Figure 25:
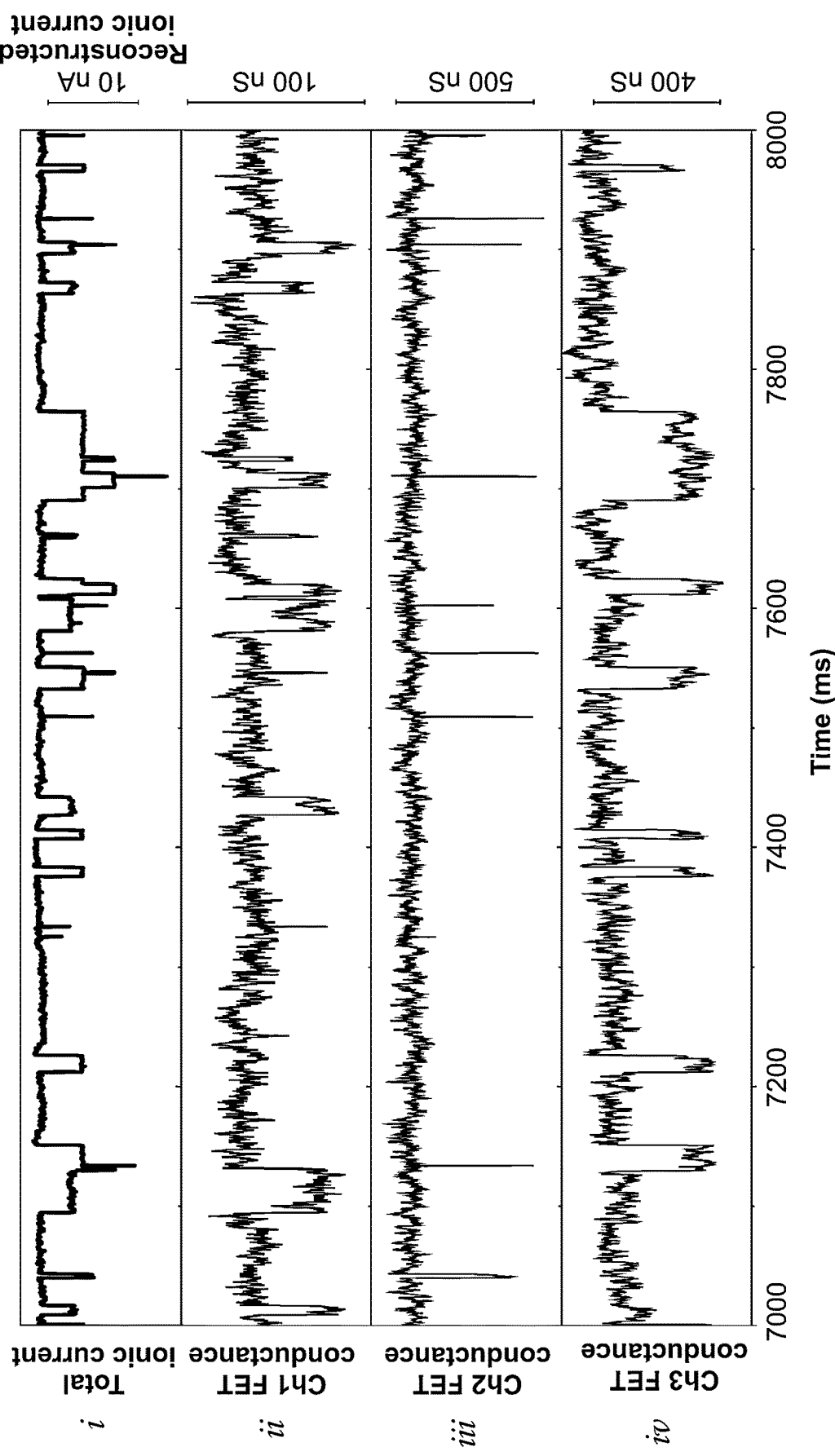
FIG. 25 is a plot of i) total ionic current measured through three nanopores sharing reservoirs, ii) measured nanowire FET conductance through the first of the nanopores, ii) measured nanowire FET conductance through the second of the nanopores, and ii) measured nanowire FET conductance through the third of the nanopores, respectively, as DNA translocates through the nanopores in the three sensors in a nanopore sensor configured for local electrical potential measurement.

FIG. 25 provides plots i-iv of total ionic current and the nanowire FET conductance of each of the three nanopore sensors, respectively, during DNA nanopore translocation operation. As shown in the plots, continuous translocation events are observed in all three nanopore sensors as well as the total ionic current channel. All nanopore sensors operated independently and every falling or rising edge apparent in the ionic current channel can be uniquely correlated to a corresponding edge in one of the three nanopore sensors. Using the falling and rising edge of signals from all three nanopore sensors to reconstruct the total ionic current trace, the reconstruction is nearly perfect for of all events. This nanopore operation demonstrates that a key advantage of the nanopore sensor is the large scale integration capability. Multiple independent nanopore sensors can be implemented without need for complex micro-fluidic systems.

Example VII

Nanopore Sensor with a Fluidic Passage

A nanowire nanopore sensor was constructed following the methods of the examples above. Included was a 1 µm-diameter, 50 µm-long fluidic passage in a dielectric material connected between a fluidic reservoir and the nanopore. In the nanowire was disposed a protein nanopore in a lipid bilayer in an aperture of about 100 nm in the nanowire channel. The protein nanopore had an effective geometry of 1.5 nm in diameter and 4.5 nm in length. An ionic solution of 1.6M was provided in the cis reservoir and an ionic solution of 1 mM was provided in the trans reservoir. A 300 mV bias was applied across the nanopore for electrophoretically driving ssDNA through the nanopore.

Prior to ssDNA translocation, the electrical potential of the fluidic passage, at the bottom of the passage, was measured to be 150 mV and the voltage across the nanopore was 150 mV. When the ssDNA translocated through the nanopore, the effective nanopore diameter was 1.12 nm, and the electrical potential at the bottom of the fluidic passage was measured to be 128 mV, with the voltage across the nanopore being 172 mV. The measured voltage signal corresponding to ssDNA translocation was 22 mV. This signal was distributed uniformly at the bottom of the fluidic passage, at the FET sensing surface, and did not change as the biological nanopore moved within the lipid membrane.

With these examples and the preceding description, it is demonstrated that the nanopore sensor can provide sensing of species translocating through a nanopore and can discriminate between differing objects, such as DNA bases, as those objects translocate through the nanopore. The nanopore sensor is not limited to sensing of a particular species or class of species and can be employed for a wide range of applications. It is recognized that the nanopore sensor is particularly well-suited for sensing of biopolymer molecules that are provided for translocation through the nanopore. Such molecules include, e.g., nucleic acid chains such as DNA strands, an oligonucleotide or section of single-stranded DNA, nucleotides, nucleosides, a polypeptide or protein, amino acids in general, or other biological polymer chain. There is no particular limitation to the species object to be sensed by the nanopore sensor. With differing reservoir solution concentrations, a fluidic passage configuration, or some combination of these two features, it is demonstrated that the nanopore sensor can operate with reasonable bandwidth and sensitivity for discriminating DNA bases, and therefore enables DNA sequencing.

It is recognized, that those skilled in the art may make various modifications and additions to the embodiments described above without departing from the spirit and scope of the present contribution to the art. Accordingly, it is to be understood that the protection sought to be afforded hereby should be deemed to extend to the subject matter claims and all equivalents thereof fairly within the scope of the invention.

I claim:

1. A nanopore sensor comprising:
a nanopore disposed in a support structure, the nanopore having a nanopore diameter and a nanopore fluidic resistance, $R_{Pore}$;
a first fluidic reservoir including a fluidic solution having a first ionic concentration;
a fluidic passage disposed in fluidic connection between the first fluidic reservoir and the nanopore, the fluidic passage including a passage length having a fluidic passage width, along at least a portion of a fluidic passage length, that is greater than the diameter of the nanopore and less than the fluidic passage length, and the fluidic passage having a fluidic passage fluidic resistance, $R_{FP}$, of at least about 10% of the nanopore fluidic resistance, $R_{Pore}$, and no more than about 10 times the nanopore fluidic resistance, $R_{Pore}$;
a second fluidic reservoir including a fluidic solution having a second ionic concentration, the nanopore being disposed in fluidic connection between the second fluidic reservoir and the fluidic passage; and
at least one transistor operatively connected electrically to sense electrical potential local to the fluidic passage.

2. The nanopore sensor of claim 1 further comprising at least one electrode operatively connected to the electrical transistor to sense electrical potential local to the fluidic passage.

3. The nanopore sensor of claim 2 wherein the electrode comprises a metal electrode.

4. The nanopore sensor of claim 2 wherein the at least one electrode comprises a plurality of electrodes.

5. The nanopore sensor of claim 1 further comprising at least one of an electrical device, an electrical device region, and an electrical circuit operatively connected to the electrical transistor to sense electrical potential local to the fluidic passage.

6. The nanopore sensor of claim 1 wherein the electrical transistor comprises an electronic conduction channel disposed at the fluidic passage.

7. The nanopore sensor of claim 1 wherein the electrical transistor selected comprises a field effect transistor.

8. The nanopore sensor of claim 1 wherein the support structure in which the nanopore is disposed comprises a membrane.

9. The nanopore sensor of claim 1 wherein the support structure in which the nanopore is disposed comprises a solid state material.

10. The nanopore sensor of claim 1 wherein the nanopore comprises a biological nanopore.

11. The nanopore sensor of claim 1 wherein the nanopore comprises a biological nanopore in a lipid bilayer disposed in an aperture of a solid state material.

12. The nanopore sensor of claim 1 wherein the nanopore comprises a protein nanopore.

13. The nanopore sensor of claim 1 wherein the support structure in which the nanopore is disposed comprises an amphiphilic membrane.

14. The nanopore sensor of claim 1 wherein the support structure in which the nanopore is disposed comprises a lipid bilayer.

15. The nanopore sensor of claim 1 further comprising a molecular motor disposed at the nanopore.

16. The nanopore sensor of claim 1 further comprising an electrical circuit connected to the transistor to produce indications of sensed electrical potential local to the fluidic passage as a function of time.

17. The nanopore sensor of claim 1 wherein the fluidic solution of at least one of the first reservoir and the second reservoir includes biological molecules comprising at least one of DNA, DNA fragments, RNA, RNA fragments, PNA, nucleotides, nucleosides, oligonucleotides, proteins, polypeptides, amino acids, and polymers.

18. The nanopore sensor of claim 1 wherein the first ionic concentration of the fluidic solution of the first fluidic reservoir differs from the second ionic concentration of the second fluidic reservoir.

19. The nanopore sensor of claim 1 further comprising electrodes connected to an electrical voltage source operative to apply an electrical voltage between the first fluidic reservoir and the second fluidic reservoir.

20. The nanopore sensor of claim 1 further comprising a material layer disposed on the support structure, and wherein the fluidic passage length is disposed laterally in the material layer.

21. The nanopore sensor of claim 1 wherein the fluidic passage length comprises a horizontal fluidic passage length, and wherein the fluidic connection between the first reservoir and the horizontal fluidic passage length comprises a vertical fluidic connection and the fluidic connection between the nanopore and the horizontal fluidic passage length comprises a vertical fluidic connection.

22. A nanopore sensor comprising:
a nanopore disposed in a support structure, the nanopore having a nanopore diameter and a nanopore fluidic resistance, $R_{Pore}$;
a first fluidic reservoir including a fluidic solution having a first ionic concentration;
a fluidic passage disposed in fluidic connection between the first fluidic reservoir and the nanopore, the fluidic passage including a passage length having a fluidic passage width, along at least a portion of a fluidic passage length, that is greater than the diameter of the nanopore and less than the fluidic passage length, the fluidic passage length including at least one lateral fluidic passage section that winds around itself laterally, and the fluidic passage having a fluidic passage fluidic resistance, $R_{FP}$, of at least about 10% of the nanopore fluidic resistance, $R_{Pore}$, and no more than about 10 times the nanopore fluidic resistance, $R_{Pore}$;
a second fluidic reservoir including a fluidic solution having a second ionic concentration, the nanopore being disposed in fluidic connection between the second fluidic reservoir and the fluidic passage; and
at least one transistor operatively connected electrically to sense electrical potential local to the fluidic passage.

23. A nanopore sensor comprising:
a nanopore disposed in a support structure, the nanopore having a nanopore diameter and a nanopore fluidic resistance, $R_{Pore}$;
a first fluidic reservoir including a fluidic solution having a first ionic concentration;
a fluidic passage disposed in fluidic connection between the first fluidic reservoir and the nanopore, the fluidic passage including a passage length having a fluidic passage width, along at least a portion of a fluidic passage length, that is greater than the diameter of the nanopore and less than the fluidic passage length, the fluidic passage comprising at least two different vertical fluidic passage sections and a horizontal fluidic passage length, and the fluidic passage having a fluidic passage fluidic resistance, $R_{FP}$, of at least about 10% of the nanopore fluidic resistance, $R_{Pore}$, and no more than about 10 times the nanopore fluidic resistance, $R_{Pore}$;
a second fluidic reservoir including a fluidic solution having a second ionic concentration, the nanopore being disposed in fluidic connection between the second fluidic reservoir and the fluidic passage; and
at least one transistor operatively connected electrically to sense electrical potential local to the fluidic passage.

* * * * *